United States Patent
Marchitto et al.

(10) Patent No.: US 6,315,772 B1
(45) Date of Patent: Nov. 13, 2001

(54) LASER ASSISTED PHARMACEUTICAL DELIVERY AND FLUID REMOVAL

(75) Inventors: Kevin S. Marchitto; Stephen T. Flock, both of Little Rock, AR (US)

(73) Assignee: Transmedica International, Inc., Little Rock, AR (US)

(*) Notice: Subject to any disclaimer, the term of this patent is extended or adjusted under 35 U.S.C. 154(b) by 67 days.

(21) Appl. No.: 08/955,789

(22) Filed: Oct. 22, 1997

Related U.S. Application Data

(63) Continuation-in-part of application No. 08/792,335, filed on Jan. 31, 1997, now abandoned, which is a continuation-in-part of application No. 08/126,241, filed on Sep. 24, 1993, now Pat. No. 5,643,252.

(51) Int. Cl.$^7$ .................................................. A16N 5/00
(52) U.S. Cl. ...................... 606/9; 607/88; 606/3; 606/10; 606/17; 604/21; 128/770
(58) Field of Search ............... 606/2–17; 604/21; 128/770; 607/88–89

(56) References Cited

U.S. PATENT DOCUMENTS

| | | |
|---|---|---|
| 3,865,113 | 2/1975 | Sharon et al. |
| 4,028,636 | 6/1977 | Hughes. |
| 4,628,416 | 12/1986 | Dewey. |
| 4,648,892 | 3/1987 | Kittrell et al. |

(List continued on next page.)

FOREIGN PATENT DOCUMENTS

| | | |
|---|---|---|
| 0214712 A1 | 3/1987 | (EP). |
| 4-314428 | 11/1992 | (JP). |
| 7-39542 | 2/1995 | (JP). |
| 2005515 | 1/1994 | (RU). |
| 2027450 | 1/1995 | (RU). |
| 1614808 | 3/1988 | (SU). |
| 1670858 | 10/1989 | (SU). |
| WO92/14514 | 9/1992 | (WO). |
| WO94/09713 | 5/1994 | (WO). |
| WO97/07734 | 3/1997 | (WO). |

OTHER PUBLICATIONS

Nelson et al., Mid–Infrared Laser Ablation of stratum Corneum Enhances In Vitro Percutaneous Transport of Drugs, The Society for Investigatiove Dermatology, Inc., pp. 874–879, Sep. 10, 1990.*

(List continued on next page.)

*Primary Examiner*—Gary O'Connor
*Assistant Examiner*—Michael Astorino
(74) *Attorney, Agent, or Firm*—Lyon & Lyon LLP

(57) ABSTRACT

The present invention provides an improved method of removing fluids, gases or other biomolecules, or delivering a pharmaceutical composition, through the skin of a patient without the use of a sharp or needle. The method includes the step of irradiating the stratum corneum, an applied pharmaceutical or an absorbing material, using a laser. By selection of parameters, the laser irradiates the selected material or tissue to create pressure gradients, plasma, cavitation bubbles, or other forms of tissue ablation or alteration. These methods increase the diffusion of pharmaceuticals into, or fluids, gases or other biomolecules out of, the body. For this invention, a pharmaceutical composition can be applied to the skin before or after laser irradiation.

77 Claims, 28 Drawing Sheets

U.S. PATENT DOCUMENTS

| | | |
|---|---|---|
| 4,710,940 | 12/1987 | Sipes, Jr. . |
| 4,712,537 | 12/1987 | Pender . |
| 4,775,361 * | 10/1988 | Jacques et al. .......................... 606/9 |
| 4,829,262 | 5/1989 | Furumoto . |
| 4,940,411 | 7/1990 | Vassiliadis et al. . |
| 4,941,093 | 7/1990 | Marshali et al. . |
| 4,951,663 | 8/1990 | L'Esperance, Jr. . |
| 5,066,291 | 11/1991 | Stewart . |
| 5,066,293 | 11/1991 | Furumoto . |
| 5,074,861 | 12/1991 | Schneider et al. . |
| 5,125,922 | 6/1992 | Dwyer et al. . |
| 5,165,418 * | 11/1992 | Tankovich ................................ 606/9 |
| 5,182,759 | 1/1993 | Anthon et al. . |
| 5,231,975 | 8/1993 | Bommannan et al. . |
| 5,246,436 * | 9/1993 | Rowe ..................................... 606/13 |
| 5,290,273 | 3/1994 | Tan . |
| 5,304,170 | 4/1994 | Green . |
| 5,312,395 | 5/1994 | Tan et al. . |
| 5,342,355 | 8/1994 | Long . |
| 5,360,426 | 11/1994 | Muller et al. . |
| 5,360,447 | 11/1994 | Koop . |
| 5,397,327 | 3/1995 | Koop et al. . |
| 5,421,816 | 6/1995 | Lipkowker . |
| 5,423,798 | 6/1995 | Crow . |
| 5,423,803 * | 6/1995 | Tankovich et al. ....................... 606/9 |
| 5,437,658 | 8/1995 | Muller et al. . |
| 5,445,611 | 8/1995 | Eppstein et al. . |
| 5,458,140 | 10/1995 | Eppstein et al. . |
| 5,461,212 | 10/1995 | Seiler et al. . |
| 5,468,239 | 11/1995 | Tanner et al. . |
| 5,522,813 | 6/1996 | Trelles . |
| 5,554,153 | 9/1996 | Costello et al. . |
| 5,556,612 * | 9/1996 | Anderson et al. ..................... 424/59 |
| 5,586,981 | 12/1996 | Hu . |
| 5,611,795 | 3/1997 | Slatkine et al. . |
| 5,614,502 | 3/1997 | Flotte et al. . |
| 5,617,851 | 4/1997 | Lipkovker . |
| 5,624,434 | 4/1997 | Abergel et al. . |
| 5,630,811 | 5/1997 | Miller . |
| 5,636,632 | 6/1997 | Bommannan et al. . |
| 5,642,370 | 6/1997 | Mitchell et al. . |
| 5,643,252 | 7/1997 | Waner et al. . |
| 5,644,585 | 7/1997 | Mitchell et al. . |
| 5,657,760 | 8/1997 | Ying et al. . |
| 5,658,892 | 8/1997 | Flotte et al. . |
| 5,713,845 | 2/1998 | Tankovich . |

OTHER PUBLICATIONS

"Laser Scarifier" advertisement in Russian, published Nov. 19, 1990; translation into English provided.

Jacques et al. "Controlled Removal of Human Stratum Corneum by Pulsed Laser," The Journal of Investigative Dermatology, vol. 88, No. 1, 1/87; pp. 88–93.

Walsh, J.T., "Optical–Thermal Response of Laser–Irradiated Tissue," Chapter 25, pp. 865–902 (Plenum Press, NY 1995).

Duck, F.A., "Physical Properties of Tissue," Chapter 4, pp. 74–135 (Academic Press, 1990).

S. Lee, "Application of Laser Generated Stress Waves for Molecular Delivery Through the Stratum Corneum," Whitaker Foundation Abstract, Approved Jan. 1997.

H. Shangguan et al., "Photoacoustic Drug Delivery: The Effect of Laser Parameters on Spatial Distribution of Delivered Drug," SPIE vol. 2391, Jun. 1995, pp. 394–402.

H. Shanngguan et al., "Drug Delivery with Microsecond Laser Pulses into Gelatin," Applied Optics, vol. 35, No. 19, Jul. 1996, pp. 3347–3357.

E.O. Esenaliev et al., "Transient and Permanent Cavitation in Collagen Gels by Laser–Induced Thermoelastic Pressure Waves," SPIE vol. 2681, Jul. 1996, pp. 185–193.

E.O. Esenaliev et al. "Effect of Tensile Stress Amplitude and Temporl Characteristics on Threshold of Cavitation–Driven Ablation" SPIE vol. 2681 Jul. 1996 pp. 326–333.

S. L. Jacques et al. "Laser–flash Photography of Laser–Induced Spallation in Liquid Media" SPIE vol. 1646 May 1992 pp. 284–294.

S. Flock et al. "Photoacoustic–induced Vascular Tissue Dissection Resulting from Irradiation with a Q–Switched Frequency–doubled Nd:YAG Laser" SPIE vol. 2395 Apr. 1995 pp. 170–176.

D. Stern et al. "Corneal Ablation by Nanosecond, Picosecond, and Ferntosecond Lasers at 532 and 625 nm" Archives of Ophthalmology Apr. 1989, vol. 107—American Medical Association, pp. 587–592.

L. Esterowitz, C.A. Hoffman, K. Levin and M. Storm, "Mid–IR Solid State Laser with Fiber Optics as an Ideal Medical Scalpel," In Proceedings Intern. Conference on Lasers, Las Vegas, 1985, pp. 68–71.

J. Havlice, "Medical Ultrasonic Imaging: An Overview of Principles and Instrumentation," Proceedings of IEEE, vol. 67, No. 4, Apr. 1979, pp. 620–641.

S.T. Flock and S.L. Jacques, "Thermal Damage of Blood Vessels in a Rat Skin–flap Window Chamber Using Indocyanine Green and a Pulsed Alexandrite Laser: A Feasibility Study," Lasers in Med, Science, 8:185–196.

J.S. Dover and G.J. Hruza, "laser Skin Resurfacing," Semin. in Cutaneous Med. and Surg., vol. 15, No. 3, Sep. 1996, pp. 177–188.

* cited by examiner

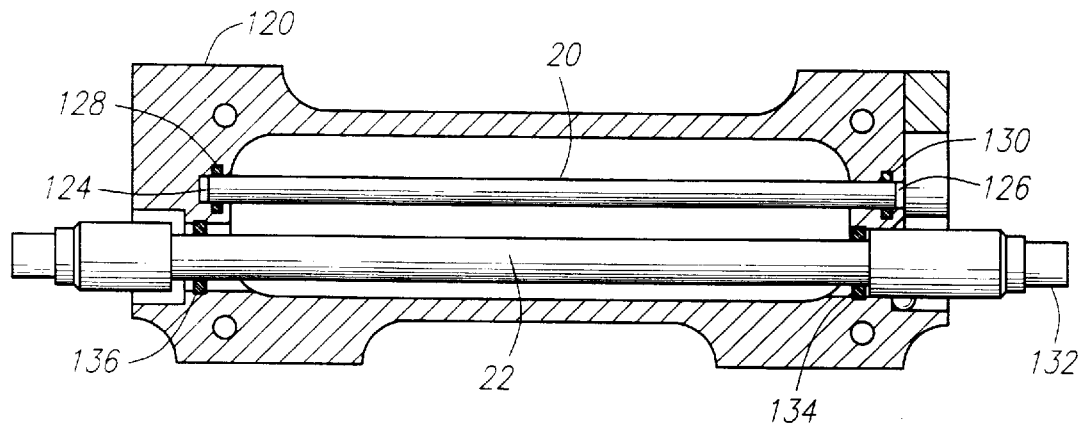
FIG. 12
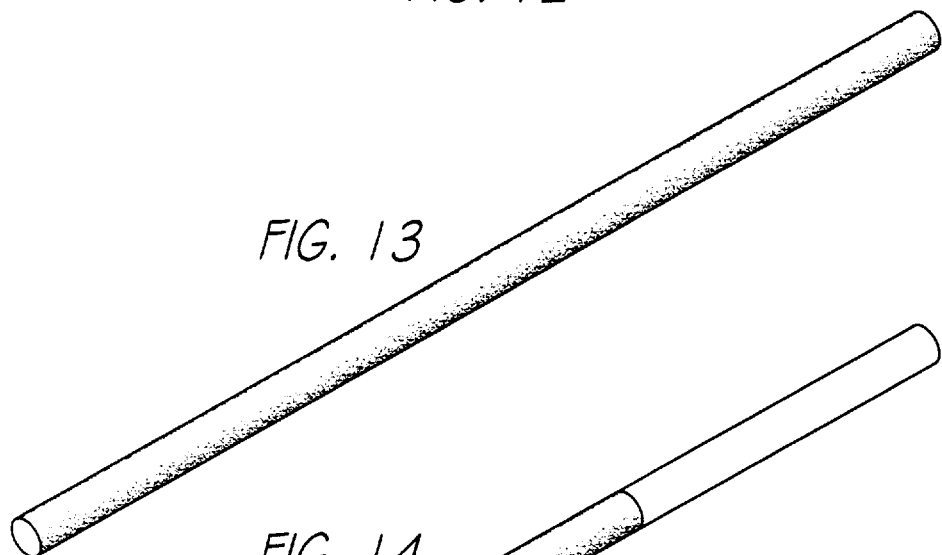
FIG. 13
FIG. 14
FIG. 15
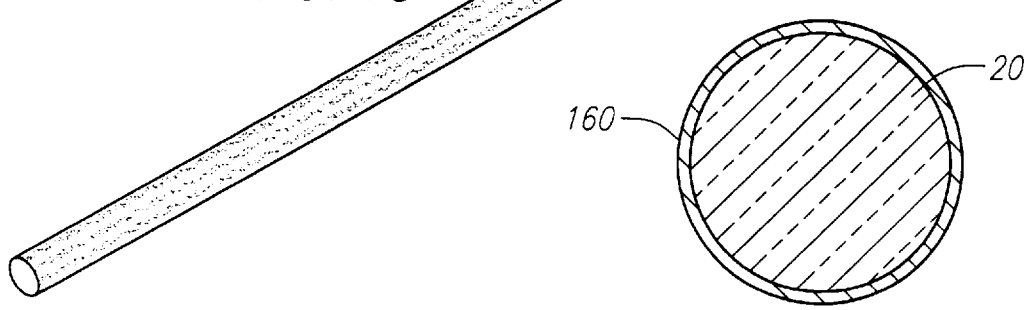
FIG. 16

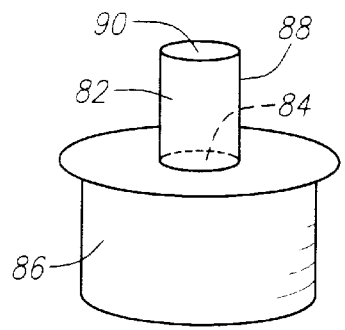
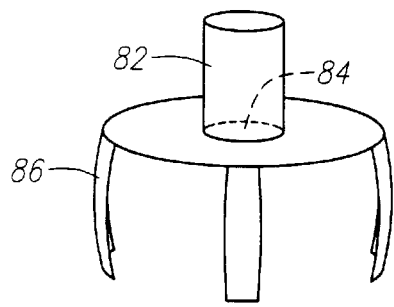
FIG. 17A    FIG. 17B
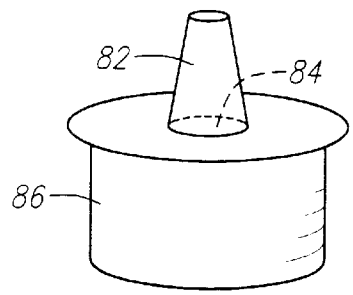
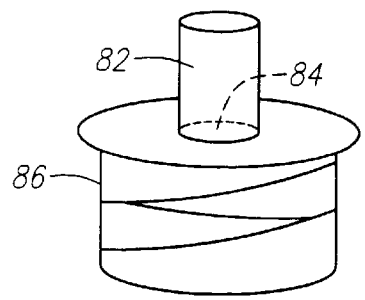
FIG. 17C    FIG. 17D
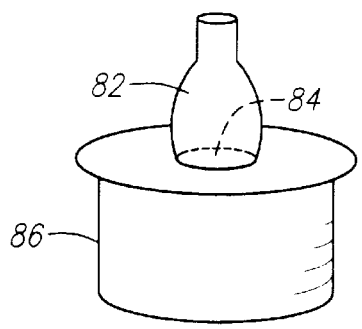
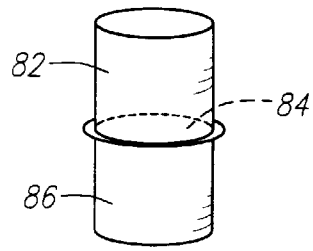
FIG. 17E    FIG. 17F
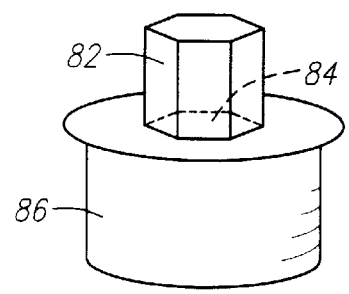
FIG. 17G

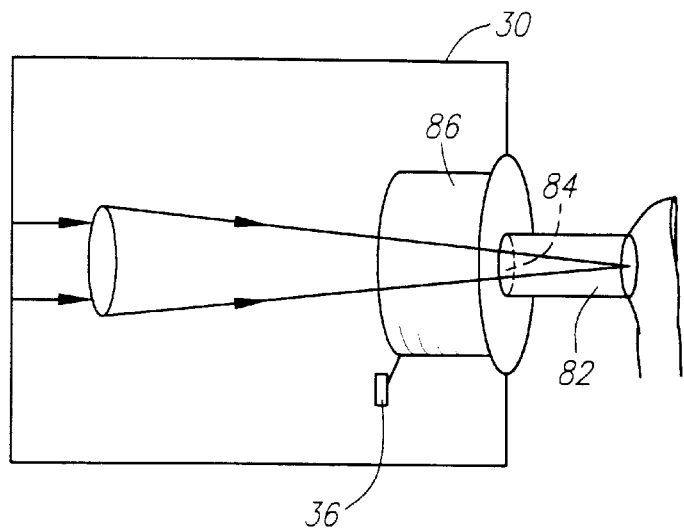
FIG. 19A
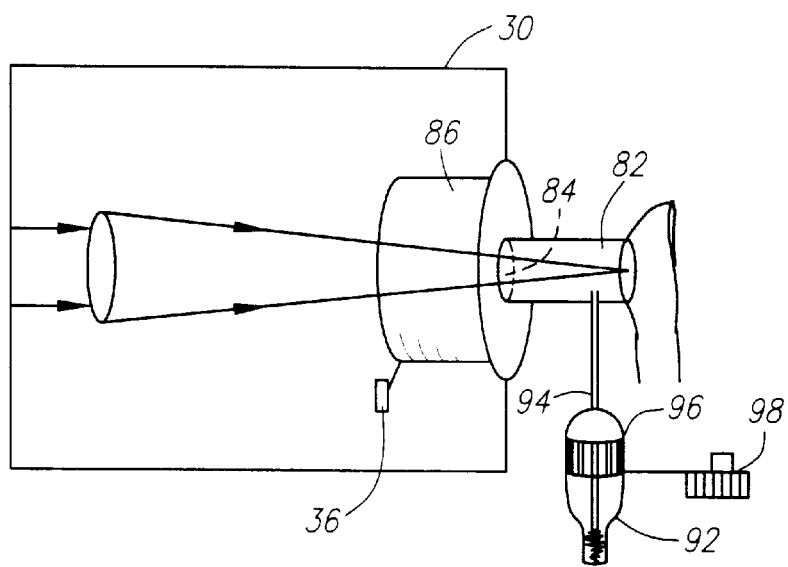
FIG. 19B
FIG. 20

READINGS ARE DIFFERENCES FROM SEPARATE CONTROLS ON CONTRALATERAL ARM

EFFECTIVELY INFINITE DOSE
(I.E. DRUG LEFT ON SKIN FOR DURATION OF EXPERIMENT)
-2MM SPOT/HUMAN SKIN IN VITRO

LASER ASSISTED PHARMACEUTICAL DELIVERY AND FLUID REMOVAL

This application is a continuation-in-part of U.S. Ser. No. 08/792,335 filed Jan. 31, 1997, now abandoned, which is a continuation-in-part of U.S. Ser. No. 08/126,241, filed Sep. 24, 1993, issued Jul. 1, 1997 as U.S. Pat. No. 5,643,252, all of which are incorporated herein by reference said application is incorporated herein by reference.

FIELD OF THE INVENTION

This invention is in the field of medical procedures, namely laser medical equipment used in the delivery of anesthetics or pharmaceuticals to, or the removal of fluids, gases or other biomolecules from, a patient.

BACKGROUND

The traditional method for the collection of small quantities of fluids, gases or other biomolecules from a patient utilizes mechanical perforation of the skin with a sharp device such as a metal lancet or needle. Additionally, the typical method of administering anesthetics or other pharmaceuticals is through the use of a needle.

These procedures have many drawbacks, including the possible infection of health care workers and the public by the sharp device used to perforate the skin, as well as the cost of handling and disposal of biologically hazardous waste.

When skin is perforated with a sharp device such as a metal lancet or needle, biological waste is created in the form of the "sharp" contaminated by the patient's blood and/or tissue. If the patient is infected with blood-born agents, such as human immunodeficiency virus (HIV), hepatitis virus, or the etiological agent of any other diseases, the contaminated sharp poses a serious threat to others that might come in contact with it. For example, many medical workers have contracted HIV as a result of accidental contact with a contaminated sharp.

Post-use disposal of contaminated sharps imposes both logistical and financial burdens on the end user. These costs are imposed as a result of the social consequences of improper disposal. For example, in the 1980's improperly disposed biological wastes washed up on public beaches on numerous occasions. Improper disposal also permits others, such as intravenous drug users, to obtain contaminated needles and spread disease.

There exists an additional drawback of the traditional method of using a needle for administering anesthetics or pharmaceuticals, as well as for drawing fluids, gases or other biomolecules. The pain associated with being stabbed by a the sharp instrument can be a traumatizing procedure, especially in pediatric patients, causing significant stress and anxiety in the patient. Moreover, for drawing fluids, gases or other biomolecules the stabbing procedure often must be repeated before sufficient fluid is obtained.

The current technology for applying local anesthetic without the use of needles typically involves either (a) topical lidocaine mixtures, (b) iontophoresis, (c) carriers or vehicles which are compounds that modify the chemical properties of either the stratum corneum, or the pharmaceutical, and (d) sonophoresis which involves modifying the barrier function of stratum corneum by ultrasound. A cream containing lidocaine is commonly used, especially in pediatric patients, but needs to be applied for up to 60 minutes, and anesthesia is produced to a depth of only about 4 mm. The lack of lidocaine penetration is a consequence of the barrier function of the stratum corneum. Inherent problems with iontophoresis include the complexity of the delivery system, cost, and unknown toxicology of prolonged exposure to electrical current. Additionally, the use of carriers or vehicles involves additional compounds which might modify the pharmacokinetics of the pharmaceutical of interest or are irritating.

Thus, a need exists for a technique to remove fluids, gases or other biomolecules or to administer anesthetics or other pharmaceuticals which does not require a sharp instrument. The method and apparatus disclosed herein fulfill this need and obviate the need for the disposal of contaminated instruments, thereby reducing the risk of infection.

Lasers have been used in recent years as a very efficient precise tool in a variety of surgical procedures. Among potentially new sources of laser radiation, the rare-earth elements are of major interest for medicine. One of the most promising of these is a YAG (yttrium, aluminum, garnet) crystal doped with erbium (Er) ions. With the use of this crystal, it is possible to build an erbium-YAG (Er:YAG) laser which can be configured to emit electromagnetic energy at a wavelength (2.94 microns) which is strongly absorbed by, among other things, water. When tissue, which consists mostly of water, is irradiated with radiation at or near this wavelength, energy is transferred to the tissue. If the intensity of the radiation is sufficient, rapid heating can result followed by vaporization of tissue. In addition, deposition of this energy can result in photomechanical disruption of tissue. Some medical uses of Er:YAG lasers have been described in the health-care disciplines of dentistry, gynecology and ophthalmology. See, e.g., Bogdasarov, B. V., et al., "The Effect of Er:YAG Laser Radiation on Solid and Soft Tissues," Preprint 266, Institute of General Physics, Moscow, 1987; Bol'shakov, E. N. et al., "Experimental Grounds for Er:YAG Laser Application to Dentistry," SPIE 1353:160–169, Lasers and Medicine (1989) (these and all other references cited herein are expressly incorporated by reference as if fully set forth in their entirety herein).

SUMMARY OF THE INVENTION

The present invention employs a laser to perforate or alter the skin of a patient so as to remove fluids, gases or other biomolecules or to administer anesthetics or other pharmaceuticals. Perforation or alteration is produced by irradiating the surface of the target tissue with a pulse or pulses of electromagnetic energy from a laser. Prior to treatment, the care giver properly selects the wavelength, energy fluence (energy of the pulse divided by the area irradiated), pulse temporal width and irradiation spot size so as to precisely perforate or alter the target tissue to a select depth and eliminate undesired damage to healthy proximal tissue.

According to one embodiment of the present invention, a laser emits a pulsed laser beam, focused to a small spot for the purpose of perforating or altering the target tissue. By adjusting the output of the laser, the laser operator can control the depth, width and length of the perforation or alteration as needed.

In another embodiment continuous-wave or diode lasers may be used to duplicate the effect of a pulsed laser beam. These lasers are modulated by gating their output, or, in the case of a diode laser, by fluctuating the laser excitation current in a diode laser. The overall effect is to achieve brief irradiation, or a series of brief irradiations, that produce the same tissue permeating effect as a pulsed laser. The term "modulated laser" is used herein to indicate this duplication of a pulsed laser beam.

The term, "perforation" is used herein to indicate the ablation of the stratum corneum to reduce or eliminate its barrier function. The term, "alteration" of the stratum corneum is used herein to indicate a change in the stratum corneum which reduces or eliminates the barrier function of the stratum corneum and increases permeability without ablating, or by merely partially ablating, the stratum corneum itself. A pulse or pulses of infrared laser radiation at a subablative energy of, e.g., 60 mJ (using a TRANS-MEDICA™ International, Inc. ("TRANSMEDICA™") Er:YAG laser with a beam of radiant energy with a wavelength of 2.94 microns, a 200 $\mu$s (microsecond) pulse, and a 2 mm spot size) will alter the stratum corneum. The technique may be used for transdermal drug delivery or for obtaining samples, fluids, gases or other biomolecules, from the body. Different wavelengths of laser radiation and energy levels less than or greater than 60 mJ may also produce the enhanced permeability effects without ablating the skin.

The mechanism for this alteration of the stratum corneum is not certain. It may involve changes in lipid or protein nature or function or be due to desiccation of the skin or mechanical alterations secondary to propagating pressure waves or cavitation bubbles. The pathway that topically applied drugs take through the stratum corneum is generally thought to be through cells and/or around them, as well as through hair follicles. The impermeability of skin to topically applied drugs is dependent on tight cell to cell junctions, as well as the biomolecular makeup of the cell membranes and the intercellular milieu. Any changes to either the molecules that make up the cell membranes or intercellular milieu, or changes to the mechanical structural integrity of the stratum corneum and/or hair follicles can result in reduced barrier function. It is believed that irradiation of the skin with radiant energy produced by the Er:YAG laser causes measurable changes in the thermal properties, as evidenced by changes in the Differential Scanning Calorimeter (DSC) spectra as well as the Fourier Transform Infrared (FTIR) spectra of the stratum corneum. Changes in DSC and FTIR spectra occur as a consequence of changes in molecules or macromolecular structure, or the environment around these molecules or structures. Without wishing to be bound to any particular theory, we can tentatively attribute these observations to changes in lipids, water and protein molecules in the stratum corneum caused by irradiation of molecules with electromagnetic radiation, both by directly changing molecules as well as by the production of heat and pressure waves which can also change molecules.

Both perforation and alteration change the permeability parameters of the skin in a manner which allows for increased passage of pharmaceuticals, as well as fluids, gases or other biomolecules, across the stratum corneum.

Accordingly, one object of the present invention is to provide a means for perforating or altering the stratum corneum of a patient in a manner that does not result in bleeding. For example, the perforation or alteration created at the target tissue is accomplished by applying a laser beam that penetrates through the stratum corneum layer or both the stratum corneum layer and the epidermis, thereby reducing or eliminating the barrier function of the stratum corneum. This procedure allows the administration of anesthetics or other pharmaceuticals, as well as the removal of fluids, gases or other biomolecules, through the skin. Moreover, this procedure allows drugs to be administered continually on an outpatient basis over long periods of time. The speed and/or efficiency of drug delivery is thereby enhanced for drugs which were either slow or unable to penetrate skin.

In another embodiment of this invention, pressure waves, plasma, and cavitation bubbles are created in or above the stratum corneum to increase the permeation of the compounds (e.g., pharmaceuticals) or fluid, gas or other biomolecule removal. This method may simply overcome the barrier function of intact stratum corneum without significant alteration or may be used to increase permeation or collection in ablated or altered stratum corneum. As described herein, pressure waves, plasma, and cavitation bubbles are produced by irradiating the surface of the target tissue, or material on the target tissue, with a pulse or pulses of electromagnetic energy from a laser. Prior to treatment, the care giver properly selects the wavelength, energy fluence (energy of the pulse divided by the area irradiated), pulse temporal width and irradiation spot size to create the pressure waves, plasma, or cavitation bubbles while limiting undesired damage to healthy proximal tissue.

A further object of this invention is to provide an alternative means for administering drugs that would otherwise be required to be taken through other means, such as orally or injected, thereby increasing patient compliance and decreasing patient discomfort.

An additional object of this invention is to allow the taking of measurements of various fluid constituents, such as glucose, or to conduct measurements of gases.

A further object of this invention is to avoid the use of sharps. The absence of a contaminated sharp will eliminate the risk of accidental injury and its attendant risks to health care workers, patients, and others that may come into contact with the sharp. The absence of a sharp in turn obviates the need for disposal of biologically hazardous waste. Thus, the present invention provides an ecologically sound method for administering anesthetics or other pharmaceuticals, as well as removing fluids, gases or other biomolecules.

In another embodiment a typical laser is modified to include a container unit. Such a container unit can be added to: (1) increase the efficiency in the collection of fluids, gases or other biomolecules; (2) reduce the noise created when the laser beam perforates the patient's tissue; and (3) collect the ablated tissue. The optional container unit is alternatively evacuated to expedite the collection of the released materials such as the fluids, gases or other biomolecules. The container can also be used to collect only ablated tissue. The noise created from the laser beam's interaction with the patient's skin may cause the patient anxiety. The optional container unit reduces the noise intensity and therefore alleviates the patient's anxiety and stress. The container unit also minimizes the risk of cross-contamination and guarantees the sterility of the collected sample. The placement of the container unit in the use of this invention is unique in that it covers the tissue being irradiated, at the time of irradiation by the laser beam, and is therefore able to collect the fluid, gas or other biomolecule samples and/or ablated tissue as the perforation or alteration occurs. The container unit may also be modified for the purpose of containing materials, such as drugs, which may be applied before, simultaneously or shortly after irradiation.

A typical laser used for this invention requires no special skills to use. It can be small, light-weight and can be used with regular or rechargeable batteries. The greater the laser's portability and ease of use, the greater the utility of this invention in a variety of settings, such as a hospital room, clinic, or home.

Safety features can be incorporated into the laser that require that no special safety eyewear be worn by the operator of the laser, the patient, or anyone else in the vicinity of the laser when it is being used.

BRIEF DESCRIPTION OF THE DRAWINGS

The present invention may be better understood and its advantages appreciated by those skilled in the art by referring to the accompanying drawings wherein:

FIG. 12 shows an elastomeric mount for a solid state laser crystal element with optional mirrored surfaces applied to each end of the element.

FIG. 13 shows an example of a crystal rod with matte finish around the full circumference of the entire rod.

FIG. 14 shows an example of a crystal rod with matte finish around the full circumference of two-thirds of the rod.

FIG. 15 shows an example of a crystal rod with matte stripes along its longitudinal axis.

FIG. 16 shows a cross-section of a crystal laser rod element surrounded by a material having an index of refraction greater than the index of refraction of the rod.

FIGS. 17A–17G show various examples of a container unit.

FIGS. 19A and 19B show examples of a container unit in use with a laser.

FIG. 20 shows an example of a lens with a mask.

DETAILED DESCRIPTION

Figure 1:
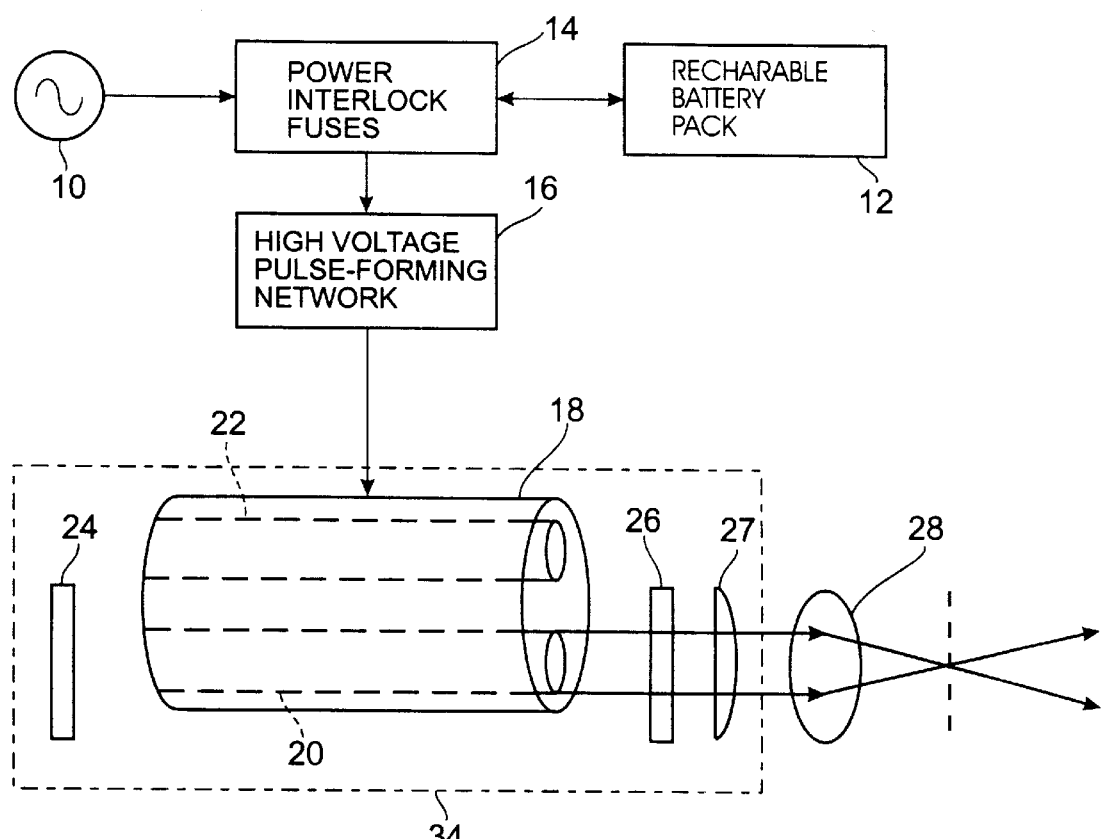
FIG. 1 shows a laser with its power source, high voltage pulse-forming network, flashlamp, lasing rod, mirrors, housing and focusing lens.

This invention provides a method for perforating or altering skin for either the sampling of fluids, gases or other biomolecules or the administration of anesthetics or other pharmaceuticals. The invention utilizes a laser beam, specifically focused, and lasing at an appropriate wavelength, to create small perforations or alterations in the skin of a patient. In a preferred embodiment, the laser beam has a wavelength between about 0.2 and 10 microns. More preferably, the wavelength is between about 1.5 and 3.0 microns. Most preferably the wavelength is about 2.94 microns. In one embodiment, the laser beam is focused with a lens to produce an irradiated spot on the skin with a size of approximately 0.5 microns–5.0 cm diameter. Optionally, the spot can be slit-shaped, with a width of about 0.05–0.5 mm and a length of up to 2.5 mm.

The caregiver may consider several factors in defining the laser beam, including wavelength, energy fluence, pulse temporal width and irradiation spot-size. In a preferred embodiment, the energy fluence is in the range of 0.03–100,000 J/cm$^2$. More preferably, the energy fluence is in the range of 0.03–9.6 J/cm$^2$. The beam wavelength is dependent in part on the laser material, such as Er:YAG. The pulse temporal width is a consequence of the pulse width produced by, for example, a bank of capacitors, the flashlamp, and the laser rod material. The pulse width is optimally between 1 fs (femtosecond) and 1,000 µs.

According to the method of the present invention the perforation or alteration produced by the laser need not be produced with a single pulse from the laser. In a preferred embodiment the caregiver produces a perforation or alteration through the stratum corneum by using multiple laser pulses, each of which perforates or alters only a fraction of the target tissue thickness.

To this end, one can roughly estimate the energy required to perforate or alter the stratum corneum with multiple pulses by taking the energy in a single pulse, and dividing by the number of pulses desirable. For example, if a spot of a particular size requires 1 J of energy to produce a perforation or alteration through the entire stratum corneum, then one can produce a qualitatively similar perforation or alteration using ten pulses, each having 1/10th the energy. Because it is desirable that the patient not move the target tissue during the irradiation (human reaction times are on the order of 100 ms or so), and that the heat produced during each pulse not significantly diffuse, in a preferred embodiment the pulse repetition rate from the laser should be such that complete perforation is produced in a time of less than 100 ms. Alternatively, the orientation of the target tissue and the laser can be mechanically fixed so that changes in the target location do not occur during the longer irradiation time.

To penetrate the skin in a manner which does not induce much if any blood flow, skin is perforated or altered through the outer surface, such as the stratum corneum layer, but not as deep as the capillary layer. The laser beam is focussed precisely on the skin, creating a beam diameter at the skin in the range of 0.5 microns–5.0 cm. The width can be of any size, being controlled by the anatomy of the area irradiated and the desired permeation rate of the pharmaceutical to be applied, or fluid, gas or other biomolecule to be removed. The focal length of the focussing lens can be of any length, but in one embodiment it is 30 mm.

By modifying wavelength, pulse length, energy fluence (which is a function of the laser energy output (in Joules) and size of the beam at the focal point (cm$^2$)), and irradiation spot size, it is possible to vary the effect on the stratum corneum between ablation (perforation) and non-ablation or partial ablation (alteration). Both ablation and non-ablative alternation of the stratum corneum result in enhanced permeation of subsequently applied pharmaceuticals, or removal of fluids, gases or other biomolecules.

For example, by reducing the pulse energy while holding other variables constant, it is possible to change between ablative and non-ablative tissue-effect. Using the TRANS-MEDICA™ Er:YAG laser, which has a pulse length of about 300 µs, with a single pulse or radiant energy and irradiating a 2 mm spot on the skin, a pulse energy above approximately 100 mJ causes ablation, while any pulse energy below approximately 100 mJ causes non-ablative alteration to the stratum corneum. Optionally, by using multiple pulses, the threshold pulse energy required to enhance pharmaceutical delivery is reduced by a factor approximately equal to the number of pulses.

Alternatively, by reducing the spot size while holding other variables constant, it is also possible to change between ablative and non-ablative tissue-effect. For example, halving the spot area will result in halving the energy required to produce the same effect. Irradiations down to 0.5 microns can be obtained, for example, by coupling the radiant output of the laser into the objective lens of a microscope objective (e.g. as available from Nikon, Inc., Melville, N.Y.). In such a case, it is possible to focus the beam down to spots on the order of the limit of resolution of the microscope, which is perhaps on the order of about 0.5 microns. In fact, if the beam profile is Gaussian, the size of the affected irradiated area can be less than the measured beam size and can exceed the imaging resolution of the microscope. To non-ablatively alter tissue in this case, it would be suitable to use a 3.2 J/cm$^2$ energy fluence, which for a half-micron spot size, would require a pulse energy of about 5 nJ. This low a pulse energy is readily available from diode lasers, and can also be obtained from, for example, the Er:YAG laser by attenuating the beam with an absorbing filter, such as glass.

Optionally, by changing the wavelength of radiant energy while holding the other variables constant, it is possible to change between an ablative and non-ablative tissue-effect. For example, using Ho:YAG (holmium: YAG; 2.127 microns) in place of the Er:YAG (erbium: YAG; 2.94 microns) laser, would result in less absorption of energy by the tissue, creating less of a perforation or alteration.

Picosecond and femtosecond pulses produced by lasers can also be used to produce alteration or ablation in skin. This can be accomplished with modulated diode or related microchip lasers, which deliver single pulses with temporal widths in the 1 femtosecond to 1 ms range. (See D. Stern et al., "Corneal Ablation by Nanosecond, Picosecond, and Femtosecond Lasers at 532 and 625 nm," Corneal Laser Ablation, vol. 107, pp. 587–592 (1989), incorporated herein by reference, which discloses the use of pulse lengths down to 1 femtosecond).

Figure 11:
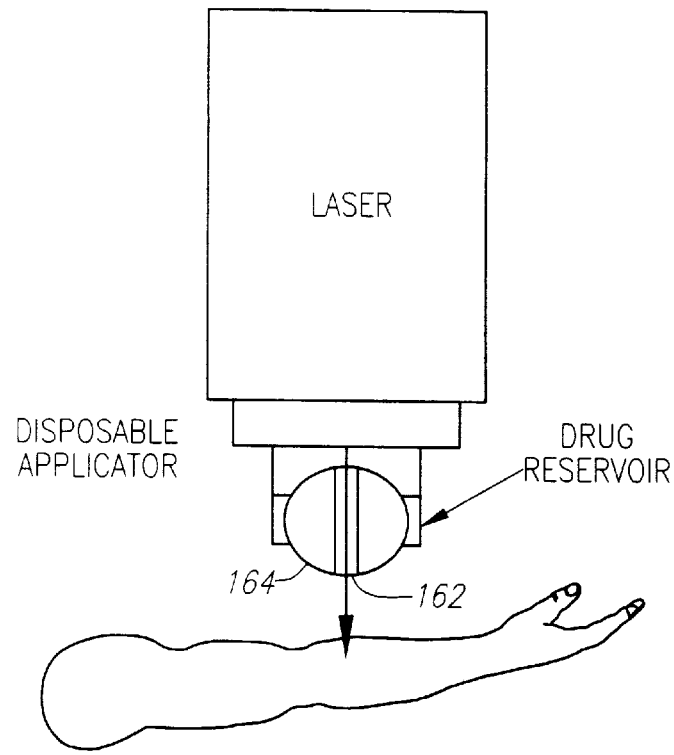
FIG. 11 shows a roll-on device for the delivery of anesthetics or pharmaceuticals.

According to one embodiment of the present invention, the anesthetic or pharmaceutical can be administered immediately after laser irradiation. Two embodiments of this invention incorporate an atomizer (FIG. 18) or a roll-on device (FIG. 11). In the case of a roll-on device, the laser beam propagates through hole 162 incorporated in ball 164 of the roll-on device. In the alternative, the roll-on device can be positioned adjacent to the path of the laser beam through the disposable applicator. After irradiation, the roll-on device is rolled over the irradiated site, thereby administering the desired anesthetic or pharmaceutical. In the case of an atomizer, the anesthetic is administered from a drug reservoir 166 through the use of compressed gas. After irradiation, a cylinder 168 containing compressed gas (such as, for example, carbon dioxide) is triggered to spray a set amount of anesthetic or pharmaceutical over the irradiated site.

Alternatively, it would be beneficial to apply positive pressure to a drug reservoir thereby pushing the drug into the skin, or negative pressure in a collection reservoir thus enhancing the diffusion of analytes out of the skin. Ambient atmospheric pressure is 760 mm Hg, or 1 atmosphere. Because of hydrostatic pressure in a standing individual, the relative pressure difference in the head may be 10 mm Hg below a reference value taken at the level of the neck, and 90 mm Hg higher in the feet. The arms may be between 8 and 35 mm Hg. Note also that because of the beating heart, a dynamic pressure (in a normal, healthy individual) of between 80–120 mm Hg is in the circulation. Thus, to permeate a drug through the skin (say in the arm), a positive pressure of greater than about 760 mm+35 mm Hg would be suitable. A pressure just slightly over 1 atmosphere would be suitable to enhance drug permeation, and yet would not enhance diffusion into the blood stream because of the dynamic pressures in the blood stream. A higher pressure might beneficially enhance diffusion into the blood stream. However, extended pressures much greater than perhaps 5 or so atmospheres for extended times might actually produce side effects.

In another embodiment of the present invention, an ink jet or mark is used for marking the site of irradiation. The irradiated sites are often not easily visible to the eye, consequently the health care provider may not know exactly where to apply the anesthetic or pharmaceutical subsequent to laser irradiation. This invention further provides techniques to mark the skin so that the irradiation site is apparent. For example, an ink-jet (analogous to those used in ink-jet printers) can be engaged prior to, during or immediately after laser irradiation. Additionally, a circle can be marked around the ablation site, or a series of lines all pointing inward to the ablation site can be used. Alternatively, the disposable safety-tip/applicator can be marked on the end (the end that touches up against the skin of the patient) with a pigment. Engaging the skin against the applicator prior to, during, or immediately after lasing results in a mark on the skin at the site of irradiation.

Figure 42:
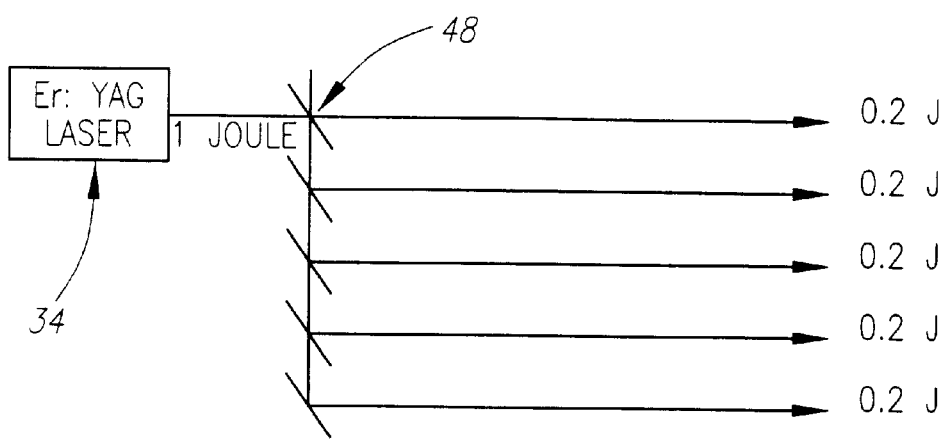
FIG. 42 shows an example of a beam splitter suitable for making simultaneous irradiation sites.
Figure 43:
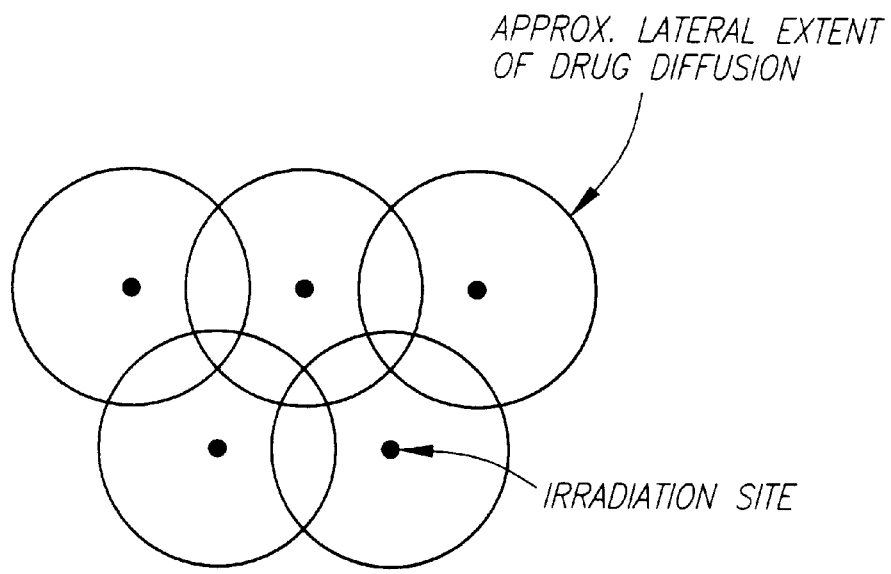
FIG. 43 shows one possible pattern of perforation or alteration sites using a beam splitter.

For certain purposes, it is useful to create multiple perforations or alterations of the skin simultaneously or in rapid sequence. To accomplish this, a beam-splitter can optionally be added to the laser, or a rapidly pulsing laser, such as a diode or related microchip lasers, may be used. Multiple irradiated sites, created simultaneously or sequentially, would result in an increased uptake of drugs as compared to a single irradiation site (i.e. an increase in uptake proportional to the total number of ablated sites). An example of a beam splitter 48 suitable for making simultaneous irradiation sites for use with a laser can be found in FIG. 42. Any geometric pattern of spots can be produced on the skin using this technique. Because the diffusion into skin of topically applied drugs can be approximated as symmetric, a beneficial pattern of irradiation spots for local drug delivery (such that a uniform local concentration would result over as wide an area as possible) would be to position each spot equidistant from each other in a staggered matrix pattern (FIG. 43).

Alternatively, multiple irradiation sites, or an irradiated area of arbitrary size and shape, could be produced with use of a scanner. For example, oscillating mirrors which reflect the beam of laser radiant energy can operate as a scanner.

For application of the laser device for anesthetic or pharmaceutical delivery, as well as fluid, gas or other biomolecule removal, the laser is manipulated in such a way that a portion of the patient's skin is positioned at the site of the laser focus within the applicator. For perforations or alterations for the delivery of anesthetics and other pharmaceuticals, as well as fluid, gas or other biomolecule removal, a region of the skin which has less contact with hard objects or with sources of contamination is preferred, but not required. Examples are skin on the arm, leg, abdomen or back. Optionally, the skin heating element is activated at this time in order to reduce the laser energy required for altering or ablating the stratum corneum.

Figure 2:
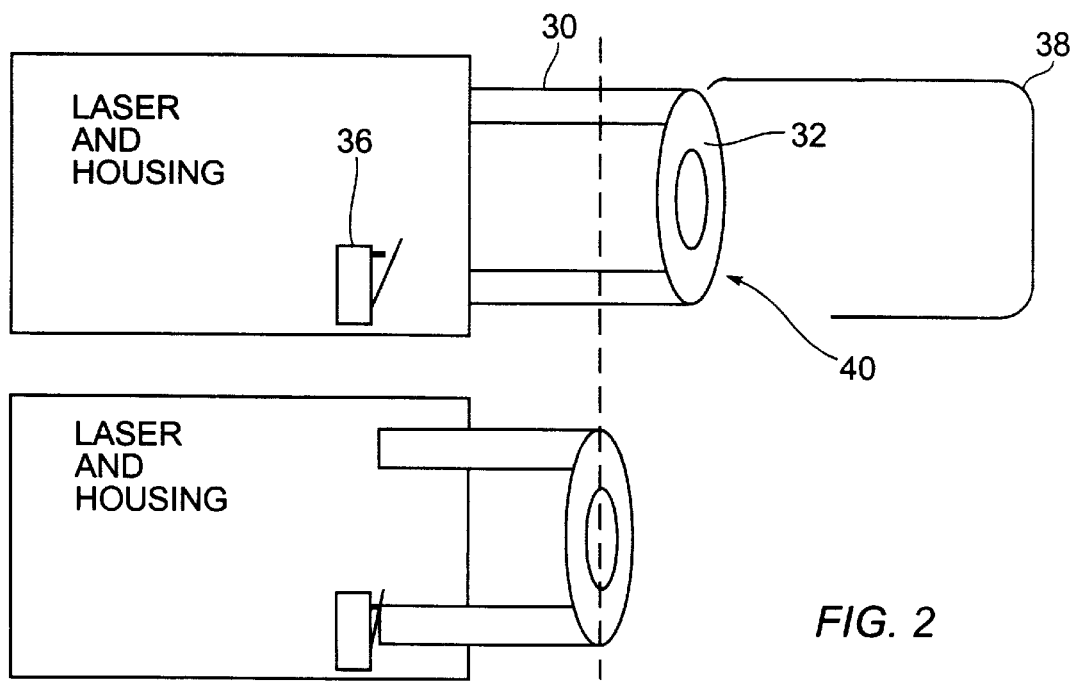
FIG. 2 shows an optional spring-loaded interlock and optionally heated applicator.

Preferably a holder is provided with a hole coincident with the focal plane of the optical system. Optionally, as shown in FIG. 2, a spring-loaded interlock 36 can be attached to the holder, so that when the patient applies a small amount of pressure to the interlock, to recess it to the focal point, a switch is closed and the laser will initiate a pulse of radiation. In this setup, the focal point of the beam is not in line with the end of the holder until that end is depressed. In the extremely unlikely event of an accidental discharge of the laser before proper positioning of the tissue at the end of the laser applicator, the optical arrangement will result in an energy fluence rate that is significantly low, thus causing a negligible effect on unintentional targets.

The method of this invention may be enhanced by using a laser of a wavelength that is specifically absorbed by the skin components of interest (e.g., water, lipids or protein) which strongly affect the permeation of the skin tissues. However, choosing a laser that emits a strongly absorbed wavelength is not required. Altering the lipids in stratum corneum may allow enhanced permeation while avoiding the higher energies that are necessary to affect the proteins and water.

It would be beneficial to be able to use particular lasers other than the Er:YAG for stratum corneum ablation or alteration. For example, laser diodes emitting radiant energy with a wavelength of 810 nm (0.8 microns) are inexpensive, but such wavelength radiation is only poorly absorbed by tissue. In a further embodiment of this invention, a dye is administered to the skin surface, either by application over intact stratum corneum, or by application over an Er:YAG laser treated site (so the that deep dye penetration can occur), that absorbs such a wavelength of radiation. For example, indocyanine green (ICG), which is a harmless dye used in retina angiography and liver clearance studies, absorbs maximally at 810 nm when in plasma (Stephen Flock and Steven Jacques, "Thermal Damage of Blood Vessels in a Rat Skin-Flap Window Chamber Using Indocyanine Green and a Pulsed Alexandrite Laser A Feasibility Study," Laser Med. Sci. 8, 185–196, 1993). This dye, when in stratum corneum, is expected to absorb the 810 nm radiant energy from a diode laser (e.g. a GaAlAs laser) thereby raising the temperature of the tissue, and subsequently leading to ablation or molecular changes resulting in reduced barrier function.

Alternatively, it is possible to chemically alter the optical properties of the skin to enhance subsequent laser radiant energy absorption without chemicals actually being present at the time of laser irradiation. For example, 5-aminolevulinic acid (5-ALA) is a precursor to porphyrins, which are molecules involved in hemoglobin production and behavior. Porphyrins are strong absorbers of light. Administration of 5-ALA stimulates production of porphyrins in cells, but is itself consumed in the process. Subsequently, there will be enhanced absorption of radiant energy in this tissue at wavelengths where porphyrins absorb (e.g., 400 nm or 630 nm).

Another way to enhance the absorption of radiant energy in stratum corneum without the addition of an exogenous absorbing compound is to hydrate the stratum corneum by, for example, applying an occlusive barrier to the skin prior to laser irradiation. In this situation, the water produced within the body itself continues to diffuse through the stratum corneum and propagate out through pores in the skin, but is prevented from evaporating by the occlusive barrier. Thus, the moisture is available to further saturate the stratum corneum. As the radiant energy emitted by the Er:YAG laser is strongly absorbed by water, this process would increase the absorption coefficient of the stratum corneum, and so less energy would be required to induce the alterations or ablations in the stratum corneum necessary for enhanced topical drug delivery.

Additionally, the laser ablated site eventually heals as a result of infiltration of keratinocytes and keratin (which takes perhaps two weeks to complete), or by the diffusion of serum up through the ablated sites which form a clot (or eschar) which effectively seals the ablated site. For long term topical delivery of drugs, or for multiple sequential administrations of topical drugs, it would be beneficial to keep the ablated site open for an extended length of time.

Thus, in an additional embodiment of this invention, the ablated or non-ablated site is kept open by keeping the area of irradiation moist. This is accomplished by minimizing contact of air with the ablated site and/or providing fluid to keep the ablated site moist and/or biochemically similar to stratum corneum. The application of a patch (containing, for example, an ointment such as petroleum jelly or an ointment containing hydrocortisone) over the site would help to keep it open. A hydrogel patch would also serve to provide the necessary moisture. Additionally, cytotoxic drugs such as cisplatin, bleomycin, doxurubicin, and methotrexate, for example, topically applied in low concentrations would locally prevent cellular infiltration and wound repair. Furthermore, application of vitamin C (ascorbic acid), or other known inhibitors of melanin production, following irradiation, would help to prevent additional skin coloration in the area following treatment.

Pressure Wave to Enhance the Permeability of the Stratum Corneum or other Membranes In another embodiment of the present invention, a pressure gradient is created at the ablated or altered site to force substances through the skin. This technique can be used for the introduction of compounds (e.g., pharmaceuticals) into the body.

When laser radiant energy is absorbed by tissue, expansion (due to heating) and/or physical movement of tissue (due to heating or non-thermal effects such as spallation) takes place. These phenomena lead to production of propagating pressure waves, which can have frequencies in the acoustic (20 Hz to 20,000 Hz) or ultrasonic (>20,000 Hz) region of the pressure wave spectrum. For example, Flock et al. (Proc SPIE Vol. 2395, pp. 170–176, 1995) show that when a 20 ns pulse from a Q-switched frequency-doubled Nd:YAG laser is impacted on blood, propagating transient high pressure waves form. These pressure waves can be spectrally decomposed to show that they consist of a spectrum of frequencies, from about 0 to greater than 4 MHz. The high pressure gradient associated with these kinds of compressional-type pressure waves can be transformed into tension-type or stress waves which can "tear" tissue apart in a process referred to as "spallation".

Figure 44:
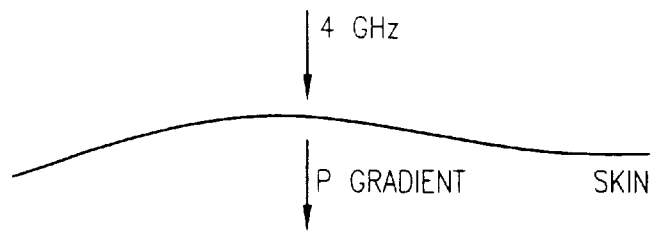
FIG. 44 shows a pressure gradient created in the stratum corneum.
Figure 47:
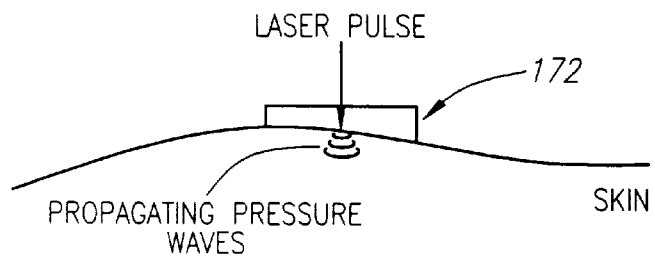
FIG. 47 shows a propagating pressure wave created at the skin surface with a transparent, or partially transparent, optic located on the skin.

The absorption of propagating pressure waves by tissue is a function of the tissue type and frequency of wave. Furthermore, the speed of these pressure waves in non-bone tissue is approximately 1400–1600 m/sec. Using these observations, a pressure gradient in tissue can be created, directed either into the body or out of the body, using pulsed laser radiant energy. To efficiently create pressure waves with a pulsed laser, the pulse duration needs to be less than the time it takes for the created heat to diffuse out of the region of interest. The effect is qualitatively equivalent to the effects of ultrasound on tissue. The attenuation coefficient for sound propagation in tissue increases approximately linearly with frequency (see, for example, J. Havlice and J. Taenzer, "Medical Ultrasound Imaging: An Overview of Principles and Instrumentation", Proc. IEEE 67, 620–641, 1979), and is approximately 1 dB/cm/MHz (note that a 20 decibel (dB) intensity difference is equivalent to a factor of 10 in relative intensity). The thickness of the stratum corneum is about 25 microns and the epidermis is about 200 microns. Thus, the frequency that is attenuated by 10 dB when propagating through the stratum corneum is 10 dB/(1 dB/cm/MHz*0.0025cm), or 4 GHz. Similarly, as strongly absorbed radiant energy produced by a pulsed laser (say pulsed at 4 GHz) will produce propagating pressure waves of a similar frequency as the pulse repetition rate, it is possible to selectively increase the pressure in the stratum corneum or upper layers of skin as compared to the lower layers, thus enhancing the diffusive properties of topically applied drug (see, e.g., FIG. 44). A transparent, or nearly transparent, optic 172, as shown in FIG. 47, can be placed on the surface of the skin to contain the backward inertia of the propagating pressure wave or ablated stratum corneum.

Figure 45:
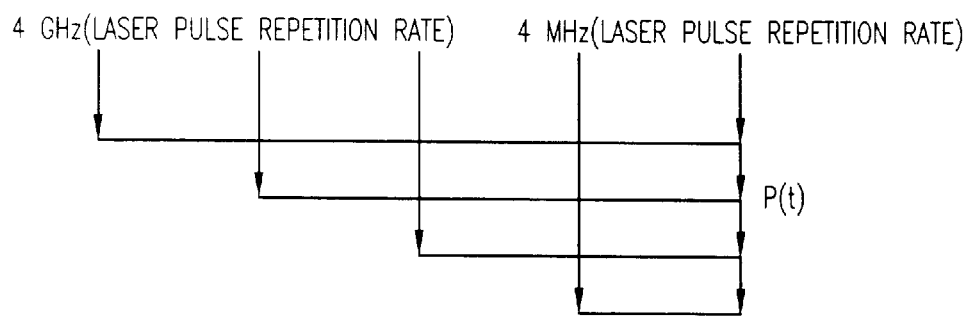
FIG. 45 is a schematic of modulating the pulse repetition frequency of radiant energy from high (4 GHz) to low (4 MHz).

In an additional embodiment, as shown in FIG. 45, by modulating the pulse repetition frequency of the radiant energy from high to low, it is possible to create transient pressure fields that can be designed to be beneficial for enhancing the diffusive properties of a topically applied pharmaceutical.

The high-frequency propagating pressure waves can also be produced from a single laser pulse. When tissue absorbs a brief pulse of laser irradiation, pressure waves with a spectrum of frequencies result. Some of these frequencies will propagate into lower layers in the skin, thus it may be possible to set up a reverse pressure gradient (more pressure below and less superficially) in order to enhance the diffusion of biomolecules out of the body, effectively "pumping" them through the skin.

Acoustic waves and/or spallation are believed to occur during the use of the TRANSMEDICA™ Er:YAG laser in ablation of stratum corneum for drug delivery or perforation, since the 2.94 micron radiant energy is absorbed in about 1 micron of tissue, yet the tissue ablation can extend much deeper.

A continuous-wave laser can also be used to create pressure waves. A continuous-wave laser beam modulated at 5–30 MHz can produce 0.01–5 W/cm$^2$ pressure intensities in tissue due to expansion and compression of sequentially heated tissue (for example, a Q-switched Er:YAG laser (40 ns pulse) at 10 mJ and focussed to a spot size of 0.05 cm, with a pulse repetition rate of 5–30 MHz, would produce in stratum corneum a stress of about 3750 bars, or 0.025 W/cm$^2$). It takes a few hundred bars to cause transient permeability of cells. With this laser it requires about 0.01 W/cm$^2$ of continuous pressure wave energy to provide effective permeation of skin.

Figure 49:
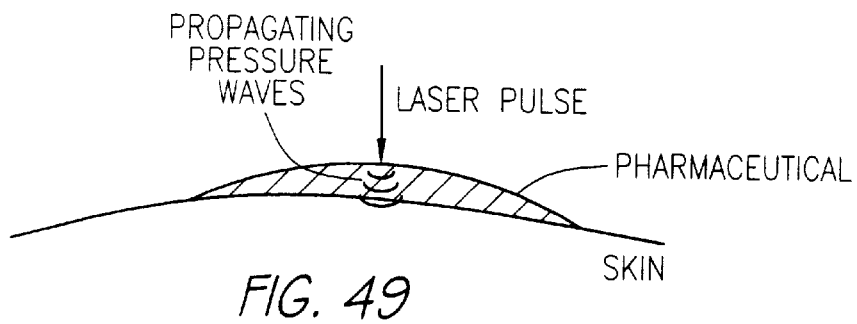
FIG. 49 shows a propagating pressure wave created in the applied pharmaceutical.

In an additional embodiment, pressure waves are induced on the topically applied pharmaceutical. The propagation of the wave towards the skin will carry some of the pharmaceutical with it (see, e.g., FIG. 49).

Figure 46:
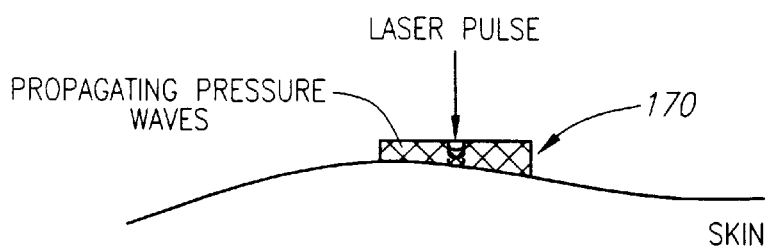
FIG. 46 shows a propagating pressure wave created in an absorbing material located on the skin.
Figure 48:
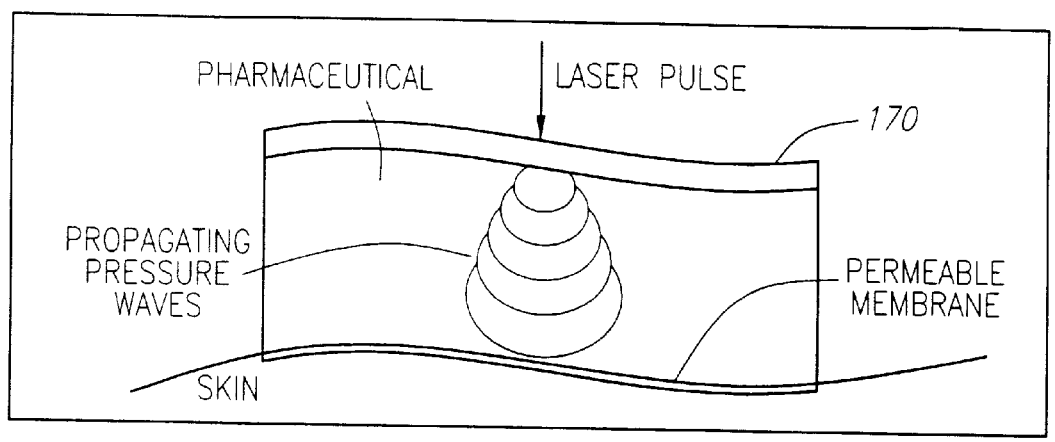
FIG. 48 shows a propagating pressure wave created in an absorbing material on the applied pharmaceutical.

In a further embodiment, pressure waves are induced on an absorbing material 170 placed over the topically applied pharmaceutical (see, e.g., FIG. 48). Preferably this material is a thin film of water, however, it can be created in any liquid, solid or gas located over the topically applied pharmaceutical. The propagation of the wave towards the skin will carry some of the pharmaceutical with it. Additionally, pressure waves can be induced on an absorbing material 170 (preferably a thin film of water, however, it can be created in any liquid, solid or gas) placed over the target tissue (see, e.g., FIG. 46). The propagation of the wave towards the skin will increase the permeability of the stratum corneum. Subsequent to the formation of these pressure waves, the desired pharmaceutical can be applied.

Figure 50:
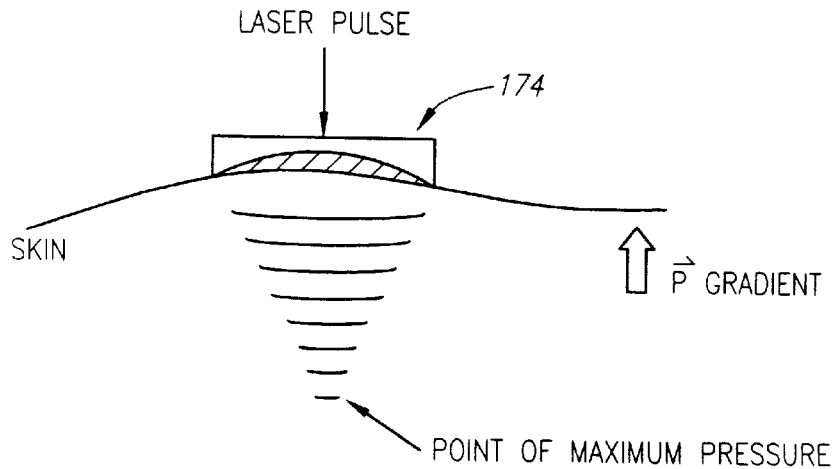
FIG. 50 shows the creation of pressure waves in tissue converging to a focal point.

In another embodiment, pressure gradients can be used to remove fluids, gases or other biomolecules from the body. This can be accomplished by focusing a beam of radiant energy down to a small volume at some point within the tissue. The resulting heating leads to pressure wave intensities (which are proportional to the degree of heating) that will be greater near the focal point of the radiant energy, and less near the surface. The consequence of this is a pressure gradient directed outwards thus enhancing the removal of fluids, gases or other biomolecules. Alternatively, propagating pressure waves created at the surface of the skin can be focused to a point within the tissue. This can be done, for example, by using a pulsed laser to irradiate a solid object 174 above the skin, which by virtue of its shape, induces pressure waves in the tissue which converges to the focal point (see, e.g., FIG. 50). Again, the consequence of this is a pressure gradient directed outwards thus enhancing the removal of fluids, gases or other biomolecules.

The pressure waves described can be created after perforation or alteration of the stratum corneum has taken place. Alternatively, pressure waves can be used as the sole means to increase the diffusive properties of compounds trough the skin or the removal of fluids, gases or other biomolecules.

The pressure waves described can be created after perforation or alteration of the stratum corneum has taken place. Alternatively, pressure waves can be used as the sole means to increase the diffusive properties of pharmaceuticals.

Creation of Cavitation Bubbles to Increase Stratum Corneum Permeability

Cavitation bubbles, produced subsequent to the target tissues perforation or alteration, can be used to enhance the diffusive properties of a topically applied drug. While production of cavitation bubbles within the tissue is known (See, for example, R. Ensenaliev et al., "Effect of Tensile Amplitude and Temporal Characteristics on Threshold of Cavitation-Driven Ablation," Proc. SPIE vol. 2681, pp 326–333, (1996)), for the present invention, cavitation bubbles are produced in a material on or over the surface of the skin so that they propagate downwards (as they do because of conservation of momentum) and impact on the stratum corneum, thereby reducing the barrier function of the skin. The cavitation bubbles can be created in an absorbing material 170 located on or over the skin.

Cavitation has been seen to occur in water at –8 to –100 bars, (Jacques et al., Proc. SPIE vol. 1546, p. 284 (1992)). Thus, using a Q-switched Er:YAG laser (40 ns pulse) at 10 mJ and focussed to a spot size of 0.05 cm in a thin film of water on the skin, with a pulse repetition rate of 5–30 MHz, a stress of about 3750 bars, or 0.025 W/cm$^2$, is produced. This should generate the production of cavitation bubbles, which, when they contact the skin will cause mechanical and/or thermal damage thereby enhancing stratum corneum permeability.

In a preferred embodiment, the cavitation bubbles are produced in a thin film of water placed on or over the skin, however, any liquid or solid material can be used. Subsequent to production of the cavitation bubbles a pharmaceutical is applied to the affected tissue.

In an additional embodiment, cavitation bubbles are produced in the administered pharmaceutical subsequent to its application on the skin. Cavitation bubbles can also be produced in the stratum corneum itself before pharmaceutical application.

In a further embodiment, the target tissue is not perforated or altered before the production of cavitation bubbles, the cavitation bubbles' impact on the stratum corneum being the only method used to increase stratum corneum permeability.

Plasma Ablation to Increase Stratum Corneum Permeability

Plasma is a collection of ionized atoms and free electrons. It takes an extremely strong electric field or extremely high temperature to ionize atoms, but at the focus of an intense pulsed laser beam (>approx. $10^8$–$10^{10}$ W/cm$^2$), such electric fields can result. Above this energy fluence rate, high enough temperatures can result. What one sees when plasma is formed is a transient bright white cloud (which results from electrons recombining with atoms resulting in light emission at many different wavelengths which combine to appear to the eye as white). A loud cracking is usually heard when plasma is formed as a result of supersonic shock waves propagating out of the heated (>1000K) volume that has high pressures (perhaps >1000 atmospheres). Since plasma is a collection of hot energetic atoms and electrons, it can be used to transfer energy to other matter, such as skin. See Walsh J T, "Optical-Thermal Response of Laser-Irradiated Tissue," Chapter 25, pp. 865–902 (Plenum Press, NY 1995), incorporated by reference herein as if fully set forth in its entirety. For example, U.S. Pat. No. 5,586,981, issued to Hu, discloses the use of plasma to treat cutaneous vascular or pigmented lesions. The wavelength of the laser in Hu '981 is chosen such that the laser beam passes through the epidermal and dermal layers of skin and the plasma is created within the lesion, localizing the disruption to the targeted lesion.

A plasma can also be used to facilitate diffusion through the stratum corneum. In one embodiment of the present invention, plasma is produced above the surface of the skin whereupon a portion of the plasma cloud will propagate outwards (and downwards) to the skin whereupon, ablation or tissue alteration will occur. Plasma can be created in a liquid, solid or gas that is placed on or over the skin, into which the laser beam is focussed. If the plasma is created in a material with an acoustic impedance similar to tissue (say, a fluid), then the resulting pressure waves would tend to transfer most of their energy to the skin. The plasma "pressure wave" behaves similarly to a propagating pressure wave in tissue. This is due to the fact that the impedance mismatch at the upper surface between air and solid/liquid material is high, and, furthermore, plasma, like ultrasonic energy, propagates poorly in low-density (i.e. air) media.

In another embodiment, plasma is produced within the stratum corneum layer. Because the energy fluence rate needed to produce the plasma is as high as approximately $10^8$ W/cm$^2$, selection of a wavelength with radiant energy that is strongly absorbed in tissue is not an important concern.

Important benefits in these embodiments are that (1) the optical absorption of material to produce plasma is not an important consideration, although the energy fluence rate required to produce the plasma is less when the irradiated material strongly absorbs the incident radiant energy, and (2) there are relatively inexpensive diode-pumped Q-switched solid state lasers that can produce the requisite radiant energy (such as are available from Cutting Edge Optronics, Inc., St, Louis, Mo.).

To obtain a peak energy fluence rate greater than or approximately equal to the plasma creation threshold of $10^8$ W/cm$^2$, using a pulse length of 300 $\mu$s (e.g. for the TRANSMEDICA™ Er:YAG laser, 1J for 300 $\mu$s), the pulse power is 3333 W, and the spot size needs to be 0.0065 mm. Alternatively, a small diode-pumped Q-switched laser can be used. Such lasers have pulse widths on the order of 10 ns, and, as such, the requisite spot size for producing plasma could be much larger.

Continuous-Wave (CW) Laser Scanning

It is possible, under machine and microprocessor control, to scan a laser beam (either continuous-wave or pulsed) over the target tissue, and to minimize or eliminate thermal damage to the epidermis or adjacent anatomical structures.

For example, a scanner (made up of electro-optical or mechanical components) can be fashioned to continually move the laser beam over a user-defined area. This area can be of arbitrary size and shape. The path for the scan could be spiral or raster. If the laser is pulsed, or modulated, then it would be possible to do a discrete random pattern where the scanning optics/mechanics directs the beam to a site on the skin, the laser lases, and then the scanning optics/mechanics directs the beam to a different site (preferable not adjacent to the first spot so that the skin has time to cool before an adjacent spot is heated up).

This scanning technique has been used before with copper-vapor lasers (in treating port-wine stains) and is in use with $CO_2$ lasers for the purpose of facial resurfacing. In the case of the former, the subepidermal blood vessels are targeted, while in the latter, about 100 microns of tissue is vaporized and melted with each laser pass.

Delivery of Anesthesia

A laser can be used to perforate or alter the skin through the outer surface, such as the stratum corneum layer, but not as deep as the capillary layer, to allow localized anesthetics to be topically administered. Topically applied anesthetics must penetrate the stratum corneum layer in order to be effective. Presently, compounds acting as drug carriers are used to facilitate the transdermal diffusion of some drugs. These carriers sometimes change the behavior of the drug, or are themselves toxic.

With the other parameters set, the magnitude of the laser pump source will determine the intensity of the laser pulse, which will in turn determine the depth of the resultant perforation or alteration. Therefore, various settings on the laser can be adjusted to allow perforation or alteration of different thicknesses of stratum corneum.

Optionally, a beam-dump can be positioned in such a way as not to impede the use of the laser for perforation or alteration of extremities. The beam-dump will absorb any stray electromagnetic radiation from the beam that is not absorbed by the tissue, thus preventing any scattered rays from causing damage. The beam-dump can be designed so as to be easily removed for situations when the presence of the beam-dump would impede the placement of a body part on the applicator.

This method of delivering anesthetic creates a very small zone in which tissue is irradiated, and only an extremely small zone of thermal necrosis. A practical round irradiation site can range from 0.1–5.0 cm in diameter, while a slit shaped hole can range from approximately 0.05–0.5 mm in width and up to approximately 2.5 mm in length, although other slit sizes and lengths can be used. As a result, healing is quicker or as quick as the healing after a skin puncture with a sharp implement. After irradiation, anesthetic can then be applied directly to the skin or in a pharmaceutically acceptable formulation such as a cream, ointment, lotion or patch.

Alternatively, the delivery zone can be enlarged by strategic location of the irradiation sites and by the use of multiple sites. For example, a region of the skin may be anesthetized by first scanning the desired area with a pulsing laser such that each pulse is sufficient to cause perforation or alteration. This can be accomplished with modulated diode or related microchip lasers, which deliver single pulses with temporal widths in the 1 femtosecond to 1 ms range. (See D. Stern et al., "Corneal Ablation by Nanosecond, Picosecond, and Femtosecond Lasers at 532 and 625 nm," Corneal Laser Ablation, vol. 107, pp. 587–592 (1989), incorporated herein by reference, which discloses the use of pulse lengths down to 1 femtosecond). Anesthetic (e.g., 10% lidocaine) would then be applied over the treated area to achieve a zone of anesthesia.

The present method can be used for transport of a variety of anesthetics. These anesthetics are different in their system and local toxicity, degree of anesthesia produced, time to onset of anesthesia, length of time that anesthesia prevails, biodistribution, and side effects. Examples of local anesthetic in facial skin-resurfacing with a laser can be found in Fitzpatrick R. E., Williams B. Goldman M. P., "Preoperative Anesthesia and Postoperative Considerations in Laser Resurfacing," Semin. Cutan. Med. Surg. 15(3):170–6, 1996. A partial list consists of: cocaine, procaine, mepivacaine, etidocaine, ropivacaine, bupivacaine, lidocaine, tetracain, dibucaine, prilocaine, chloroprocaine, hexlcaine, fentanly, procainamide, piperocaine, MEGX (des-ethyl lidocaine) and PPX (pipecolyl xylidine). A reference on local anesthetic issues can be found in Rudolph de Jong, "Local Anesthetics," Mosby-Year Book: St Louis, 1994.

Delivery of Pharmaceuticals

The present method can also be used to deliver pharmaceuticals in a manner similar to the above described delivery of anesthesia. By appropriate modification of the power level, and/or the spot size of the laser beam, perforations or alterations can be made which do not penetrate as deep as the capillary layer. These perforations or alterations can be made through only the outer surfaces, such as the stratum corneum layer or both the stratum corneum. layer and the epidermis. Optionally an optical beam-splitter or multiply pulsed laser can be employed so that either single or multiple perforations or alterations within a desired area can be made. After perforation or alteration, the pharmaceutical can be applied directly to the skin or in a pharmaceutically acceptable formulation such as a cream, ointment, lotion or patch.

The present method can be used for transport of a variety of systemically acting pharmaceutical substances. For example nitroglycerin and antinauseants such as scopolamine; antibiotics such as tetracycline, streptomycin, sulfa drugs, kanamycin, neomycin, penicillin, and chloramphenicol; various hormones, such as parathyroid hormone, growth hormone, gonadotropins, insulin, ACTH, somatostatin, prolactin, placental lactogen, melanocyte stimulating hormone, thyrotropin, parathyroid hormone, calcitonin, enkephalin, and angiotensin; steroid or non-steroid anti-inflammatory agents, and systemic antibiotic, antiviral or antifungal agents.

Delivery of Locally Acting Pharmaceuticals

Laser-assisted perforation or alteration provides a unique site for local uptake of pharmaceutical substances to a desired region. Thus, high local concentrations of a substance may be achieved which are effective in a region proximal to the irradiated site by virtue of limited dilution near the site of application. This embodiment of the present invention provides a means for treating local pain or infections, or for application of a substance to a small specified area, directly, thus eliminating the need to provide high, potentially toxic amounts systemically through oral or i.v. administration. Locally acting pharmaceuticals such as alprostadil (for example Caverject from Pharmacia & Upjohn), various antibiotics, antiviral or antifungal agents, or chemotherapy or anti-cancer agents, can be delivered using this method to treat regions proximal to the delivery site. Protein or DNA based biopharmaceutical agents can also be delivered using this method.

Immunization

As for delivery of pharmaceuticals, antigens derived from a virus, bacteria or other agent which stimulates an immune response can be administered through the skin for immunization purposes. The perforations or alterations are made through the outer layers of the skin, either singly or multiply, and the immunogen is provided in an appropriate formulation. For booster immunizations, where delivery over a period of time increases the immune response, the immunogen can be provided in a formulation which penetrates slowly through the perforations or alterations, but at a rate faster than possible through unperforated or unaltered skin.

This approach offers clinicians a new approach for immunizations by solving some of the problems encountered with other routes of administration (e.g. many vaccine preparations are not efficacious through oral or intravenous routes). Further, the skin is often the first line of defense for invading microbes and the immune response in the skin is partially composed of Immunoglobulin A (IgA) antibodies like that of the mucous membranes. Scientists have long sought ways to induce mucosal immunity using various vaccine preparations. Unfortunately they have been met with limited success because in order to generate an IgA response, vaccine preparations must be delivered to mucous membranes in the gut or sinuses which are difficult to reach with standard formulations. By immunizing intradermally, unique populations of antibodies may be generated which include IgA, a critical element of mucosal immunity. This laser-assisted intradermal method of antigen presentation thereby may be used as a means to generate IgA antibodies against invading organisms.

Delivery of Allergens

Traditional allergy testing requires the allergist to make multiple pricks on the patient's skin and apply specific allergens to make a determination regarding intradermal hypersensitivity. The method of this invention can be used to deliver allergens reproducibly for allergy testing. Multiple perforations or alterations can be made through the outer layer of the skin without penetrating to the capillary level. A variety of allergens can then be applied to the skin, as in a skin patch test. One of the benefits of this methodology is that the stratum corneum barrier function compromise (i.e. laser irradiation) is more consistent than pricks made with a sharp.

Delivery of Permeation Enhancers

Certain compounds may be used to enhance the permeation of substances into the tissues below perforated or ablated stratum corneum. Such enhancers include DMSO, alcohols and salts. Other compounds specifically aid permeation based on specific effects such as by increasing ablation or improving capillary flow by limiting inflammation (i.e. salicylic acid). The method of this invention can be used to deliver these permeation enhancers. Multiple or single perforations or alterations can be made through the outer layer of the skin without penetrating to the capillary level. Subsequently, a variety of permeation enhancers can be applied to the irradiated site, as in a skin patch.

Delivery of Anti-Inflammatory Drugs

Analgesics and other non-steroid anti-inflammatory agents, as well as steroid anti-inflammatory agents may be caused to permeate through perforated or altered stratum corneum to locally affect tissue within proximity of the irradiated site. For example, anti-inflammatory agents such as Indocin (Merck & Co.), a non-steroidal drug, are effective agents for treatment of rheumatoid arthritis when taken orally, yet sometimes debilitating gastrointestinal effects can occur. By administering such agents through laser-assisted perforation or alteration sites, these potentially dangerous gastrointestinal complications may be avoided. Further, high local concentrations of the agents may be achieved more readily near the site of irradiation as opposed to the systemic concentrations achieved when orally administered.

Drawing Fluids, Gases or Other Biomolecules

A laser can be used to perforate or alter the skin through the outer surface, such as the stratum corneum layer, but not as deep as the capillary layer, to allow the collection of fluids, gases or other biomolecules. The fluid, gas or other biomolecule can be used for a wide variety of tests. With the other parameters set, the magnitude of the laser pump source will determine the intensity of the laser pulse, which will in turn determine the depth of the resultant perforation or alteration. Therefore, various settings on the laser can be adjusted to allow penetration of different thicknesses of skin.

Optionally, a beam-dump can be positioned in such a way as not to impede the use of the laser for perforation or alteration of extremities. The beam-dump will absorb any stray electromagnetic radiation from the beam that is not absorbed by the tissue, thus preventing any scattered rays from causing damage. The beam-dump can be designed to be easily removed for situations when the presence of the beam-dump would impede the placement of a body part on the applicator.

This method of drawing fluids, gases or other biomolecule creates a very small zone in which tissue is irradiated, and only an extremely small zone of thermal necrosis. For example, a practical round hole can range from about 0.1–1 mm in diameter, while a slit shaped hole can range from about approximately 0.05–0.5 mm in width and up to approximately 2.5 mm in length. As a result, healing is quicker or as quick as the healing after a skin puncture with a sharp implement.

The fluid, gas or other biomolecule can be collected into a suitable vessel, such as a small test tube or a capillary tube, or in a container unit placed between the laser and the tissue as described above. The process does not require contact. Therefore, neither the patient, the fluid, gas or other biomolecule to be drawn, or the instrument creating the perforation or alteration is contaminated.

The technique of the present invention may be used to sample extracellular fluid in order to quantify glucose or the like. Glucose is present in the extracellular fluid in the same concentration as (or in a known proportion to) the glucose level in blood (e.g. Lonnroth P. Strindberg L. Validation of the "internal reference technique" for calibrating micro dialysis catheters in situ, Acta Physiological Scandinavica, 153(4):37580, 1995 Apr.).

Figure 27:
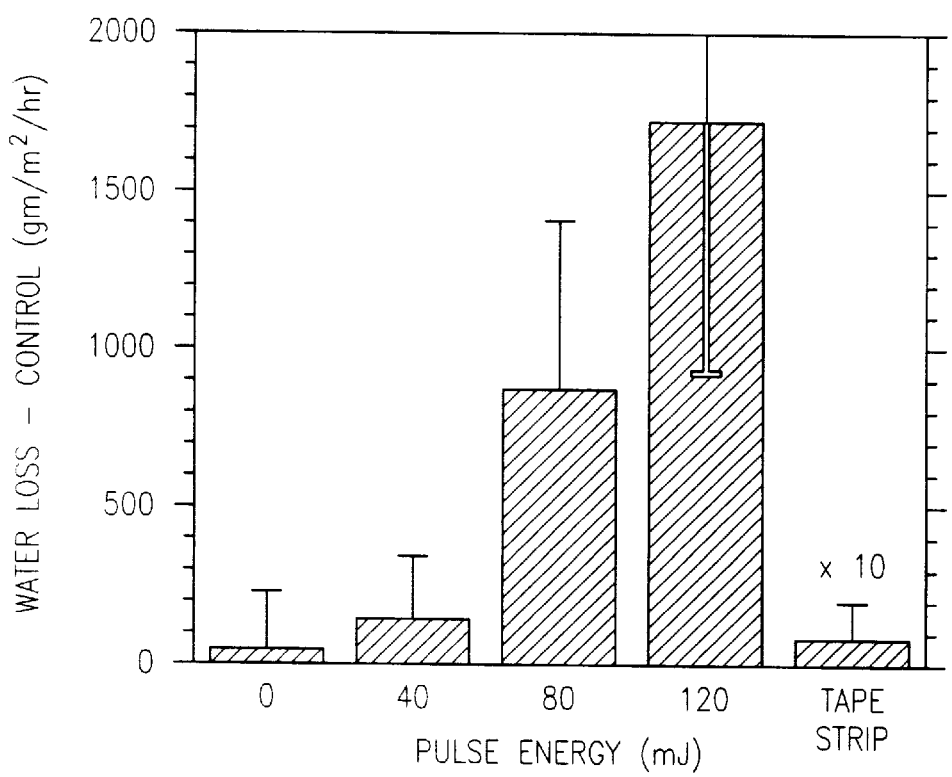
FIG. 27 shows laser pulse energy (J) versus water loss through human skin in vivo.

The perforation or alteration of the stratum corneum causes a local increase in the water loss through the skin (referred to as transepidermal water loss, or TEWL). As shown in FIG. 27, with increasing laser energy fluence ($J/cm^2$), there is a corresponding increase in water loss. The tape strip data is a positive control that proves that the measurement is indeed sensitive to increased skin water evaporation.

Two of the energies used in FIG. 27, 40 mJ and 80 mJ (1.27 and 2.55 $J/cm^2$) are non-ablative and therefore show that non-ablative energies allow the alteration of the barrier function of stratum corneum, thereby resulting in enhanced transepidermal water loss which can provide a diagnostic sample of extracellular fluid.

Besides glucose, other compounds and pathological agents also can be assayed in extracellular fluid. For example, HIV is present extracellularly and may be assayed according to the present method. The benefit to obtaining samples for HIV analysis without having to draw blood with a sharp that can subsequently contaminate the health-care provider is obvious. Additionally, the present invention can be used to employ lasers non-ablatively to reduce or eliminate the barrier properties of non-skin barriers in the human body, such as the blood-brain interface membranes, such as that positioned between the brains third ventricle and the hypothalamus, the sclera of the eye or any mucosal tissue, such as in the oral cavity.

Alteration Without Ablation

There are advantages to the technique of altering and not ablating the stratum corneum. In a preferred embodiment, the skin is altered, not ablated, so that its structural and biochemical makeup allow drugs to permeate. The consequence of this embodiment is: (1) the skin after irradiation still presents a barrier, albeit reduced, to external factors such as viruses and chemical toxins; (2) less energy is required than is required to ablate the stratum corneum, thus smaller and cheaper lasers can be used; and (3) less tissue damage occurs, thus resulting in more rapid and efficient healing.

Radiant Energy vs Laser Radiant Energy

The radiant energy emitted by lasers has the properties of being coherent, monochromatic, collimated and (typically) intense. Nevertheless, to enhance transdermal drug delivery or fluid, gas or biomolecule collection, the radiant energy used need not have these properties, or alternatively, can have one of all of these properties, but can be produced by a non-laser source For example, the pulsed light output of a pulsed xenon flashlamp can be filtered with an optical filter or other wavelength selection device, and a particular range of wavelengths can be selected out of the radiant energy output. While the incoherent and quasi-monochromatic output of such a configuration cannot be focussed down to a small spot as can coherent radiant energy, for the aforementioned purpose that may not be important as it could be focused down to a spot with a diameter on the order of millimeters. Such light sources can be used in a continuous wave mode if desirable.

The infrared output of incandescent lights is significantly more than their output in the visible, and so such light sources, if suitably filtered to eliminate undesirable energy that does not reduce barrier function, could be used for this purpose. In another embodiment of the invention, it would be possible to use an intense incandescent light (such as a halogen lamp), filter it with an optical filter or similar device, and used the continuous-wave radiant energy output to decrease the barrier function of stratum corneum without causing ablation. All of these sources of radiant energy can be used to produce pulses, or continuous-wave radiant energy.

Laser Device

The practice of the present invention has been found to be effectively performed by various types of lasers; for example, the TRANSMEDICA™ Er:YAG laser perforator, or the Schwartz Electro-Optical Er:YAG laser. Preferably, any pulsed laser producing energy that is strongly absorbed in tissue may be used in the practice of the present invention to produce the same result at a nonablative wavelength, pulse length, pulse energy, pulse number, and pulse rate. However, lasers which produce energy that is not strongly absorbed by tissue may also be used, albeit less effectively, in the practice of this invention. Additionally, as described herein, continuous-wave lasers may also be used in the practice of this invention.

FIGS. 1 and 2 are diagrammatic representations a typical laser that can be used for this invention. As shown in FIGS. 1 and 2, a typical laser comprises a power connection which can be either a standard electrical supply 10, or optionally a rechargeable battery pack 12, optionally with a power interlock switch 14 for safety purposes; a high voltage pulse-forming network 16; a laser pump-cavity 18 containing a laser rod 20, preferably Er:YAG; a means for exciting the laser rod, preferably a flashlamp 22 supported within the laser pump-cavity; an optical resonator comprised of a high reflectance mirror 24 positioned posterior to the laser rod and an output coupling mirror 26 positioned anterior to the laser rod; a transmitting focusing lens 28 positioned beyond the output coupling mirror; optionally a second focusing cylindrical lens 27 positioned between the output coupling mirror and the transmitting focusing lens; an applicator 30 for positioning the subject skin at the focal point of the laser beam, which is optionally heated for example with a thermoelectric heater 32, attached to the laser housing 34; an interlock 36 positioned between the applicator and the power supply; and optionally a beam dump 38 attached to the applicator with a fingertip access port 40.

The laser typically draws power from a standard 110 V or 220 V AC power supply 10 (single phase, 50 or 60 Hz) which is rectified and used to charge up a bank of capacitors included in the high voltage pulse-forming network 16. Optionally, a rechargeable battery pack 12 can be used instead. The bank of capacitors establishes a high DC voltage across a high output flashlamp 22. Optionally a power interlock 14, such as a keyswitch, can be provided which will prevent accidental charging of the capacitors and thus accidental laser excitation. A further interlock can be added to the laser at the applicator, such as a spring-loaded interlock 36, so that discharge of the capacitors requires both interlocks to be enabled.

With the depression of a switch, a voltage pulse can be superimposed on the already existing voltage across the flashlamp in order to cause the flashlamp to conduct, and, as a consequence, initiate the flash. The light energy from the flashlamp is located in the laser cavity 18 that has a shape such that most of the light energy is efficiently directed to the laser rod 20, which absorbs the light energy, and, upon de-excitation, subsequently lases. The laser cavity mirrors of low 26 and high 24 reflectivity, positioned collinearly with the long-axis of the laser rod, serve to amplify and align the laser beam.

Optionally, as shown in FIG. 12 the laser cavity mirrors comprise coatings 124, 126, applied to ends of the crystal element and which have the desired reflectivity characteristics. In a preferred embodiment an Er:YAG crystal is grown in a boule two inches in diameter and five inches long. The boule is core drilled to produce a rod 5–6 millimeters in diameter and five inches long. The ends of the crystal are ground and polished. The output end, that is the end of the element from which the laser beam exits, is perpendicular to the center axis of the rod within 5 arc minutes. The flatness of the output end is $\frac{1}{10}$ a wavelength (2.9 microns) over 90% of the aperture. The high reflectance end, that is the end opposite the output end, comprises a two meter convex spherical radius. The polished ends are polished so that there are an average of ten scratches and five digs per Military Specification Mil-0-13830A. Scratch and dig are subjective measurements that measure the visibility of large surface defects such as defined by U.S. military standards. Ratings consist of two numbers, the first being the visibility of scratches and the latter being the count of digs (small pits). A #10 scratch appears identical to a 10 micron wide standard scratch while a #1 dig appears identical to a 0.01 mm diameter standard pit. For collimated laser beams, one normally would use optics with better than a 40–20 scratch-dig rating.

Many coatings are available from Rocky Mountain Instruments, Colorado Springs, Colo. The coating is then vacuum deposited on the ends. For a 2.9 micron wavelength the coatings for the rear mirrored surface 124 should have a reflectivity of greater than 99%. The coating for the output end surface, by contrast, should have a reflectance of between 93% and 95%, but other mirrored surfaces with reflectivity as low as 80% are useful. Other vacuum deposited metallic coatings with known reflectance characteristics are widely available for use with other laser wavelengths.

The general equation which defines the reflectivity of the mirrors in a laser cavity necessary for the threshold for population inversion is:

$$R_1 R_2 (1-a_L)^2 \exp[(g_{21}-\alpha)2L]=1$$

where the $R_1$ and $R_2$ are the mirrors' reflectivities, $a_L$ is the total scattering losses per pass through the cavity, $g_{21}$ is the gain coefficient which is the ratio of the stimulated emission cross section and population inversion density, $\alpha$ is the absorption of the radiation over one length of the laser cavity, and L is the length of the laser cavity. Using the above equation, one can select a coating with the appropriate spectral reflectivity from the following references. W. Driscoll and W. Vaughan, "Handbook of Optics," ch. 8, eds., McGraw-Hill: NY (1978); M. Bass, et al., "Handbook of Optics," ch. 35, eds., McGraw Hill: NY (1995).

Optionally, as also shown in FIG. 12, the crystal element may be non-rigidly mounted. In FIG. 12 an elastomeric material O-ring 128 is in a slot in the laser head assembly housing 120 located at the high reflectance end of the crystal element. A second elastomeric material O-ring 130 is in a second slot in the laser head assembly at the output end of the crystal element. The O-rings contact the crystal element by concentrically receiving the element as shown. However, elastomeric material of any shape may be used so long as it provides elastomeric support for the element (directly or indirectly) and thereby permits thermal expansion of the element. Optionally, the flash lamp 22 may also be non-rigidly mounted. FIG. 12 shows elastomeric O-rings 134, 136, each in its own slot within the laser head assembly housing. In FIG. 12 the O-rings 134 and 136 concentrically receive the flash lamp. However, the flash lamp may be supported by elastomeric material of other shapes, including shapes without openings.

Figure 3:
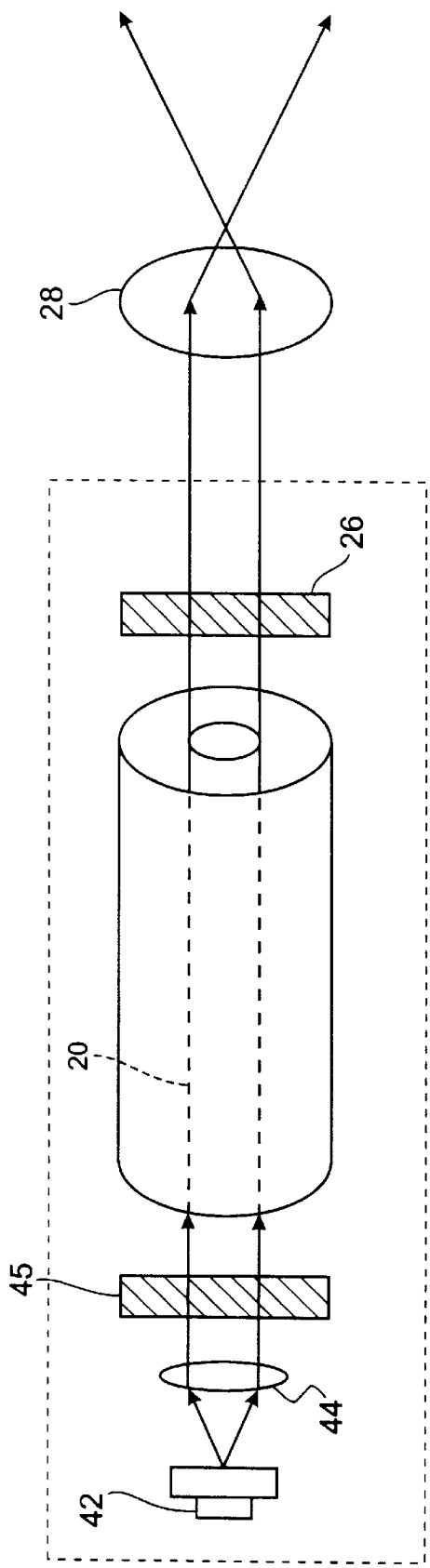
FIG. 3 shows an alternative means of exciting a laser rod using a diode laser.

Optionally, as shown in FIG. 3, a diode laser 42 that produces a pump-beam collinear with the long-axis of the laser crystal can be used instead of the flashlamp to excite the crystal. The pump-beam of this laser is collimated with a collimating lens 44, and transmitted to the primary laser rod through the high reflectance infrared mirror 45. This high reflectance mirror allows the diode pump laser beam to be transmitted, while reflecting infrared light from the primary laser.

The Er:YAG lasing material is the preferred material for the laser rod because the wavelength of the electromagnetic energy emitted by this laser, 2.94 microns, is very near one of the peak absorption wavelengths (approximately 3 microns) of water. Thus, this wavelength is strongly absorbed by water and tissue. The rapid heating of water and tissue causes perforation or alteration of the skin.

Other useful lasing material is any material which, when induced to lase, emits a wavelength that is strongly absorbed by tissue, such as through absorption by water, nucleic acids, proteins or lipids, and consequently causes the required perforation or alteration of the skin (although strong absorption is not required). A laser can effectively cut or alter tissue to create the desired perforations or alterations where tissue exhibits an absorption coefficient of 10–10,000 $cm^{-1}$. Examples of useful lasing elements are pulsed $CO_2$ lasers, Ho:YAG (holmium:YAG), Er:YAP, Er/Cr:YSGG (erbium/chromium: yttrium, scandium, gallium, garnet; 2.796 microns), Ho:YSGG (holmium: YSGG; 2.088 microns), Er:GGSG (erbium: gadolinium, gallium, scandium, garnet), Er:YLF (erbium: yttrium, lithium, fluoride; 2.8 microns), Tm:YAG (thulium: YAG; 2.01 microns), Ho:YAG (holmium: YAG; 2.127 microns); Ho/Nd:YAlO$_3$ (holmium/neodymium: yttrium, aluminate; 2.85–2.92 microns), cobalt:MgF$_2$ (cobalt: magnesium fluoride; 1.75–2.5 microns), HF chemical (hydrogen fluoride; 2.6–3 microns), DF chemical (deuterium fluoride; 3.6–4 microns), carbon monoxide (5–6 microns), deep UV lasers, and frequency tripled Nd:YAG (neodymium:YAG, where the laser beam is passed through crystals which cause the frequency to be tripled).

Utilizing current technology, some of these laser materials provide the added benefit of small size, allowing the laser to be small and portable. For example, in addition to Er:YAG, Ho:YAG lasers also provide this advantage.

Solid state lasers, including but not limited to those listed above, may employ a polished barrel crystal rod. The rod surface may also contain a matte finish as shown in FIG. 13. However, both of these configurations can result in halo rays that surround the central output beam. Furthermore, an all-matte finish, although capable of diminishing halo rays relative to a polished rod, will cause a relatively large decrease in the overall laser energy output. In order to reduce halo rays and otherwise affect beam mode, the matte finish can be present on bands of various lengths along the rod, each band extending around the entire circumference of the rod. Alternatively, the matte finish may be present in bands along only part of the rod's circumference. FIG. 14 shows a laser crystal element in which the matte finish is present upon the full circumference of the element along two-thirds of its length. Alternatively, as shown in FIG. 15, matte stripes may be present longitudinally along the full length of the rod. The longitudinal stripes may alternatively exist along only part of the length of the rod, such as in stripes of various lengths. A combination of the foregoing techniques may be used to affect beam shape. Other variations of patterns may also be employed in light of the beam shape desired. The specific pattern may be determined based on the starting configuration of the beam from a 100% polished element in light of the desired final beam shape and energy level. A complete matte finish element may also be used as the starting reference point.

For purposes of beam shape control, any surface finish of greater than 30 microinches is considered matte. A microinch equals one millionth (0.000001) inch, which is a common unit of measurement employed in establishing standard roughness unit values. The degree of roughness is calculated using the root-mean-square average of the distances in microinches above or below the mean reference line, by taking the square root of the mean of the sum of the squares of these distances. Although matte surfaces of greater than 500 microinches may be used to affect beam shape, such a finish will seriously reduce the amount of light energy that enters the crystal rod, thereby reducing the laser's energy.

To remove the beam halo, a matte area of approximately 50 microinches is present around the full circumference of an Er:YAG laser rod for two-thirds the length of the rod. The non-matte areas of the rod are less than 10 microinches. A baseline test of the non-matte rod can be first conducted to determine the baseline beam shape and energy of the rod. The matte areas are then obtained by roughing the polished crystal laser rod, such as with a diamond hone or grit blaster. The specific pattern of matte can be determined with respect to the desired beam shape and required beam energy level.

This results in a greatly reduced beam halo. The rod may also be developed by core drilling a boule of crystal so that it leaves an overall matte finish and then polishing the desired areas, or by refining a partially matte, partially polished boule to achieve the desired pattern.

The beam shape of a crystal laser rod element may alternatively be modified as in FIG. 16 by surrounding the rod 20 in a material 160 which is transparent to the exciting light but has an index of refraction greater than the rod. Such a modification can reduce the halo of the beam by increasing the escape probability of off-axis photons within the crystal. This procedure may be used in place of or in addition to the foregoing matte procedure.

The emitted laser beam is focused down to a millimeter or submillimeter sized spot with the use of the focusing lens 28. Consideration of laser safety issues suggests that a short focal length focusing lens be used to ensure that the energy fluence rate (W/cm$^2$) is low except at the focus of the lens where the tissue sample to be perforated or altered is positioned. Consequently, the hazard of the laser beam is minimized.

The beam can be focused so that it is narrower along one axis than the other in order to produce a slit-shaped perforation or alteration through the use of a cylindrical focusing lens 27. This lens, which focuses the beam along one axis, is placed in series with the transmitting focusing lens 28. When perforations or alterations are slit-shaped, the patient discomfort or pain associated with the perforation or alteration is considerably reduced.

Figure 4:
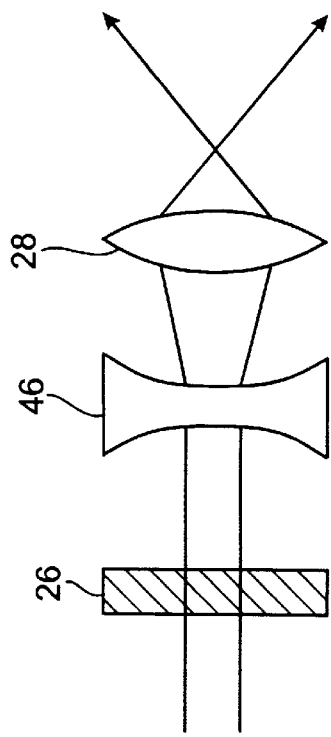
FIG. 4 shows an alternative focusing mechanism.

Optionally, the beam can be broadened, for instance through the use of a concave diverging lens 46 (FIG. 4) prior to focusing through the focusing lens 28. This broadening of the beam results in a laser beam with an even lower energy fluence rate a short distance beyond the focal point, consequently reducing the hazard level. Furthermore, this optical arrangement reduces the optical aberrations in the laser spot at the treatment position, consequently resulting in a more precise perforation or alteration.

Figure 5A:
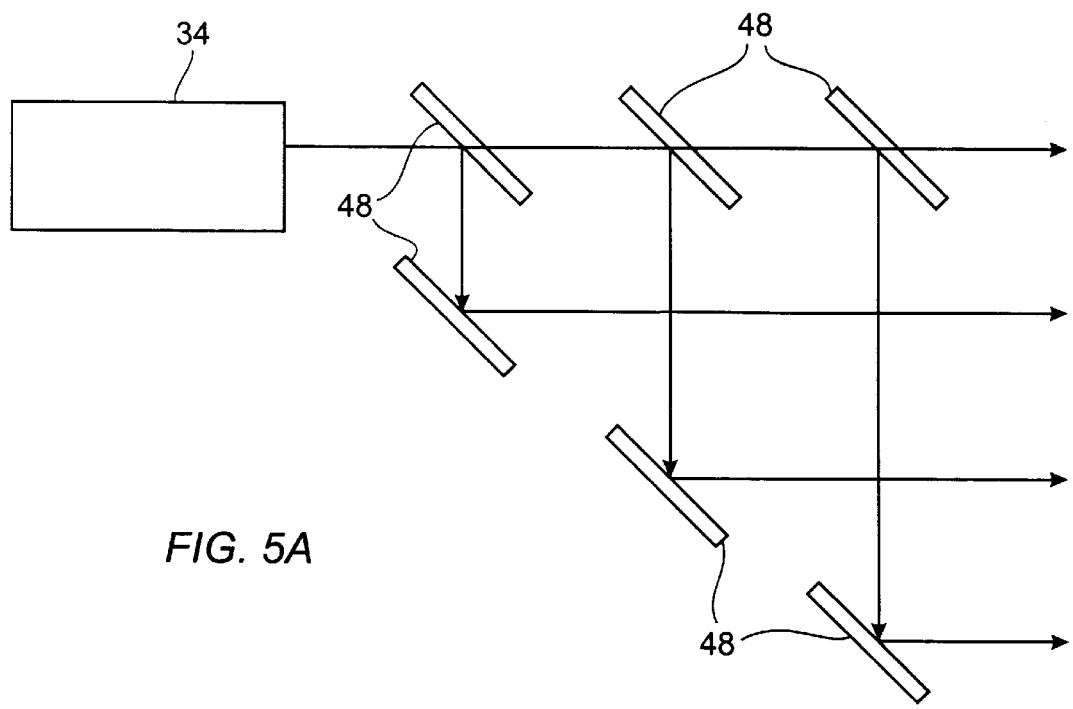
FIGS. 5A & 5B show optional beam splatters for creating multiple simultaneous perforations.
Figure 5B:
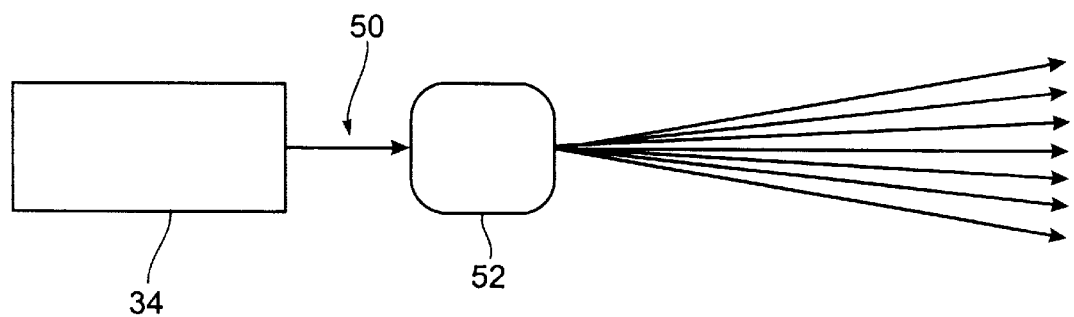

Also optionally, the beam can be split by means of a beam-splitter to create multiple beams capable of perforating or altering several sites simultaneously or near simultaneously. FIG. 5 provides two variations of useful beam splitters. In one version, multiple beam splitters 48 such as partially silvered mirrors, dichroic mirrors, or beam-splitting prisms can be provided after the beam is focused. Alternatively, an acousto-optic modulator 52 can be supplied with modulated high voltage to drive the modulator 52 and bend the beam. This modulator is outside the laser cavity. It functions by deflecting the laser beam sequentially and rapidly at a variety of angles to simulate the production of multiple beams.

Portability

Currently, using a portable TRANSMEDICA™ Er:YAG laser, the unit discharges once per 20–30 seconds. This can be increased by adding a battery and capacitor and cooling system to obtain a quicker cycle. Multiple capacitors can be strung together to get the discharge rate down to once every 5 or 10 seconds (sequentially charging the capacitor banks). Thus, getting a higher repetition rate than with a single capacitor.

The TRANSMEDICA™ Er:YAG laser incorporates a flashlamp, the output of which is initiated by a high-voltage pulse of electricity produced by a charged capacitor bank. Due to the high voltages required to excite the flashlamp, and because the referred to version of the laser incorporates dry cells to run (thus the charging current is much less than a wall-plug could provide), then the capacitors take about 20 seconds to sufficiently charge. Thus, if a pulse repetition rate of 1 pulse/20 seconds is desirable, it would be suitable to have multiple capacitor banks that charge sequentially (i.e. as one bank fires the flashlamp, another bank, which has been recharging, fires, and so on). Thus, the pulse repetition rate is limited only be the number of capacitor banks incorporated into the device (and is also limited by the efficiency of waste-heat removal from the laser cavity).

A small heater, such as a thermoelectric heater 32, is optionally positioned at the end of the laser applicator proximal to the site of perforation. The heater raises the temperature of the tissue to be perforated or altered prior to laser irradiation. This increases the volume of fluid collected when the device is used for that purpose. A suggested range for skin temperature is between 36° C. and 45° C., although any temperature which causes vasodilation and the resulting increase in blood flow without altering the blood chemistry is appropriate.

Container Unit

Figure 8:
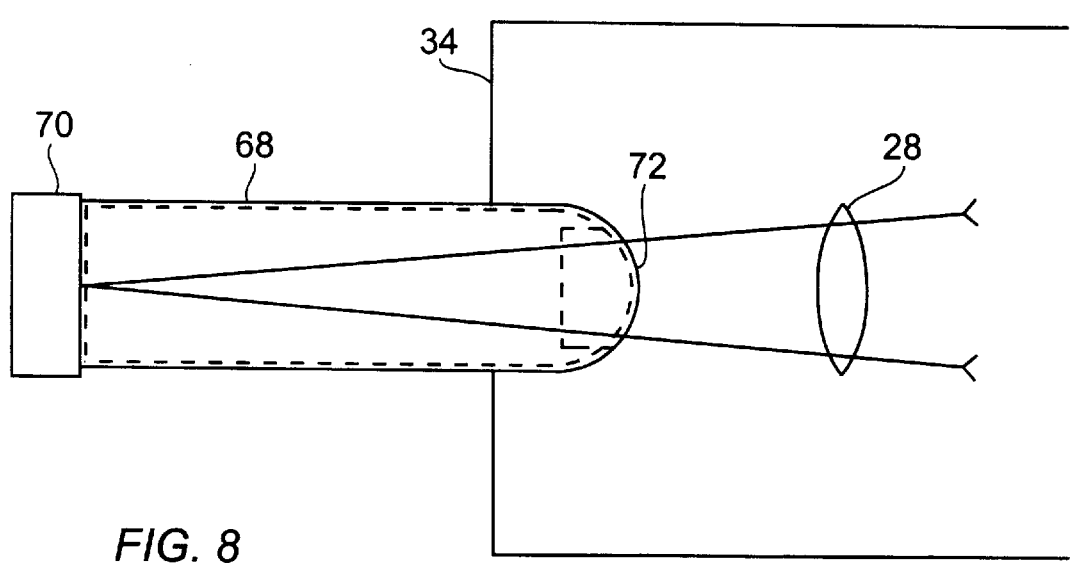
FIG. 8 shows an optional container unit for collecting fluids, gases or other biomolecules, ablated tissue, and/or other matter released from the site of irradiation, and for reducing noise resulting from the interaction between the laser and the patient's tissue.

A container unit 68 is optionally fitted into the laser housing and is positioned proximal to the perforation or alteration site. The container unit reduces the intensity of the sound produced when the laser beam perforates or alters the patient's tissue, increases the efficiency of fluid, gas or other biomolecule collection, and collects the ablated tissue and other matter released by the perforation. The container unit can be shaped so as to allow easy insertion into the laser housing and to provide a friction fit within the laser housing. FIG. 8 shows a typical container unit inserted into the laser housing and placed over the perforation site.

The container unit 68 comprises a main receptacle 82, including a lens 84. The main receptacle collects the fluid, gas or other biomolecule sample, the ablated tissue, and/or other matter released by the perforation. The lens is placed such that the laser beam may pass through the lens to the perforation site but so that the matter released by the perforation does not splatter back onto the applicator. The container unit also optionally includes a base 86, attached to the receptacle. The base can optionally be formed so as to be capable of being inserted into the applicator to disengage a safety mechanism of the laser, thereby allowing the laser beam to be emitted.

As shown in FIGS. 17a through 17g, the shape and size of the container unit 68 are such as to allow placement next to or insertion into the applicator, and to allow collection of the fluid, gas or other biomolecule samples, ablated tissue, and/or other matter released by the perforation or alteration. Examples of shapes that the main receptacle may take include cylinders, bullet shapes, cones, polygons and free form shapes. Preferably, the container unit has a main receptacle, with a volume of around 1–2 milliliters. However, larger and smaller receptacles will also function appropriately.

The lens 84, which allows the laser beam to pass through while preventing biological and other matter from splattering back onto the applicator, is at least partially transparent. The lens is constructed of a material that transmits the laser wavelength utilized and is positioned in the pathway of the laser beam, at the end of the container unit proximal to the beam. The transmitting material can be quartz, but other examples of suitable infrared transmitting materials include rock salt, germanium, glass, crystalline sapphire, polyvinyl chloride and polyethylene. However, these materials should not contain impurities that absorb the laser beam energy. As shown in FIG. 20, the lens may optionally include a mask of non-transmitting material 85 such that the lens may shape the portion of the beam that is transmitted to the perforation site.

The main receptacle 82 is formed by the lens and a wall 88, preferably extending essentially away from the perimeter of the lens. The open end of the main receptacle or rim 90 is placed adjacent to the perforation or alteration site. The area defined by the lens, wall of the main receptacle and perforation or alteration site is thereby substantially enclosed during the operation of the laser.

The base 86 is the part of the container unit that can optionally be inserted into the applicator. The base may comprise a cylinder, a plurality of prongs or other structure. The base may optionally have threading. Optionally, the base, when fully inserted, disengages a safety mechanism of the laser, allowing the emission of the laser beam.

A typical container unit can comprise a cylindrical main receptacle 82, a cylindrical base 86, and an at least partially transparent circular lens 84 in the area between the main receptacle and base. Optionally, the lens may include a mask that shapes the beam that perforates the tissue. The interior of the main receptacle is optionally coated with anticoagulating and/or preservative chemicals. The container unit can be constructed of glass or plastic. The container unit is optionally disposable.

FIGS. 19*a* nad 19*b* show examples of the use of a container unit with a laser for the purpose of drawing fluids, gases or other biomolecules or to administer pharmaceuticals. In this embodiment the applicator 30 is surrounded by the housing 34. The container unit is inserted in the applicator 30 and aligned so as to be capable of defeating the interlock 36. The base 86 of the container unit in this embodiment is within the applicator 30, while the rim 90 of the receptacle 82 is located adjacent to the tissue to be perforated.

Additionally, the container unit can be evacuated. The optional vacuum in the container unit exerts a less than interstitial fluid or the pressure of gases in the blood over the perforation or alteration site, thereby increasing the efficiency in fluid, gas or other biomolecule collection. The container unit is optionally coated with anticoagulating and/or preservative chemicals. The container unit's end proximal to the perforation or alteration site is optionally sealed air-tight with a plug 70. The plug is constructed of material of suitable flexibility to conform to the contours of the perforation site (e.g., the finger). The desired perforation or alteration site is firmly pressed against the plug. The plug's material is preferably impermeable to gas transfer. Furthermore, the plug's material is thin enough to permit perforation of the material as well as perforation of the skin by the laser. The plug can be constructed of rubber, for example.

Figure 9:
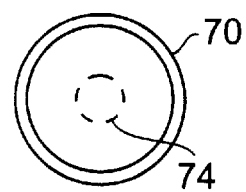
FIG. 9 shows a plug and plug perforation center.

The plug perforation center 74, as shown in FIG. 9, is preferably constructed of a thin rubber material. The thickness of the plug is such that the plug can maintain the vacuum prior to perforation, and the laser can perforate both the plug and the tissue adjacent to the plug. For use with an Er:YAG laser, the plug can be in the range of approximately about 100 to 500 microns thick.

The plug perforation center 74 is large enough to cover the perforation or alteration site. Optionally, the perforated site is a round hole with an approximate diameter ranging from about 0.1–1 mm, or slit shaped with an approximate width of about 0.05–0.5 mm and an approximate length up to about 2.5 mm. Thus, the plug perforation center is sufficiently large to cover perforation sites of these sizes.

Figure 10:
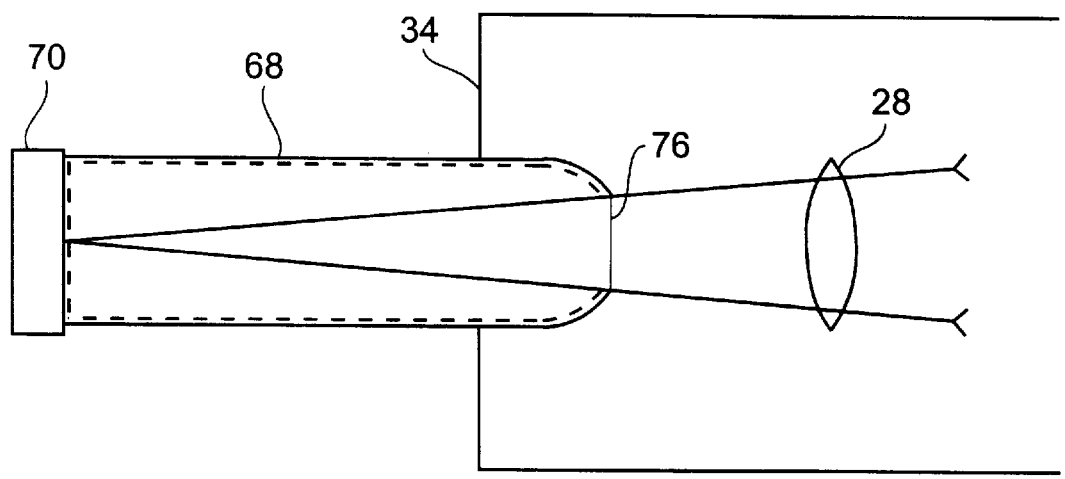
FIG. 10 shows an optional container unit for collecting ablated tissue and reducing noise resulting from the interaction between the laser and the patient's tissue.

As shown in FIG. 10, the container unit 68 can include a hole 76 through which the laser passes. In this example, the container unit optionally solely collects ablated tissue. As in the other examples, the site of irradiation is firmly pressed against the container unit. The container unit can optionally include a plug proximal to the perforation site, however it is not essential because there is no need to maintain a vacuum. The container unit reduces the noise created from interaction between the laser beam and the patient's tissue and thus alleviates the patient's anxiety and stress.

Figure 18:
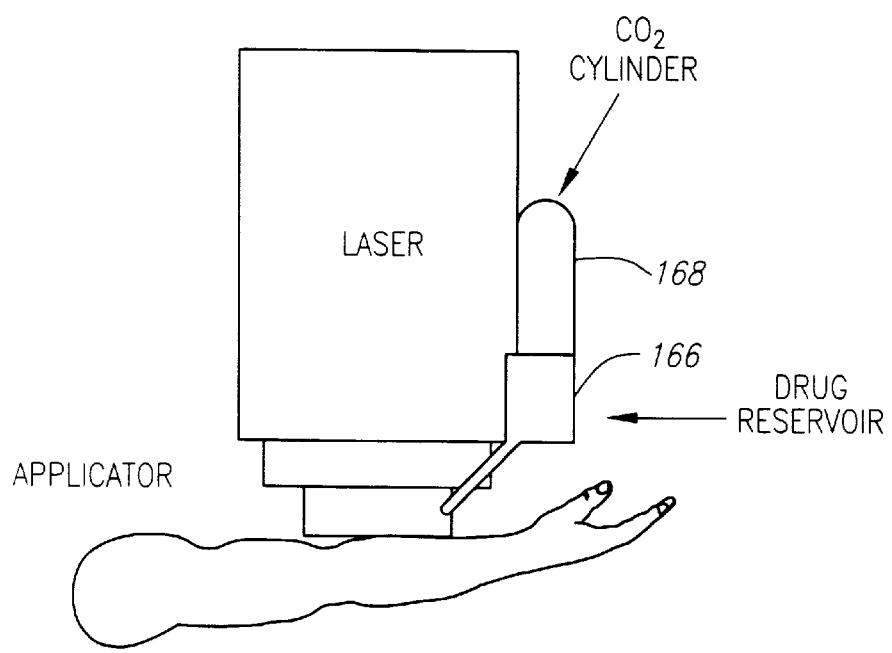
FIG. 18 shows an atomizer for the delivery of anesthetics or pharmaceuticals.

The container may also be modified to hold, or receive through an opening, a pharmaceutical or other substance, which may then be delivered simultaneously, or shortly after irradiation occurs. FIG. 11 shows an example of a container with a built-in drug reservoir and roll-on apparatus for delivery. FIG. 18 shows a container with an applicator which in turn comprises an atomizer with attached high pressure gas cylinder.

Optionally, the container unit is disposable, so that the container unit and plug can be discarded after use.

In order to sterilize the skin before perforation or alteration, a sterile alcohol-impregnated patch of paper or other thin material can optionally be placed over the site to be perforated. This material can also prevent the blowing off of potentially infected tissue in the plume released by the perforation. The material must have low bulk absorption characteristics for the wavelength of the laser beam. Examples of such material include, but are not limited to, a thin layer of glass, quartz, mica, or sapphire. Alternatively, a thin layer of plastic, such as a film of polyvinyl chloride or polyethylene, can be placed over the skin. Although the laser beam may perforate the plastic, the plastic prevents most of the plume from flying out and thus decreases any potential risk of contamination from infected tissue. Additionally, a layer of a viscous sterile substance such as vaseline can be added to the transparent material or plastic film to increase adherence of the material or plastic to the skin and further decrease plume contamination. Additionally, such a patch can be used to deliver allergens, local anesthetics or other pharmaceuticals as described below.

Figure 6:
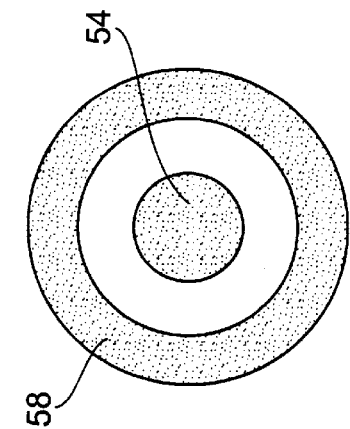
FIG. 6 shows a patch that can be used to sterilize the site of irradiation.
Figure 7A:
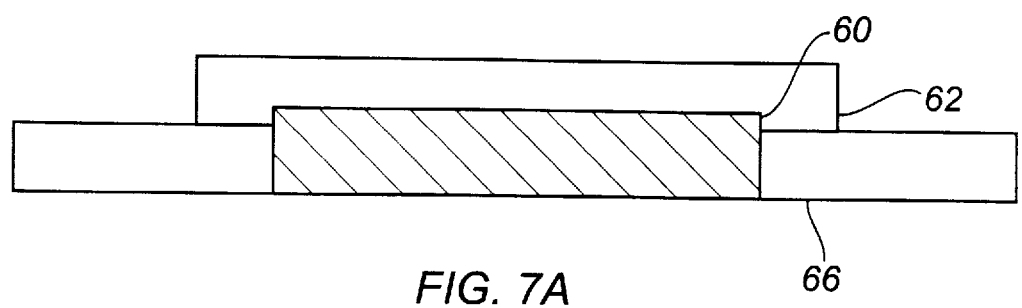
FIGS. 7A & 7B show alternative patches for sterilization and/or delivery of pharmaceuticals, and/or collection of fluids, gases or other biomolecules.
Figure 7B:
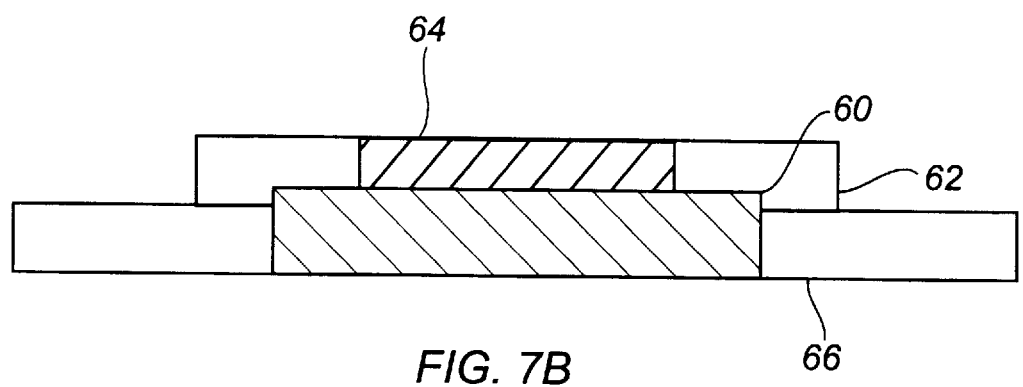

Examples of such a patch are provided in FIGS. 6 and 7. In FIG. 6, alcohol impregnated paper 54 is surrounded by a temporary adhesive strip 58. Side views of two alternative patches are shown in FIG. 7, where a sterilizing alcohol, antibiotic ointment, allergen, or pharmaceutical is present in the central region of the patch 60. This material is held in place by a paper or plastic layer 62, optionally with a laser-transparent material 64. Examples of such material include, but are not limited to, mica, quartz or sapphire which is transparent to the laser beam at the center of the patch. However, the material need not be totally transparent. The patch can be placed on the skin using an adhesive 66.

Modulated Laser

In addition to the pulsed lasers listed above, a modulated laser can be used to duplicate a pulsed laser for the purpose of enhancing topical drug delivery, as well as enhancing the removal of fluids, gases or other biomolecules. This is accomplished by chopping the output of the continuous-wave laser by either modulating the laser output mechanically, optically or by other means such as a saturable absorber. (See, e.g., Jeff Hecht, "The Laser Guidebook," McGraw-Hill:NY, 1992). Examples of continuous-wave lasers include $CO_2$ which lases over a range between 9–11 microns (e.g. Edinburgh Instruments, Edinburgh, UK), Nd:YAG, Thullium:YAG (Tm:YAG), which lases at 2.1 microns (e.g. CLR Photonics Inc., Boulder Colo.), semiconductor (diode) lasers which lase over a range from 1.0–2.0 microns (SDL Inc., San Jose, Calif.).

The chopping of the laser output (for example, with a mechanical chopper from Stanford Research Instruments Inc., Sunnyvale Calif.) will preferably result in discrete moments of irradiation with temporal widths from a few tenths of milliseconds, down to nanoseconds or picoseconds. Alternatively, in the case of diode lasers, the lasing process can be modulated by modulating the laser excitation current. A modulator for a laser diode power supply can be purchased from SDL Inc., San Jose, Calif. Alternatively, the continuous-wave beam can be optically modulated using, for example, an electro-optic cell (e.g. from New Focus Inc., Santa Clara, Calif.) or with a scanning mirror from General Scanning, Inc., Watertown Mass.

The additive effect of multiple perforations may be exploited with diode lasers. Laser diodes supplied by SDL Corporation (San Jose, Calif.) transmit a continuous beam of from 1.8 to 1.96 micron wavelength radiant energy. These diodes operate at up to 500 mW output power and may be coupled to cumulatively produce higher energies useful for stratum corneum ablation. For example, one diode bar may contain ten such diodes coupled to produce pulsed energy of 5 mJ per millisecond. It has been shown that an ablative effect may be seen with as little as 25 mJ of energy delivered to a 1 mm diameter spot. Five 5 millisecond pulses or (25) one millisecond pulses from a diode laser of this type will thus have an ablative effect approximately equivalent to one 25 mJ pulse in the same time period.

The following examples are descriptions of the use of a laser to increase the permeability of the stratum corneum for the purpose of drawing fluids, gases or other biomolecules, as well as for pharmaceutical delivery. These examples are not meant to limit the scope of the invention, but are merely embodiments.

EXAMPLE 1

The laser comprises a flashlamp (PSC Lamps, Webster, N.Y.), an Er:YAG crystal (Union Carbide Crystal Products, Washagoul, Wash.), optical-resonator mirrors (CVI Laser Corp., Albuquerque, N.M.), an infrared transmitting lens (Esco Products Inc., Oak Ridge, N.J.), as well as numerous standard electrical components such as capacitors, resistors, inductors, transistors, diodes, silicon-controlled rectifiers, fuses and switches, which can be purchased from any electrical component supply firm, such as Newark Electronics, Little Rock, Ark.

EXAMPLE 2

An infrared laser radiation pulse was formed using a solid state, pulsed, Er:YAG laser consisting of two flat resonator mirrors, an Er:YAG crystal as an active medium, a power supply, and a means of focusing the laser beam. The wavelength of the laser beam was 2.94 microns. Single pulses were used.

The operating parameters were as follows: The energy per pulse was 40, 80 or 120 mJ, with the size of the beam at the focal point being 2 mm, creating an energy fluence of 1.27, 2.55 or 3.82 J/cm$^2$. The pulse temporal width was 300 $\mu$s, creating an energy fluence rate of 0.42, 0.85 or 1.27×10$^4$ W/cm$^2$.

Transepidermal water loss (TEWL) measurements were taken of the volar aspect of the forearms of human volunteers. Subsequently the forearms were positioned at the focal point of the laser, and the laser was discharged. Subsequent TEWL measurements were collected from the irradiation sites, and from these the measurements of unirradiated controls were subtracted. The results (shown in FIG. 27) show that at pulse energies of 40, 80 and 120 mJ, the barrier function of the stratum corneum was reduced and the resulting water loss was measured to be 131, 892 and 1743 gm/m$^2$/hr respectively. The tape stripe positive control (25 pieces of Scotch Transpore tape serially applied and quickly removed from a patch of skin) was measured to be 9.0 gm/m$^2$/hr, greater than untouched controls; thus the laser is more efficient at reducing the barrier function of the stratum corneum than tape-stripping.

Clinical assessment was conducted 24 hours after irradiation. Only a small eschar was apparent on the site lased at high energy, and no edema was present. None of the volunteers experienced irritation or required medical treatment.

EXAMPLE 3

An infrared laser radiation pulse was formed using a solid state, pulsed, Er:YAG laser consisting of two flat resonator mirrors, an Er:YAG crystal as an active medium, a power supply, and a means of focusing the laser beam. The wavelength of the laser beam was 2.94 microns. A single pulse was used.

The operating parameters were as follows: The energy per pulse was 60 mJ, with the size of the beam at the focal point being 2 mm, creating an energy fluence of 1.91 J/cm$^2$. The pulse temporal width was 300 $\mu$s, creating an energy fluence rate of 0.64×10$^4$ W/cm$^2$.

The volar aspect of the forearm of a volunteer was placed at the focal point of the laser, and the laser was discharged. After discharge of the laser, the ablated site was topically administered a 30% liquid lidocaine solution for two minutes. A 26G-0.5 needle was subsequently inserted into the laser ablated site with no observable pain. Additionally, after a 6-minute anesthetic treatment, a 22G-1 needle was fully inserted into the laser ablated site with no observable pain. The volunteer experienced no irritation and did not require medical treatment.

EXAMPLE 4

Ablation threshold energy: Normally hydrated (66%) stratum corneum was sandwiched between two microscope cover slides, and exposed to a single pulse of irradiation from the Er:YAG laser. Evidence of ablation was determined by holding the sample up to a light and seeing whether any stratum corneum was left at the irradiated site. From this experiment, it was determined that the irradiation threshold energy (for a 2 mm irradiation spot) was approximately 90–120 mJ. The threshold will likely be higher when the stratum corneum is still overlying epidermis, as in normal skin, since it takes energy to remove the stratum corneum from the epidermis, to which it is adherent.

EXAMPLE 5

Figure 28:
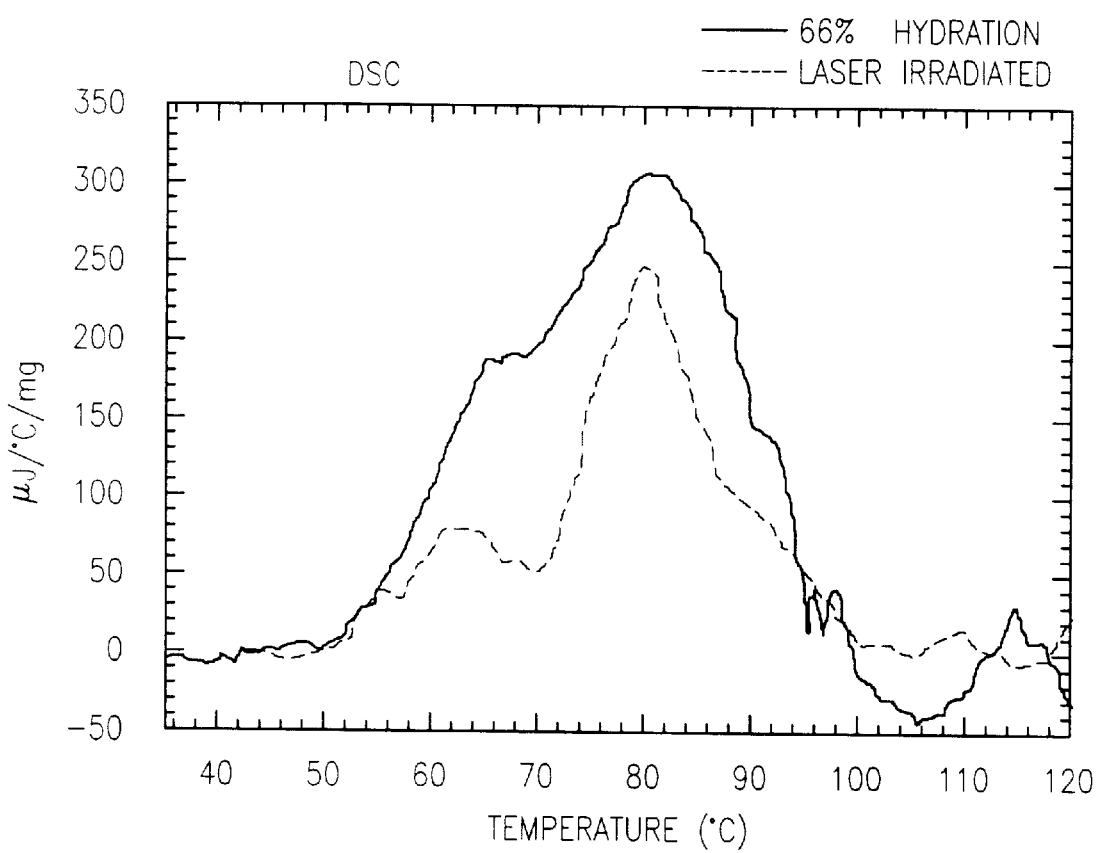
FIG. 28 is a chart showing a DSC scan of normally hydrated (66%) human stratum corneum, and a scan of Er:YAG laser irradiated stratum corneum using a subablative pulse energy of 60 mJ.
Figure 29:
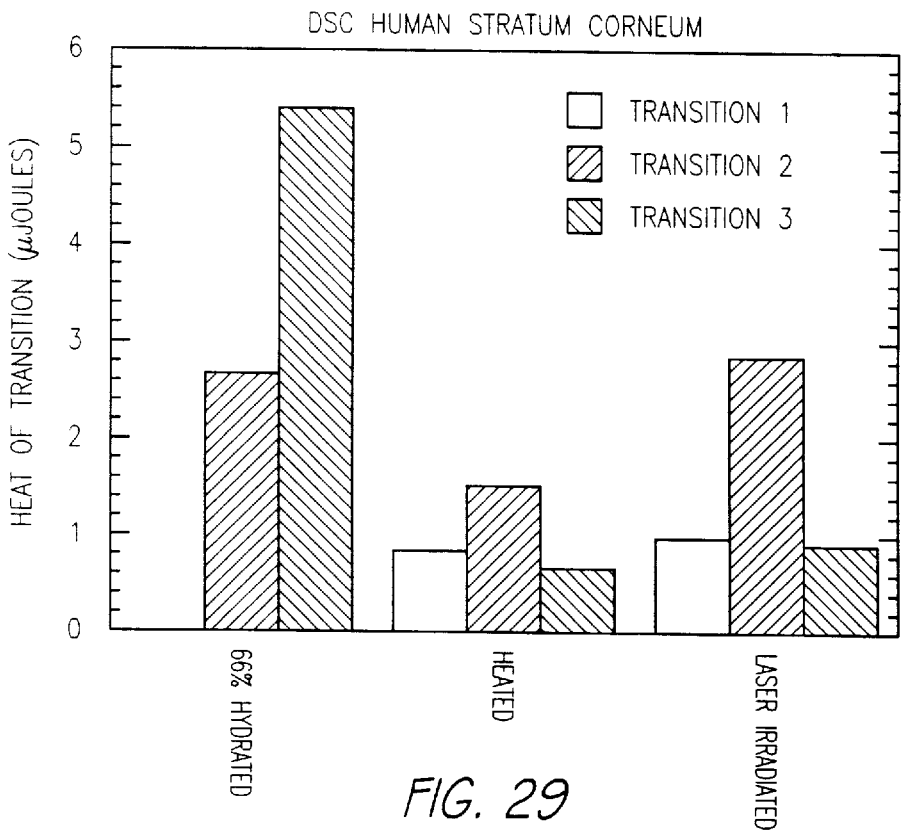
FIGS. 29–31 are charts showing the heat of transition ($\mu J$), center of the transition (° C.) and the full-width at half-maximum of the transition (° C.) of three peaks in the DSC spectra for stratum corneum treated different ways.
Figure 30:
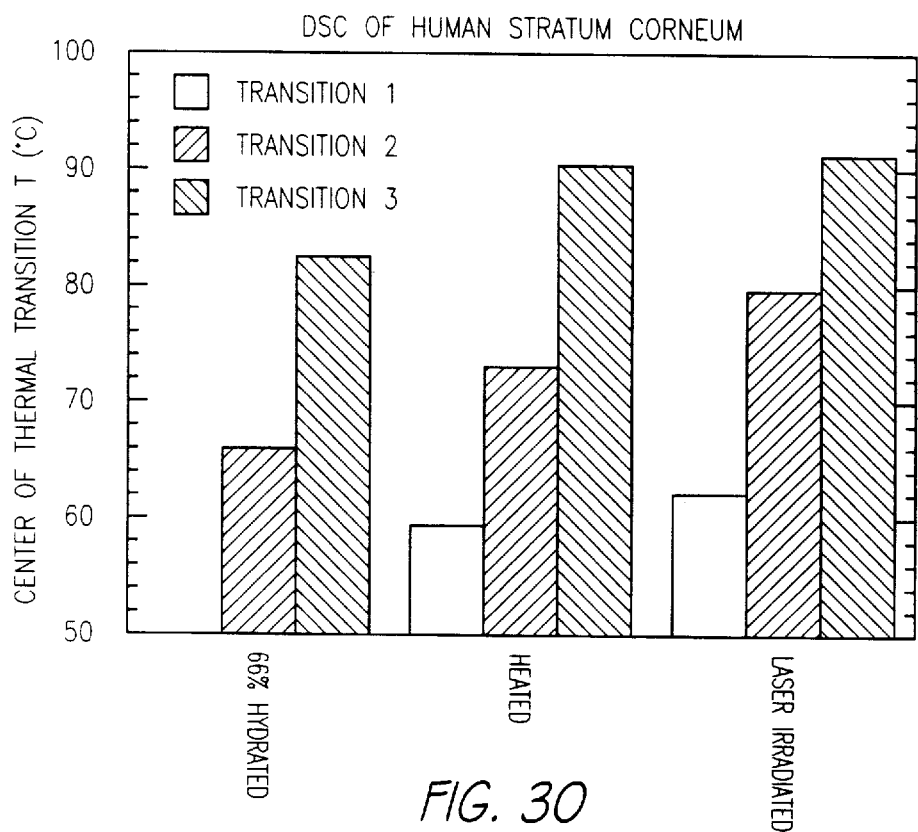
Figure 31:
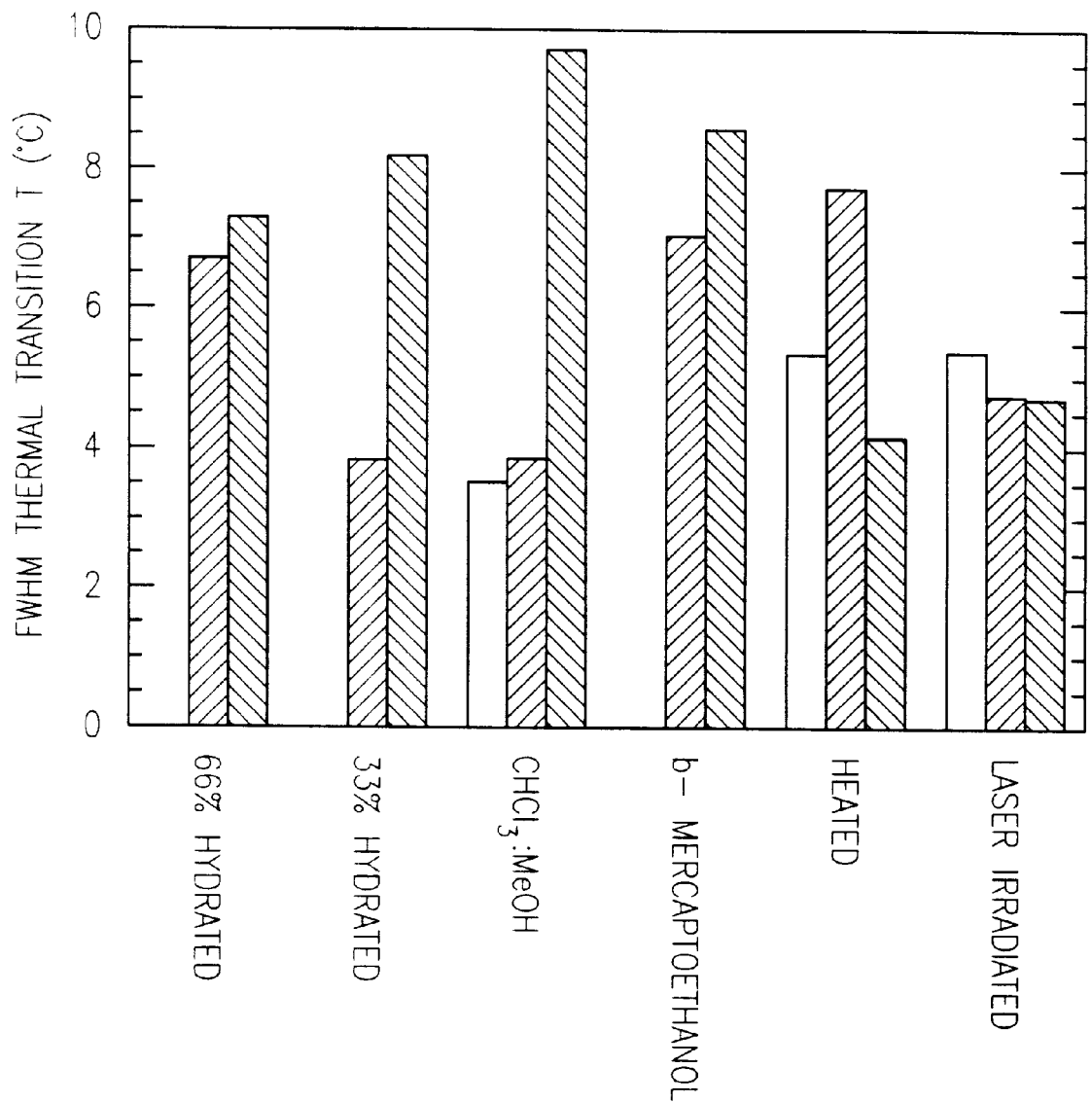

Differential Scanning Calorimetry (DSC): FIG. 28 shows a DSC scan of normally hydrated (66%) human stratum corneum, and a scan of stratum corneum irradiated with the Er:YAG laser using a subablative pulse energy of 60 mJ. Defining the thermal transition peaks at approximately 65, 80 and 92° C., we determined the heat of transition ($\mu$J), center of the transition (° C.) and the full-width at half-maximum of the transition (° C.) (FIGS. 29–31). The results shown are on normal 66% hydrated stratum corneum, dehydrated 33% stratum corneum, steam heated stratum corneum, Er:YAG laser irradiated stratum corneum, or stratum corneum that was immersed in chloroform-methanol (a lipid solvent), or beta-mercaptoethanol (a protein denaturant). The effect of laser irradiation on stratum corneum is consistent (depending on which transition you look at, 1, 2 or 3) with changes seen due to thermal damage (i.e. heated with steam), and delipidization. Permeation with ($^3H_2O$) and transepidermal impedance experiments on skin treated the same way showed that the result of these treatments (heat, solvent or denaturant) resulted in increased permeation. Thus, the changes induced in the stratum corneum with these treatments, changes which are consistent with those seen in laser irradiated stratum corneum, and changes which do not result in stratum corneum ablation, result in increased permeation.

EXAMPLE 6

Figure 32:
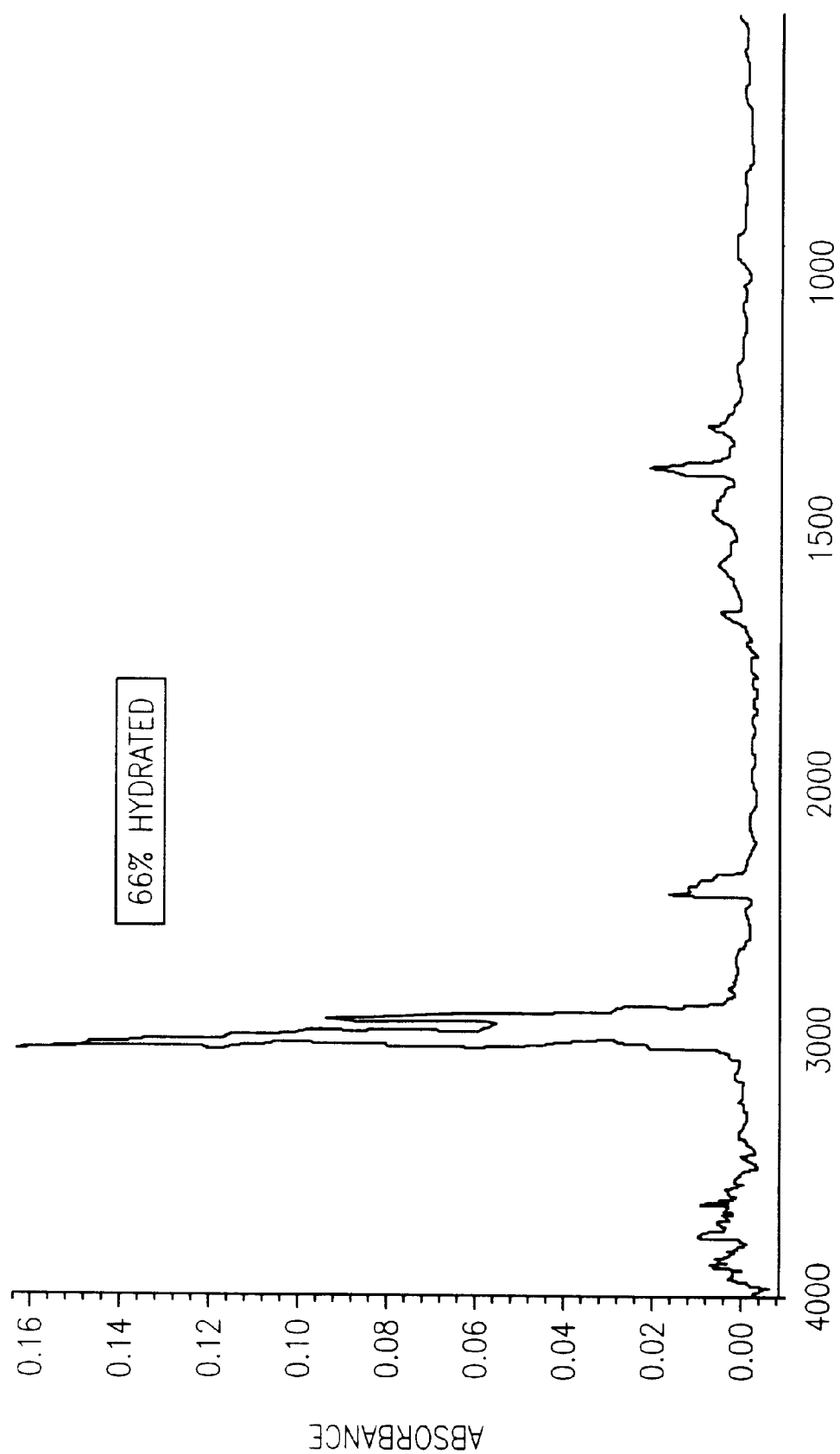
FIGS. 32–33 are charts of FTIR spectra of control and lased stratum corneum.
Figure 33:
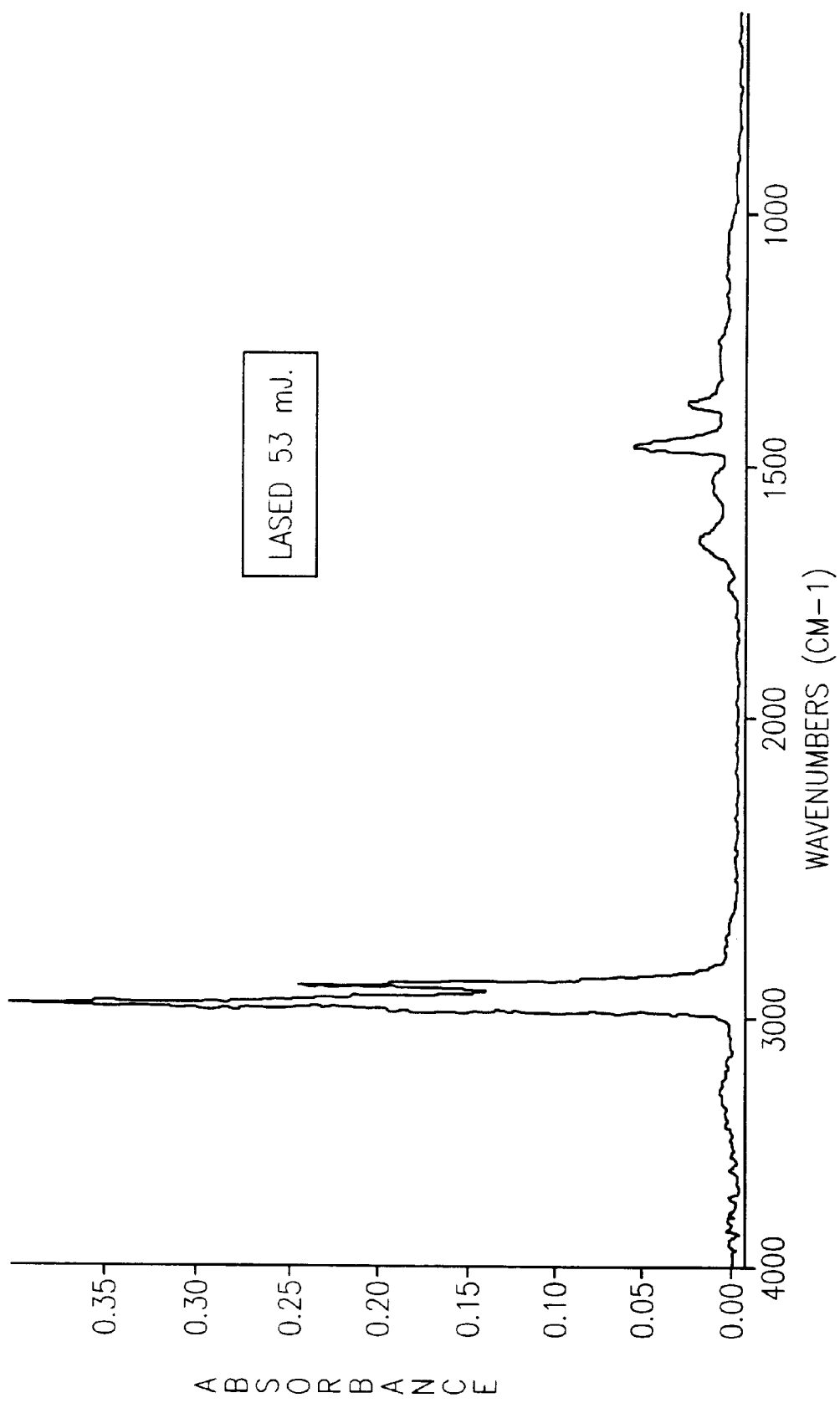
Figure 34:
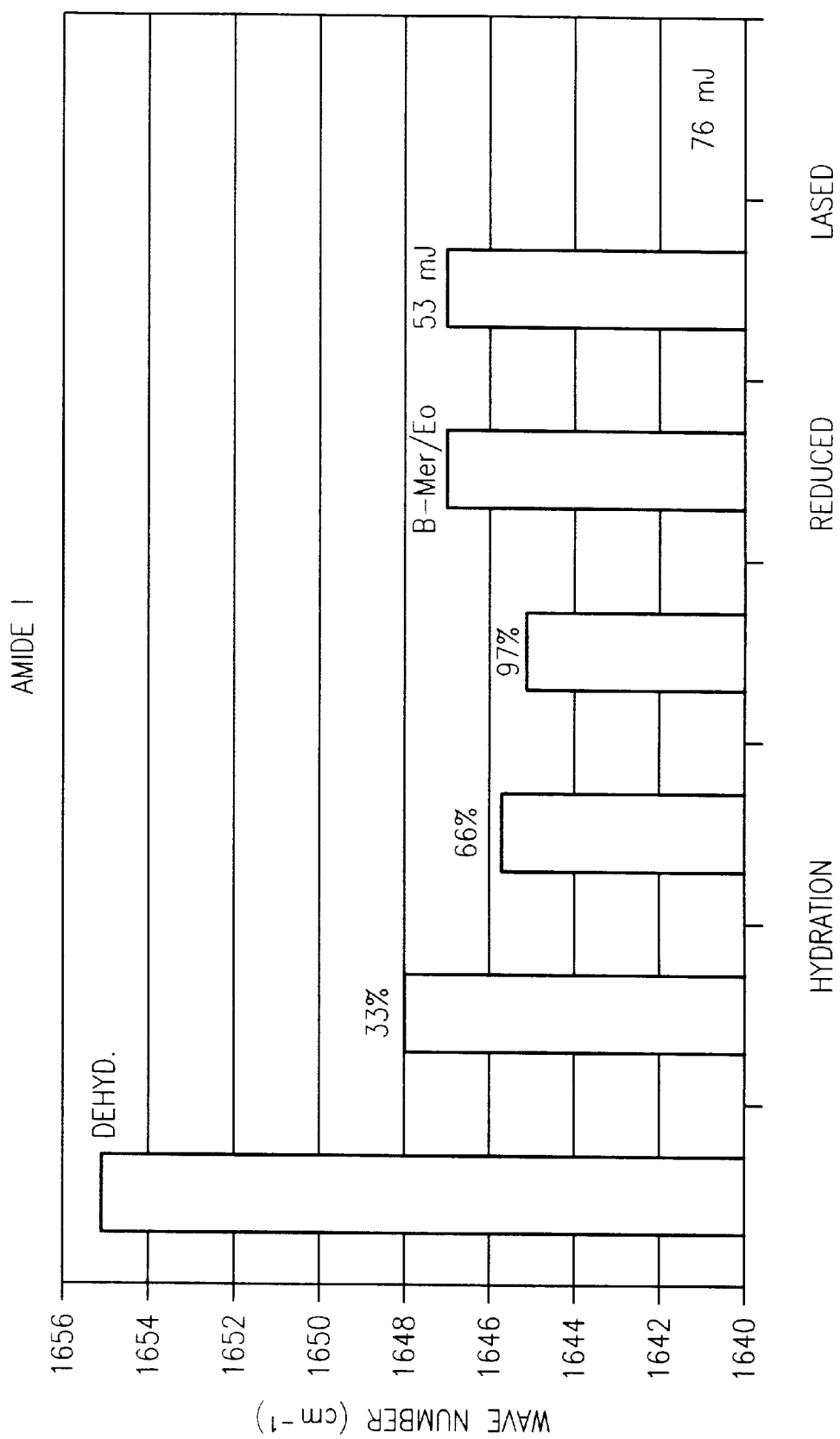
FIG. 34 shows Amide I band position ($cm^{-1}$) as a function of stratum corneum treatment.
Figure 35:
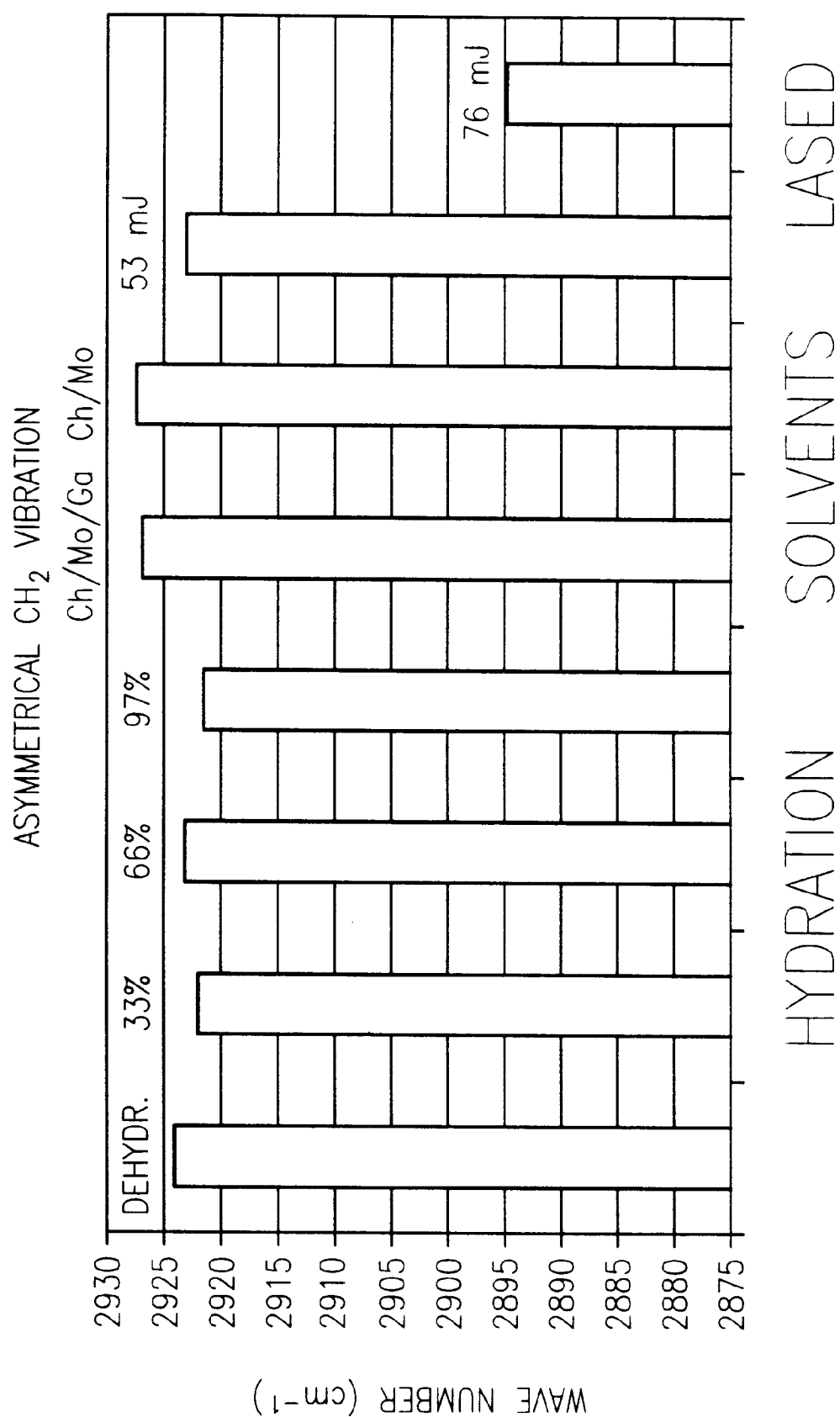
FIG. 35 shows $CH_2$ vibration position ($cm^{-1}$) as a function of stratum corneum treatment.

Fourier Transform Infrared (FTIR) Spectroscopy: FTIR spectroscopy was used to study stratum corneum treated the same way as in the above DSC experiments, except the energy used was between 53 and 76 mJ. The spectra (see, e.g., FIGS. 32–33) show that absorption bands that are due to water, proteins and lipids change when the stratum corneum is irradiated. Some of these changes are consistent with changes seen during non-laser treatment of the stratum corneum (e.g. desiccation, thermal damage, lipid solubilization or protein denaturation). For example, the Amide I and II bands, which are due to the presence of proteins (most likely keratin, which makes up the bulk of protein in stratum corneum), shift to a larger wavenumber, consistent with the effect of desiccation alone (in the case of Amide II) or desiccation and beta-mercaptoethanol treatment (in the case of Amide I) (see, e.g., FIG. 34). The $CH_2$ vibrations (due to bonds in lipids) always shift to a smaller wavenumber indicating that either the intermolecular association between adjacent lipid molecules has been disturbed and/or the environment around the lipid molecules has changed in such a way that the vibrational behavior of the molecules changes (see, e.g., FIG. 35).

EXAMPLE 7

Figure 36:
FIG. 36 shows a histological section of rat skin that was irradiated at 80 mJ.
Figure 37:
FIG. 37 shows a histological section of human skin that was irradiated at 80 mJ.

Histology: Numerous in vivo experiments have been done on rats and humans. Usually, the skin is irradiated with the Er:YAG laser and a 2 mm spot and with a particular pulse energy, and then the irradiated site is biopsied immediately or 24 hours later. Two examples of typical results are shown in FIGS. 36 and 37. FIG. 36 shows rat skin irradiated at 80 mJ, which is an energy sufficient to make the skin permeable (to lidocaine, for instance) and yet does not show any sign of stratum corneum ablation. FIG. 37 depicts human skin 24 hours after being irradiated at 80 mJ. In this case, some change in the appearance of the stratum corneum has taken place (perhaps coagulation of some layers of stratum corneum into a darkly staining single layer), and yet the stratum corneum is still largely intact and is not ablated. Irradiation of human skin, in vivo, and subsequently examined under a dissection microscope, show that at subablative energies (less than about 90–120 mJ), the stratum corneum is still present on the skin. The irradiated stratum corneum appears slightly whitened in vivo, which might be evidence of desiccation or separation of the stratum corneum from the underlying tissues.

EXAMPLE 8

Figure 22:
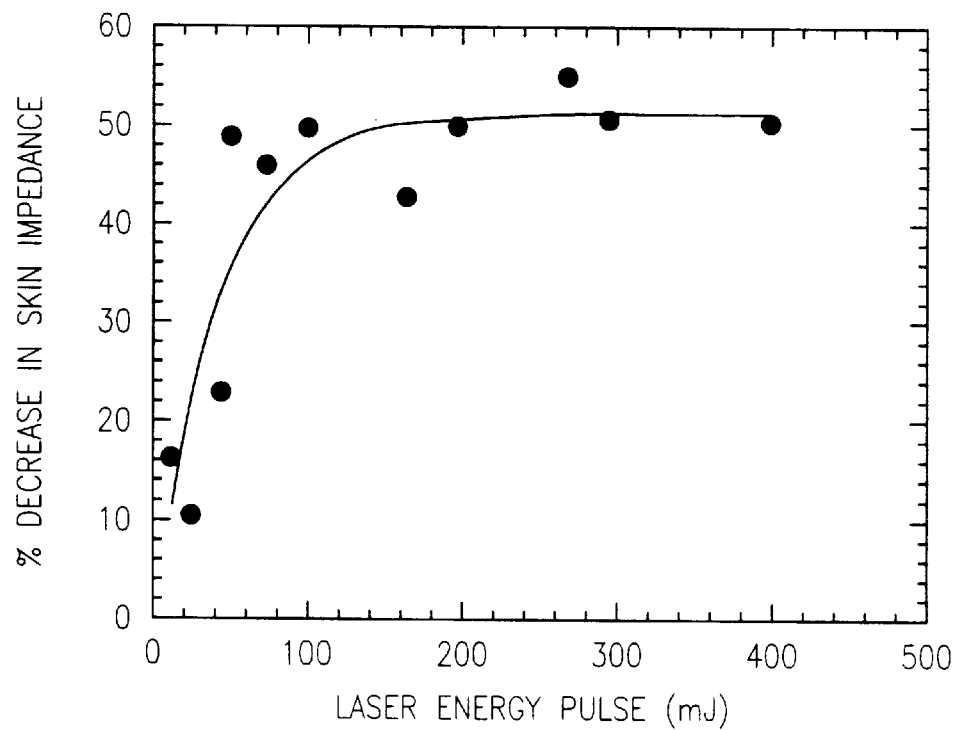
FIG. 22 shows the decrease in the impedance of skin in vivo using various laser pulse energies.

One way to quantify the reduction in the barrier function of the stratum corneum is to measure the reduction in the electrical impedance of the skin as a consequence of laser irradiation. In this experiment, separate 2 mm spots on the volar aspect of the forearm of a human volunteer were irradiated with a single pulse of radiant energy from the Er:YAG laser using a range of energies. An ECG electrode was then placed over the irradiated site and an unirradiated site about 20 cm away on the same forearm. A 100 Hz sine wave of magnitude 1 volt peak-to-peak was then used to measure the impedance of the skin. The results of a series of measurements are shown in FIG. 22, which shows that there is a decrease in skin impedance in skin irradiated at energies as low as 10 mJ, using the fitted curve to interpolate data.

EXAMPLE 9

Figure 21:
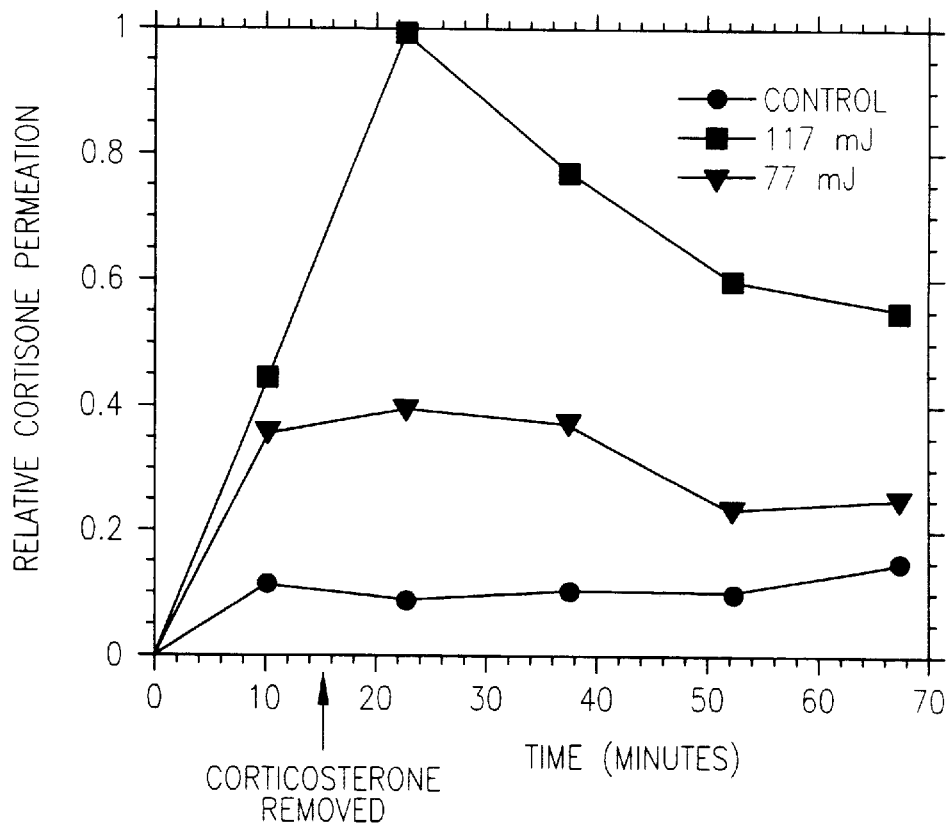
FIG. 21 is a chart showing a study using corticosterone which showed enhanced permeation (over controls) at an energies of 77 mJ and 117 mJ.
Figure 26:
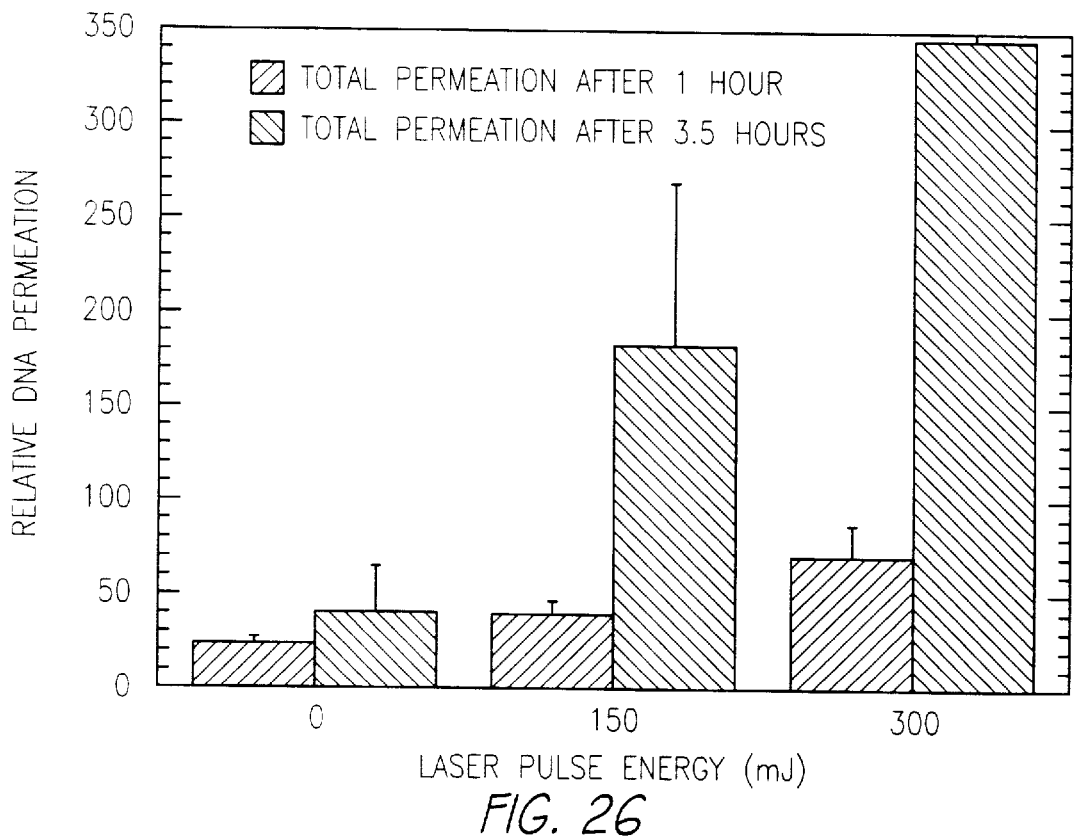
FIG. 26 is a chart of a study using DNA showing enhanced permeation through skin irradiated at an energy of 150 mJ and 300 mJ.

Pieces of human skin were placed in diffusion cells and irradiated with a single pulse of radiant energy produced by an Er:YAG laser. The spot size was 2 mm and the energy of the pulse was measured with a calibrated energy meter. After irradiation, the diffusion cells were placed in a 37 degrees Celsius heating block. Phosphate buffered saline was added to the receptor chamber below the skin and a small stir bar was inserted in the receptor chamber to keep the fluid continually mixed. Control skin was left unirradiated. Small volumes of radiolabelled compounds (either corticosterone or DNA) were then added to the donor chamber and left for 15 minutes before being removed (in the case of corticosterone) or were left for the entire duration of the experiment (in the case of the DNA). Samples were then taken from the receptor chamber at various times after application of the test compound and measured in a scintillation or gamma counter. The results of this experiment are shown in FIGS. 21 and 26. The results illustrate that enhanced permeation can occur at sub-ablative laser pulse energies (see the 77 mJ/pulse data for corticosterone). Although, in the case of the DNA experiment the energy used may have been ablative, enhanced permeation may still occur when lower energies are used.

EXAMPLE 10

Figure 23:
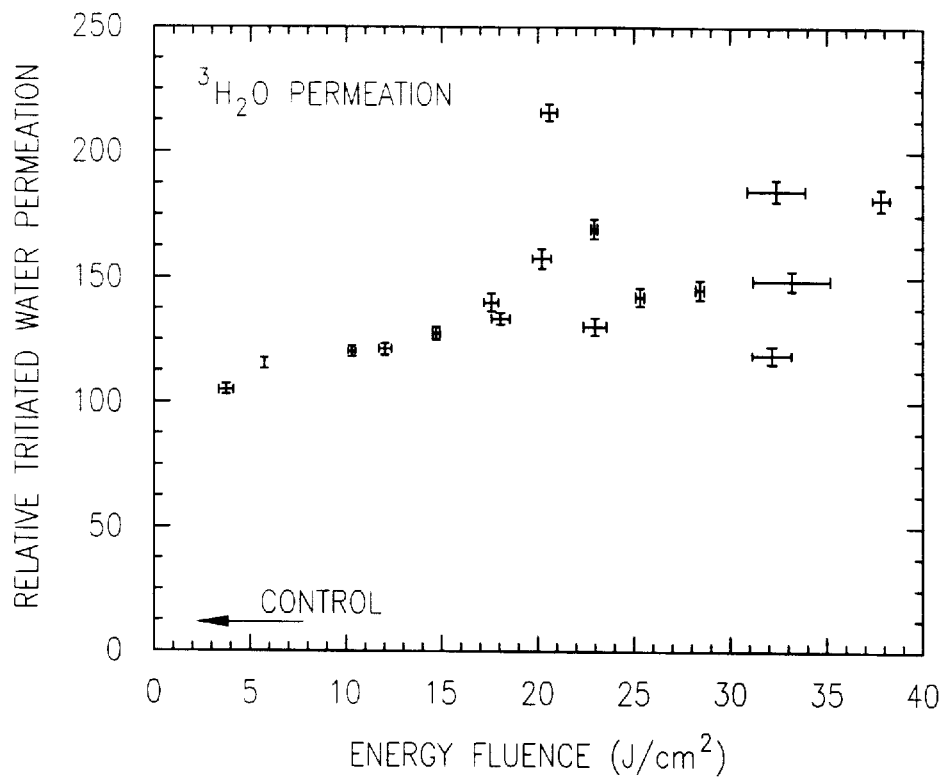
FIGS. 23–24 show in a permeation study of tritiated water($^3H_2O$) involving lased human skin at energies from 50 mJ (1.6 $J/cm^2$) to 1250 mJ (40 $J/cm^2$).
Figure 24:
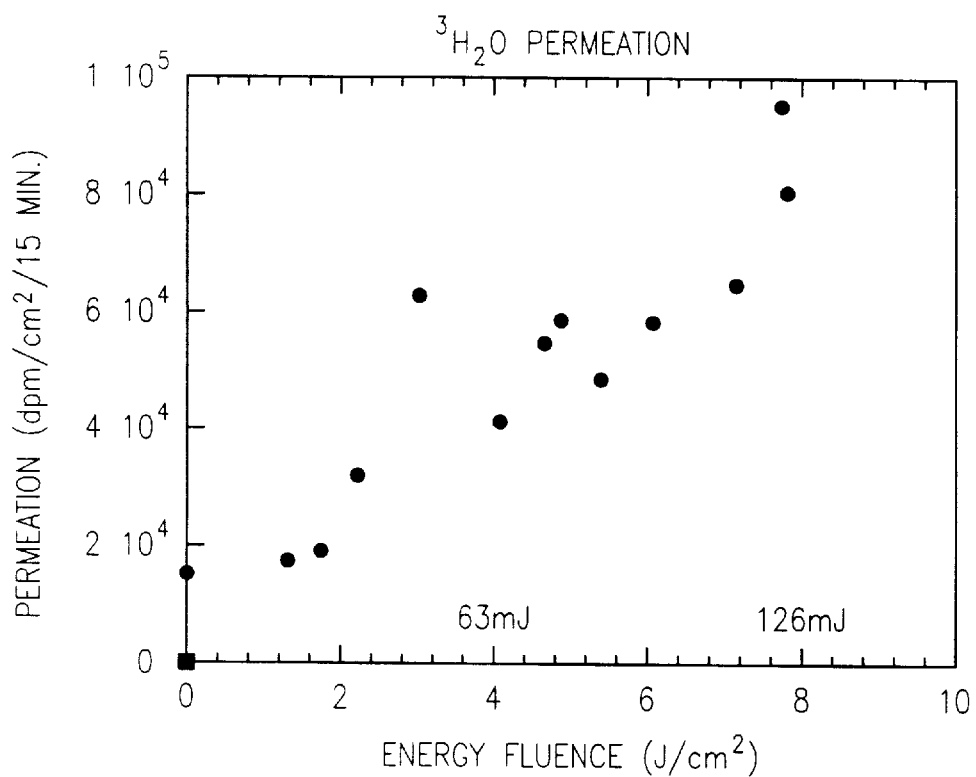
Figure 25A:
FIGS. 25A and 25B show histological sections of human skin irradiated at energies of 50 mJ and 80 mJ.
Figure 25B:

Histology studies on rat and human skin, irradiated either in vivo or in vitro, show little or no evidence of ablation when Er:YAG laser pulse energies less than about 100–200 mJ are used. (See, e.g., FIGS. 25a and 25b). Repeating this study showed the same results as the previous studies. An in vitro permeation study using tritiated water ($^3H_2O$) involving human skin lased at energies from 50 mJ (1.6 J/cm$^2$) to 1250 mJ (40 J/cm$^2$) determined (FIGS. 23 and 24) than an increase in permeation was seen at low energy fluences up to about 5 J/cm$^2$, whereupon the permeation is more-or-less constant. This shows that there has been a lased induced enhancement of permeation (of tritiated water) at energies that are sub-ablative.

EXAMPLE 11

Figure 39:
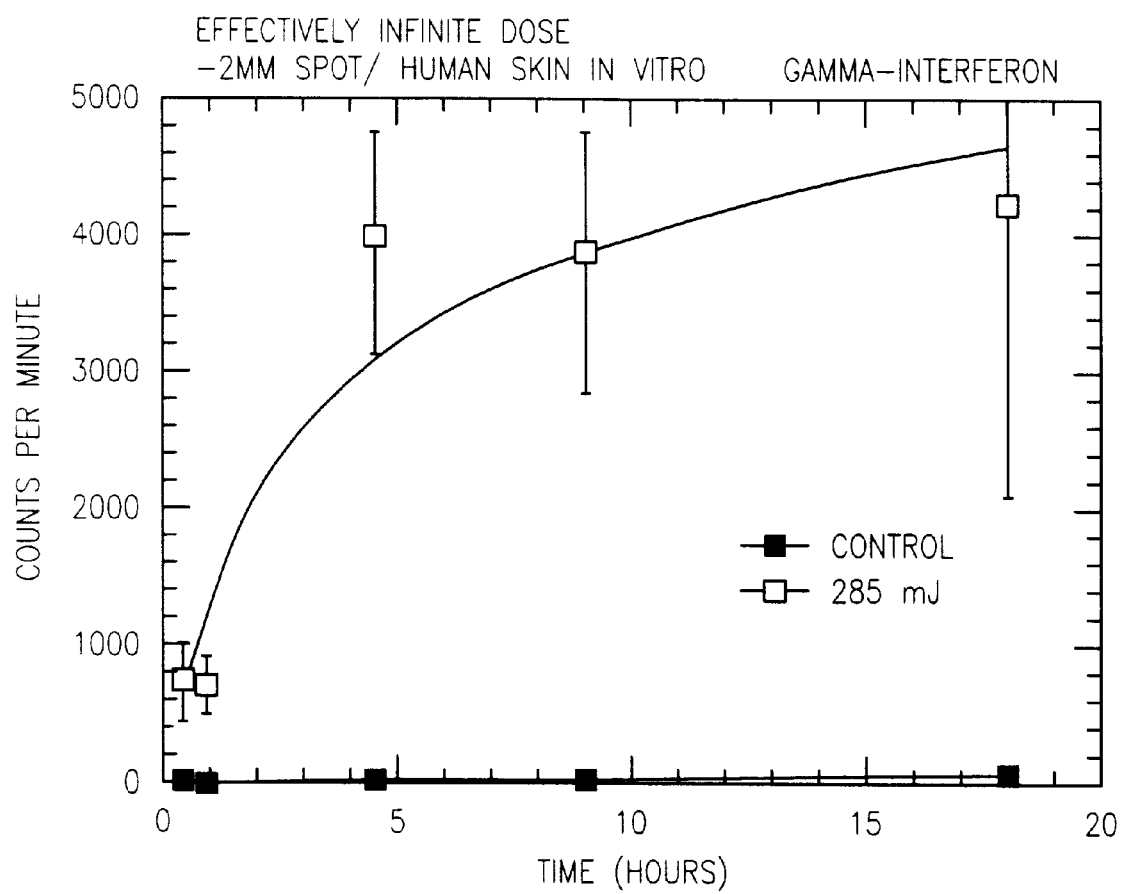
FIG. 39–41 shows permeation of γ-interferon, insulin and lidocaine, through human skin in vitro.
Figure 40:
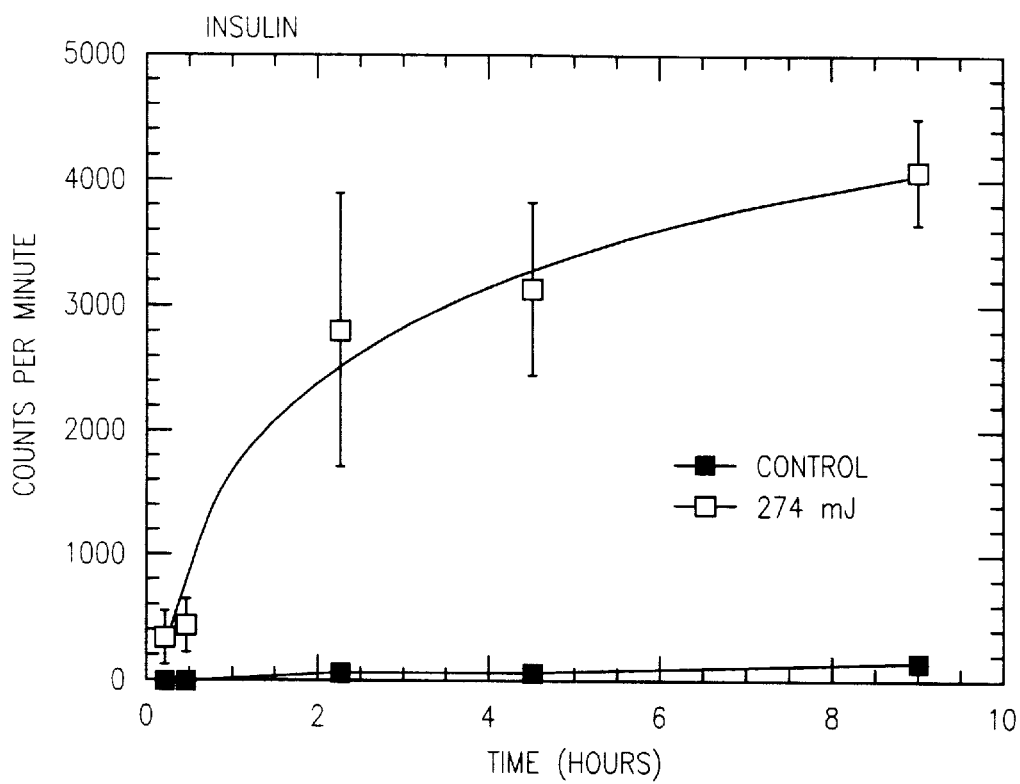
Figure 41:
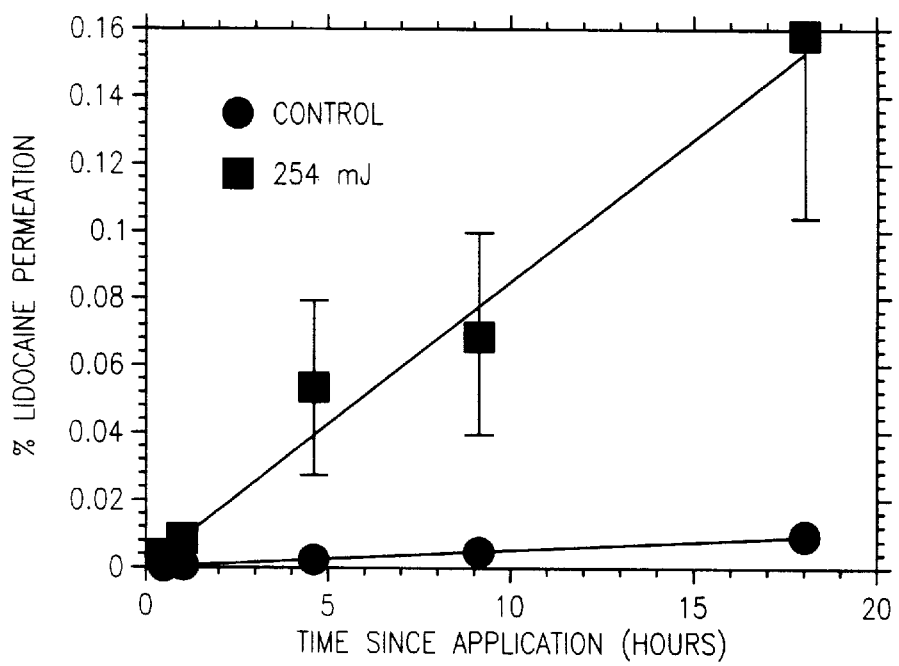

The output of the Er:YAG laser was passed through an aperture to define it's diameter as 2 mm. Human skin, purchased from a skin bank, was positioned in Franz diffusion cells. The receptor chamber of the cell was filled with 0.9% buffered saline. A single pulse, of measured energy, was used to irradiate the skin in separate diffusion cells. Control skin was left unirradiated. When the permeation of lidocaine was to be tested, a 254 mJ pulse was used, and multiple samples were irradiated. In the case of γ-interferon, a 285 mJ pulse was used, and multiple samples were irradiated. In the case of insulin, a 274 mJ pulse was used, and multiple samples were irradiated. In the case of cortisone, either 77 mJ or 117 mJ was used. After irradiation, a stirring magnet was place in the receptor chamber of the diffusion cells and the cells were placed in a heating block held at 37° C. The radiolabelled lidocaine, gammainterferon and insulin were diluted in buffered saline, and 100 μL of the resulting solutions was placed in the donor chamber of separate diffusion cells. The donor was left on the skin for the duration of the experiment. At various times post-drug-application, samples were taken from the receptor chamber and the amount of drug present was assayed with either a gamma-counter, or a liquid scintillation counter. Graphs of the resulting data are shown in FIGS. 39, 40 and 41. From this, and similar data, the permeability constants were derived and are shown as follows:

| Drug | Permeability Constant, $k_p$ ($\times 10^{-3}$ cm/hr) |
| --- | --- |
| Lidocaine | 2.62 +/− 6.9 |
| γ-Interferon | 9.74 +/− 2.05 |
| Insulin | 11.3 +/− 0.93 |

EXAMPLE 12

Figure 38A:
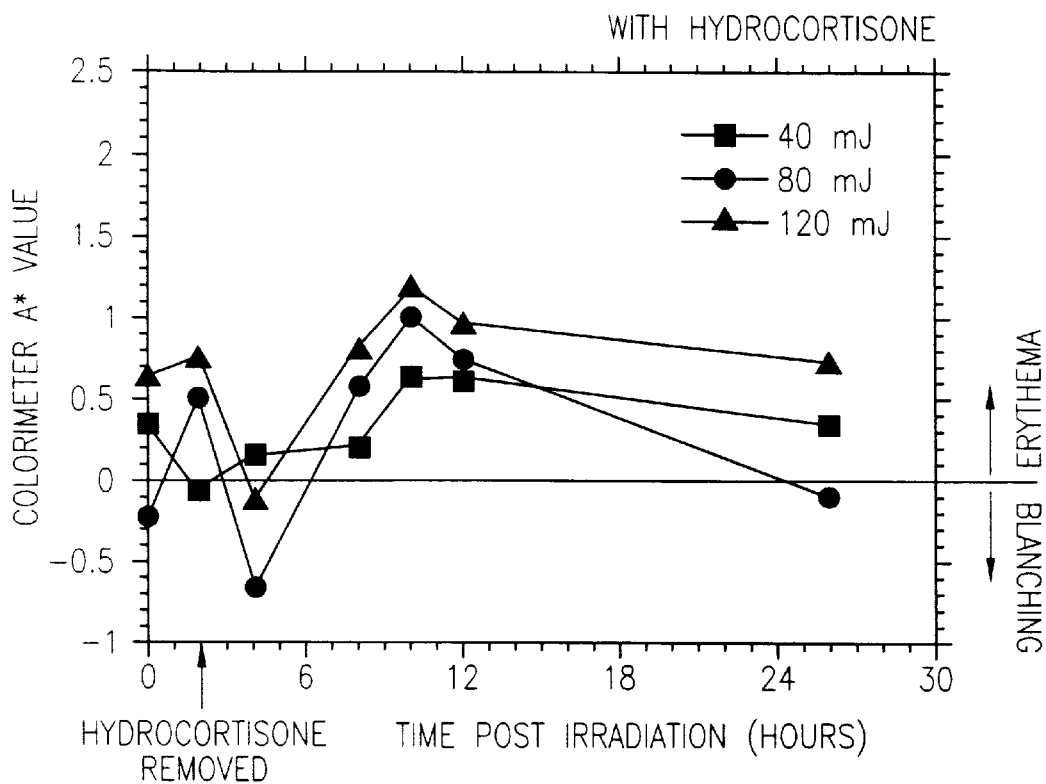
FIGS. 38A and 38B show in vivo blanching assay results.
Figure 38B:
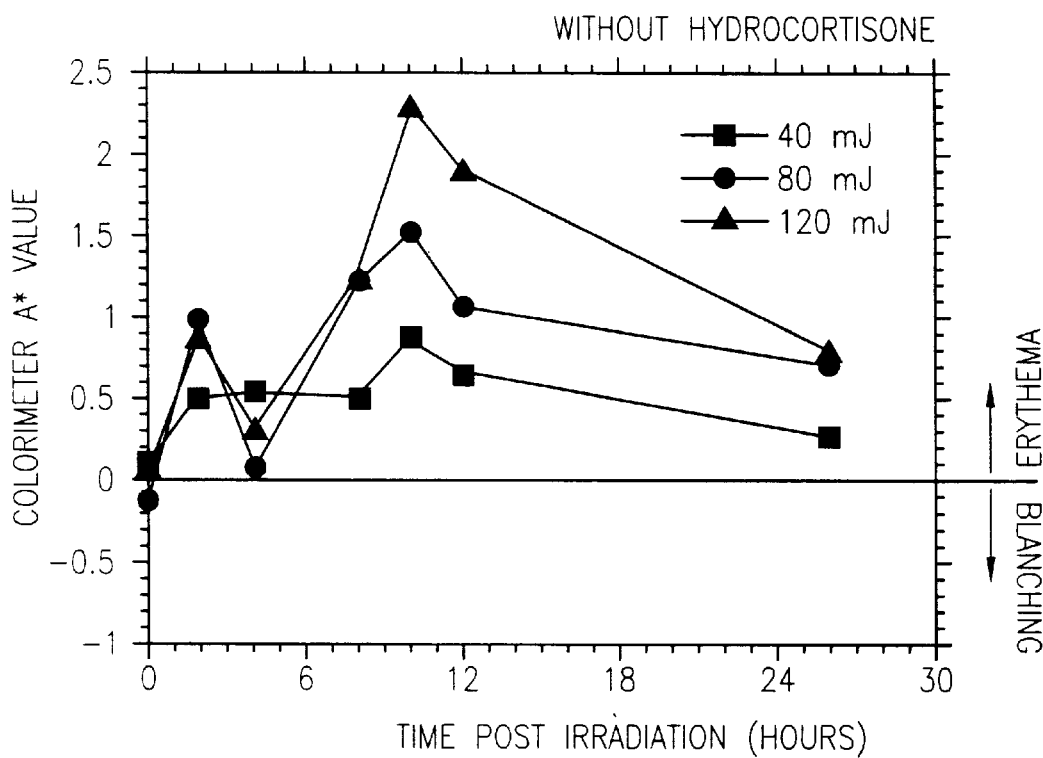

This data was collected during the same experiment as the TEWL results (see Example 2 and FIG. 27). In the case of the blanching assay, baseline skin color (redness) measurements were then taken of each spot using a Minolta CR-300 Chromameter (Minolta Inc., N.J.). The Er:YAG laser was then used to ablate six 2 mm spots on one forearm, at energies of 40, 80 and 120 mJ. A spot (negative calorimeter control) directly adjacent to the laser irradiated spots remained untouched. Subsequently, a thin film of 1% hydrocortisone ointment was applied to six of the lased spots on the treatment arm. One untouched spot on the contralateral arm was administered a thin layer of Diprolene (β-methasone), which is a strong steroid that can permeate the intact stratum corneum in an amount sufficient to cause measurable skin blanching. An occlusive patch, consisting of simple plastic wrap, was fixed with gauze and dermatological tape over all sites on both arms and left in place for two hours, after which the administered steroids were gently removed with cotton swabs. Colorimeter measurements were then taken over every unirradiated and irradiated spot at 2, 4, 8, 10, 12 and 26 hours post-irradiation, these results are shown in FIGS. 38a and 38b. Finally, the skin was clinically assessed for evidence of irritation at the 26 hour evaluation.

The results of the chromameter measurements show that some erythema (reddening) of the skin occurred, but because of the opposite-acting blanching permeating hydrocortisone, the reddening was less than that seen in the control spots which did not receive hydrocortisone. The Diprolene control proved the validity of the measurements and no problems were seen in the volunteers at the 26 hour evaluation, although in some of the cases the site of irradiation was apparent as a small red spot.

EXAMPLE 13

The radiant output of the Er:YAG laser is focussed and collimated with optics to produce a spot size at the surface of the skin of, for example, 5 mm. The skin of the patient, being the site of, or close to the site of disease, is visually examined for anything that might affect the pharmacokinetics of the soon to be administered drug (e.g., significant erythema or a wide-spread loss of the integrity of the stratum corneum). This site, which is to be the site of irradiation, is gently cleansed to remove all debris and any extraneous compounds such as perfume or a buildup of body oils. A disposable tip attached to the laser pressed up to the skin prior to irradiation is used to contain any ablated biological debris, as well as to contain any errant radiant energy produced by the laser. A single laser pulse (approximately 350 μs long), with an energy of 950 mJ, is used to irradiate the spot. The result is a reduction or elimination of the barrier function of the stratum corneum. Subsequently, an amount of pharmaceutical, hydrocortisone for example, is spread over the irradiation site. The pharmaceutical may be in the form of an ointment so that it remains on the site of irradiation. Optionally, an occlusive patch is placed over the drug in order to keep it in place over the irradiation site.

EXAMPLE 14

An infrared laser radiation pulse was formed using a solid state, pulsed, Er:YAG laser consisting of two flat resonator mirrors, an Er:YAG crystal as an active medium, a power supply, and a means of focusing the laser beam. The wavelength of the laser beam was 2.94 microns. The duration of the pulse was approximately 300 μs. The spot size was approximately 2 mm, with an energy fluence of 5 J/cm$^2$. Single pulses were used.

Three 2 mm diameter spots were created on a flaccid penis. Subsequent to ablation a pharmaceutical preparation of alprostadil (Caverject from Pharmacia & Upjohn, Kalamazoo, Mich.) was applied to a small patch consisting of tissue paper. The patch was applied to the multiple perforated areas of the skin on the then flaccid penis and held there with adhesive tape for 45 minutes. After approximately 35 minutes, the patient obtained an erection that was sustained for more than 1 hour.

The benefit of this route of administration is that it is painless. The normal method of administration of alprostadil involves injecting the compound deep into the corpus cavernosum of the penis with a hypodermic needle. Not only is such a procedure painful, but it also results in potentially infectious contaminated sharp.

EXAMPLE 15

An infrared laser radiation pulse can be formed using a solid state, pulsed, Er:YAG laser consisting of two flat resonator mirrors, an Er:YAG crystal as an active medium, a power supply, and a means of focusing the laser beam. The wavelength of the laser beam is preferably 2.94 microns. The duration of the pulse is preferably approximately 300 μs. The spot size is preferably approximately 2 mm, with an impulse energy of approximately 150 mJ creating an energy fluence of approximately 5 J/cm$^2$.

Single pulses of radiant energy from the TRANS-MEDICA™ Er:YAG laser, with the operating parameters described above, is preferably used to irradiate 2 mm diameter spots on areas of the scalp exhibiting hair loss. Multiple irradiation sites can be used. Subsequent to irradiation, minoxidil (for example Rogaine from Pharmacia & Upjohn, Kalamazoo, Mich.) may be applied to access interstitial spaces in the scalp, allowing greater quantities of the pharmaceutical to stimulate root follicles than is available by transcutaneous absorption alone. Alternatively, subsequent to ablation, androgen inhibitors may be applied through the laser ablated sites. These inhibitors act to counter the effects of androgens in hair loss.

EXAMPLE 16

Skin resurfacing is a widely used and commonly requested cosmetic procedure whereby wrinkles are removed from (generally) the face of a patient by ablating approximately the outermost 400 microns of skin with the radiant energy produced by a laser (Dover J. S., Hruza G. J., "Laser Skin Resurfacing," Semin. Cutan. Med. Surg., 15(3) :177–88, 1996). After treatment, often a "mask" made out of hydrogel (which is a gelatine-like material that consists mostly of water) is applied to the irradiated area to provide both a feeling of coolness and also to prevent undesirable desiccation of the treated skin and "weeping" of bodily fluids.

The pain associated with this procedure would be intolerable without the use of local or general anesthesia. Generally, multiple (perhaps up to 30) local injections of lidocaine are completed prior to the irradiation of the skin. These injections themselves take a significant amount of time to perform and are themselves relatively painful.

Single pulses of radiant energy from the TRANS-MEDICA™ Er:YAG laser is preferably used to irradiate 2 mm diameter spots on areas of the face required for the multiple applications of lidocaine prior to skin resurfacing. The energy used in each laser pulse is preferably 150 mJ. Subsequent to irradiation, lidocaine is applied for general anesthesia. Furthermore, by incorporating lidocaine (preferably, the hydrophillic version which is lidocaine-HCl) into the hydrogel, or other patch or gel means of containment, and applying this complex (in the physical form of a "face-mask") to the patient's face prior to the laser irradiation but after ablating the stratum corneum with the Er:YAG laser from a matrix of sites throughout the treatment area, sufficient anesthesia will be induced for the procedure to be done painlessly. It may also be beneficial to incorporate a sedative within the hydrogel to further prepare the patient for what can be a distressing medical procedure. Optionally, the "face-mask" can be segmented into several aesthetic-units suitable for single application to particular laser-treatment regions of the face. Finally, another "face-mask" incorporating beneficial pharmaceuticals, such as antibiotics (e.g. Bacitracin, Neosporin, Polysporin, and Sulphadene) or long term topical or systemic analgesics, such as fentanyl or demeral, can be applied to the patient after skin resurfacing treatment.

EXAMPLE 17

The growth of hairs in the nose (primarily in men) is a common cosmetic problem. The current therapy, which involves pulling the hairs out with tweezers, is painful and nonpermanent. An infrared laser radiation pulse can be formed using a solid state, pulsed, Er:YAG laser consisting of two flat resonator mirrors, an Er:YAG crystal as an active medium, a power supply, and a means of focusing the laser beam. The wavelength of the laser beam is preferably 2.94 microns. The duration of the pulse approximately is preferably 300 $\mu$s. The spot size is preferably approximately 2 mm, with an impulse energy of approximately 150 mJ creating an energy fluence of approximately 5 $J/cm^2$.

Single pulses of radiant energy from the TRANS-MEDICA™ Er:YAG laser is preferably used, with the above described operating parameters, to irradiate 2 mm diameter spots on the nasal mucosa exhibiting cosmetically unappealing hair growth. Multiple irradiation sites can be used. The irradiation by itself can be sufficient to alter the tissue thereby inhibiting subsequent hair growth thus irradiation may be itself sufficient to alter the tissue, inhibiting subsequent hair growth. Alternatively, subsequent to irradiation, a dye, for example indocyanine green, which absorbs different wavelengths of radiation, can be applied. After the dye has been absorbed into the nasal passage, 810 nm radiant energy from a diode laser (GaAlAs laser) can be used to raise the temperature of the surrounding tissue. This acts to selectively damage the hair follicles in contact with the dye. As a result the nasal tissue is modified so that hair growth does not reoccur, or at least does not recur as quickly as it does after manual hair removal.

While various applications of this invention have been shown and described, it should be apparent to those skilled in the art that many modifications of the described techniques are possible without departing from the inventive concepts herein.

We claim:

1. A method for preparing the skin for treatment of cutaneous or subcutaneous compounds, comprising the steps of:
   a) focusing a laser beam with sufficient energy fluence to alter the skin at least as deep as the stratum corneum, but not as deep as the capillary layer;
   b) firing the laser to create a site of alteration, the site having a diameter of between 0.5 microns and 5.0 cm;
   c) applying a dye, a compound that alters the optical properties of stratum corneum, or a compound that stimulates the body's production of molecules that are strong absorbers of light; and
   d) firing a second laser with a wavelength that is absorbed by the applied dye, the compound that stimulates the optical properties of stratum corneum or the compound that stimulates the body's production of molecules that are strong absorbers of light.

2. The method of claim 1 wherein the laser beam has a wavelength of 0.2–10 microns.

3. The method of claim 1 wherein the laser beam has a wavelength of between 1.5–3.0 microns.

4. The method of claim 1 wherein the laser beam has a wavelength of about 2.94 microns.

5. The method of claim 1 wherein the laser beam is emitted by a laser selected from the group consisting of continuous wave-lasers Er:YAG, pulsed $CO_2$, Ho:YAG, Er:YAP, Er/Cr:YSGG, Ho:YSGG, Er:GGSG, Er:YLF, Tm:YAG, Ho:YAG, Ho/Nd:Yalo$_3$, cobalt:$MgF_2$, HF chemical, DF chemical, carbon monoxide, deep UV lasers, and frequency tripled Nd:YAG lasers.

6. The method of claim 1 wherein the laser beam is emitted by a modulated laser selected from the group consisting of continuous-wave $CO_2$, Nd:YAG, Thullium:YAG and diode lasers.

7. The method of claim 1 wherein the laser beam is emitted by an Er:YAG laser.

8. The method of claim 1 wherein the laser beam is focused at a site on the skin with a diameter of 0.1–5.0 mm.

9. The method of claim 1 wherein the energy fluence of the laser beam at the skin is 0.03–100,000 $J/cm^2$.

10. The method of claim 1 wherein the energy fluence of the laser beam at the skin is 0.03–9.6 $J/cm^2$.

11. The method of claim 1 wherein the pulse width is between 1 femtosecond and 1,000 microseconds.

12. The method of claim 1 wherein the pulse width is between 1 and 1000 microseconds.

13. The method of claim 1 wherein multiple alterations are made to prepare the skin for dye delivery.

14. The method of claim 1 further comprising a beam splitter positioned to create, simultaneously from the laser, multiple sites of alteration.

15. The method of claim 14 wherein the beam splitter is selected from a series of partially silvered mirrors, a series of dichroic mirrors, and a series of beam-splitting prisms.

16. The method of claim 14 further comprising a means to deflect the beam at different angles to create different sites of alteration on the skin.

17. The method of claim 14 further comprising a means to scan the laser beam to create one continuous path of alteration.

18. The method of claim 1 wherein the dye is used to stain subcutaneous structures.

19. The method of claim 1 wherein the dye is indocyanine green.

20. The method of claim 1 wherein the dye is specific for lipids, proteins, or carbohydrates.

21. The method of claim 1 wherein the wavelength of the laser beam fired from the second laser at the site of dye delivery is about the wavelength of peak absorption of the dye.

22. The method of claim 21 wherein the wavelength of the laser beam is about 810 nm.

23. The method of claim 1 wherein the wavelength of the laser beam fired from the second laser at the site of delivery of the compound that stimulates the body's production of molecules that are strong absorbers of light is about the wavelength of peak absorption of the compound.

24. The method of claim 23 wherein the compound that stimulates the body's production of molecules that are strong absorbers of light is 5-aminolevulinic acid.

25. A method for increasing the diffusion of bodily fluids out of, or compounds into, the skin, comprising the steps of:
  a) applying a compound or an absorbing material to a targeted tissue site;
  b) focusing a laser beam with sufficient energy fluence to create a pressure gradient within the stratum corneum, in the applied compound, or in the optional absorbing material; and
  c) firing the laser with at least one short rapid pulse to create the pressure gradient.

26. The method of claim 25 wherein the laser beam has a wavelength of 0.2–10 microns.

27. The method of claim 25 wherein the laser beam has a wavelength of between 1.5–3.0 microns.

28. The method of claim 25 wherein the laser beam has a wavelength of about 2.94 microns.

29. The method of claim 25 wherein the laser beam is emitted by a laser selected from the group consisting of Er:YAG, pulsed $CO_2$ Ho:YAG, Er:YAP, Er/Cr:YSGG, Ho:YSGG, Er:GGSG, Er:YLF, Tm:YAG, Ho:YAG, Ho/Nd:YalO$_3$, cobalt:MgF$_2$, HF chemical, DF chemical, carbon monoxide, deep UV lasers, and frequency tripled Nd:YAG lasers.

30. The method of claim 25 wherein the laser beam is emitted by an Er:YAG laser.

31. The method of claim 25 wherein the laser beam is emitted by a modulated laser selected from the group consisting of continuous-wave $CO_2$, Nd:YAG, Thallium:YAG and diode lasers.

32. The method of claim 25 wherein the pulse width is between 1 femtosecond and 1,000 microseconds.

33. The method of claim 25 wherein the pulse width is between 1 and 1000 microseconds.

34. The method of claim 25 wherein the optional absorbing material is placed on or over the targeted tissue before application of the compound or firing the laser.

35. The method of claim 34 wherein the pressure gradient is created in the optional absorbing material.

36. The method of claim 34 wherein the optional absorbing material is a thin film of water.

37. The method of claim 34 wherein the optional absorbing material is a dye or a solution with a dye.

38. The method of claim 25 wherein the compound is applied before firing the laser.

39. The method of claim 25 wherein the pressure gradient is created in the stratum corneum simultaneous with the application of the compound.

40. The method of claim 38 wherein the pressure gradient is created in the compound.

41. The method of claim 38 wherein the optional absorbing material is placed on or over the compound before firing the laser.

42. The method of claim 41 wherein the pressure gradient is created in the optional absorbing material.

43. The method of claim 41 wherein the optional absorbing material is a thin film of water.

44. The method of claim 25 wherein multiple pulses are used to create the pressure gradient.

45. The method of claim 25 wherein the stratum corneum is ablated or altered before the pressure gradient is created.

46. A method for increasing the diffusion of bodily fluids out of, or compounds into, the skin, comprising the steps of:
  a) focusing a laser beam with sufficient energy fluence to create plasma in an optional absorbing material on or over a targeted tissue site;
  b) firing the laser with at least one short rapid pulse to create a site of plasma, the site having a diameter of between 0.5 microns and 5 mm; and
  c) removing bodily fluids from the targeted tissue or applying a compound to the targeted tissue.

47. The method of claim 46 wherein the laser beam has a wavelength of 0.2–10 microns.

48. The method of claim 46 wherein the laser beam has a wavelength of between 1.5–3.0 microns.

49. The method of claim 46 wherein the laser beam has a wavelength of about 2.94 microns.

50. The method of claim 46 wherein the laser beam is emitted by a laser selected from the group consisting of Er:YAG, pulsed $CO_2$ Ho:YAG, Er:YAP, Er/Cr:YSGG, Ho:YSGG, Er:GGSG, Er:YLF, Tm:YAG, Ho:YAG, Ho/Nd:YalO$_3$, cobalt:MgF$_2$, HF chemical, DF chemical, carbon monoxide, deep UV lasers, and frequency tripled Nd:YAG lasers.

51. The method of claim 46 wherein the laser beam is emitted by an Er:YAG laser.

52. The method of claim 46 wherein the laser beam is emitted by a modulated laser selected from the group consisting of continuous-wave $CO_2$, Nd:YAG, Thallium:YAG and diode lasers.

53. The method of claim 46 wherein the pulse width is between 1 femtosecond and 1,000 microseconds.

54. The method of claim 46 wherein the pulse width is between 1 and 1000 microseconds.

55. The method of claim 46 wherein multiple pulses are used to create multiple sites of plasma.

56. The method of claim 46 wherein the optional absorbing material is placed on or over the targeted tissue before firing the laser.

57. The method of claim 56, wherein plasma is created in the optional absorbing material.

58. The method of claim 56, wherein the optional absorbing material is a thin film of water.

59. The method of claim 56, wherein the optional absorbing material is a dye or a solution with a dye.

60. The method of claim 46 wherein the compound is applied before firing the laser.

61. The method of claim 60, wherein plasma is created in the applied compound.

62. A method for increasing the diffusion of bodily fluids out of, or compounds into, the skin, comprising the steps of:

a) focusing a laser beam with sufficient energy fluence to create cavitation bubbles in an applied compound, or in an optional absorbing material on or over a targeted tissue site;

b) firing the laser with at least one short rapid pulse to create a site of cavitation bubbles, the site having a diameter of between 0.5 microns and 5 mm; and c) removing bodily fluids from the targeted tissue or applying a compound to the targeted tissue.

63. The method of claim 62, wherein the laser beam has a wavelength of 0.2–10 microns.

64. The method of claim 62, wherein the laser beam has a wavelength of between 1.5–3.0 microns.

65. The method of claim 62, wherein the laser beam has a wavelength of about 2.94 microns.

66. The method of claim 62, wherein the laser beam is emitted by a laser selected from the group consisting of Er:YAG, pulsed $CO_2$ Ho:YAG, Er:YAP, Er/Cr:YSGG, Ho:YSGG, Er:GGSG, Er:YLF, Tm:YAG, Ho:YAG, Ho/Nd:YalO$_3$, cobalt:MgF$_2$, HF chemical, DF chemical, carbon monoxide, deep UV lasers, and frequency tripled Nd:YAG lasers.

67. The method of claim 62, wherein the laser beam is emitted by an Er:YAG laser.

68. The method of claim 62, wherein the pulse width is between 1 femtosecond and 1,000 microseconds.

69. The method of claim 62, wherein the pulse width is between 1 and 1000 microseconds.

70. The method of claim 62, wherein the laser beam is emitted by a modulated laser selected from the group consisting of continuous-wave $CO_2$, Nd:YAG, Thallium:YAG and diode lasers.

71. The method of claim 62, wherein multiple pulses are used to create multiple sites of cavitation bubbles.

72. The method of claim 62, wherein the optional absorbing material is placed on or over the targeted tissue before firing the laser.

73. The method of claim 72, wherein the cavitation bubbles are created in the optional absorbing material.

74. The method of claim 72, wherein the optional absorbing material is a thin film of water.

75. The method of claim 72, wherein the optional absorbing material is a dye or a solution with a dye.

76. The method of claim 62, wherein the compound is applied before firing the laser.

77. The method of claim 76, wherein the cavitation bubbles are created in the applied compound.

* * * * *

UNITED STATES PATENT AND TRADEMARK OFFICE
CERTIFICATE OF CORRECTION

PATENT NO. : 6,315,772 B1  Page 1 of 1
DATED : November 13, 2001
INVENTOR(S) : Kevin S. Marchitto et al.

It is certified that error appears in the above-identified patent and that said Letters Patent is hereby corrected as shown below:

Column 34,
Line 13, change "treatment of cutaneous" to -- treatment by cutaneous --.

Column 35,
Line 28, change "a compound or an absorbing material" to -- a compound and optionally an absorbing material --.

Column 36,
Line 21, after "create plasma" insert -- on or above the surface of a targeted tissue site, or --.
Line 22, change "over a targeted tissue site" to -- over the targeted tissue site --.

Signed and Sealed this

Twenty-second Day of October, 2002

Attest:

Attesting Officer

JAMES E. ROGAN
Director of the United States Patent and Trademark Office